United States Patent
Shimada et al.

(10) Patent No.: US 9,040,215 B2
(45) Date of Patent: May 26, 2015

(54) AMINE COMPOUND, ELECTROPHOTOGRAPHIC PHOTOCONDUCTOR, IMAGE FORMING METHOD, IMAGE FORMING APPARATUS, AND PROCESS CARTRIDGE

(71) Applicants: Tomoyuki Shimada, Shizuoka (JP); Masayoshi Nomura, Shizuoka (JP); Ryota Arai, Shizuoka (JP)

(72) Inventors: Tomoyuki Shimada, Shizuoka (JP); Masayoshi Nomura, Shizuoka (JP); Ryota Arai, Shizuoka (JP)

(73) Assignee: Ricoh Company, Ltd., Tokyo (JP)

( * ) Notice: Subject to any disclaimer, the term of this patent is extended or adjusted under 35 U.S.C. 154(b) by 5 days.

(21) Appl. No.: 13/753,083

(22) Filed: Jan. 29, 2013

(65) Prior Publication Data

US 2013/0202994 A1    Aug. 8, 2013

(30) Foreign Application Priority Data

Feb. 3, 2012 (JP) .................. 2012-021569
Feb. 29, 2012 (JP) .................. 2012-042916
Dec. 11, 2012 (JP) .................. 2012-270031

(51) Int. Cl.
G03G 15/00 (2006.01)
C07C 211/54 (2006.01)
G03G 5/06 (2006.01)

(52) U.S. Cl.
CPC ............ *G03G 15/751* (2013.01); *C07C 211/54* (2013.01); *G03G 5/0614* (2013.01); *G03G 2215/00957* (2013.01)

(58) Field of Classification Search
CPC .... G03G 5/0614; G03G 5/612; G03G 15/751
USPC ................... 430/69, 58.65, 66, 58.75, 73, 74; 399/159
See application file for complete search history.

(56) References Cited

U.S. PATENT DOCUMENTS 6,187,491 B1    2/2001 Ferrar et al.
7,112,392 B2 *  9/2006 Shimada et al. ............... 430/74

(Continued)

FOREIGN PATENT DOCUMENTS

JP    60-196768    10/1985
JP    5-158258     6/1993

(Continued)

OTHER PUBLICATIONS 13753083-4592278-EICSEARCH.pdf, pp. 3-58.*
Combined Chinese Office Action and Search Report issued Mar. 3, 2014 in Patent Application No. 201310042649.5 (with English language translation).

(Continued)

*Primary Examiner* — Thorl Chea
(74) *Attorney, Agent, or Firm* — Oblon, McClelland, Maier & Neustadt, L.L.P.

(57) ABSTRACT

To provide an amine compound, represented by General Formula (I) below:

General Formula (I)

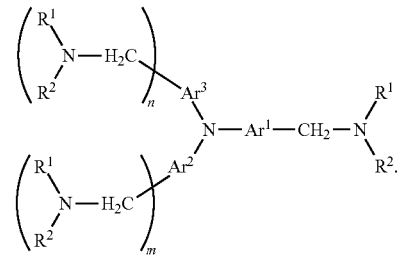

[In General Formula (I), $R^1$ and $R^2$ represent a substituted or unsubstituted alkyl group, a substituted or unsubstituted aralkyl group, or a substituted or unsubstituted aromatic hydrocarbon group, which may be identical or different; m and n are an integer of 1 or 0; $Ar^1$ represents a substituted or unsubstituted aromatic hydrocarbon group; $Ar^2$ and $Ar^3$ represent a substituted or unsubstituted alkyl group, a substituted or unsubstituted aralkyl group, or a substituted or unsubstituted aromatic hydrocarbon group; and $Ar^1$ and $Ar^2$ or $Ar^2$ and $Ar^3$ may bind to each other to form a substituted or unsubstituted heterocyclic group including a nitrogen atom.]

16 Claims, 9 Drawing Sheets

(56) References Cited

U.S. PATENT DOCUMENTS

| | | | |
|---|---|---|---|
| 2002/0007056 A1* | 1/2002 | Shimada et al. | 540/124 |
| 2004/0180280 A1* | 9/2004 | Ikegami et al. | 430/73 |

FOREIGN PATENT DOCUMENTS

| | | |
|---|---|---|
| JP | 10-168447 A | 6/1998 |
| JP | 2884353 | 2/1999 |
| JP | 2006-093279 A | 4/2006 |
| JP | 3949550 | 4/2007 |
| JP | 3996490 | 8/2007 |
| JP | 4101676 | 3/2008 |
| JP | 4226749 | 12/2008 |
| JP | 2009-14851 | 1/2009 |
| WO | WO 02/12224 A2 | 2/2002 |

OTHER PUBLICATIONS

Masafumi Yano, et al., "Synthesis and properties of a redox active ligand with bispicorylamino groups and its dinuclear complex" Polyhedron, vol. 26, 2007, pp. 2174-2178.

Masafumi Yano, et al., "Synthesis and properties of a redox active starburst ligand with three bispicorylamino groups and its trinuclear complexes" Polyhedron, vol. 28, 2009, pp. 1935-1939.

Xin Zhang, et al., "Effect of the Electron Donor/Acceptor Orientation on the Fluorescence Transduction Efficiency of the d-Pet Effect of Carbazole-Based Fluorescent Boronic Acid Sensors" Journal of Organic Chemistry, vol. 75, No. 8, 2010, pp. 2578-2588.

Akihiko Itami, et al., "The Effects of Nitrogen Oxide on the Resolution of Organic Photoconductors", Konica Technical Report, vol. 13, 2000, 5 pages.

* cited by examiner

AMINE COMPOUND, ELECTROPHOTOGRAPHIC PHOTOCONDUCTOR, IMAGE FORMING METHOD, IMAGE FORMING APPARATUS, AND PROCESS CARTRIDGE

BACKGROUND OF THE INVENTION

1. Field of the Invention

The present invention relates to: an amine compound; an electrophotographic photoconductor including the amine compound; and an image forming method, an image forming apparatus and a process cartridge using the electrophotographic photoconductor.

2. Description of the Related Art

In recent years, development of an information-processing system device using an electrophotographic method is remarkable. In particular, a laser printer and a digital copier, which convert information to digital signals and carry out information recording with light, have improved significantly in terms of their print quality and reliability. Further, through combination with high-speed technology, they have been applied to a laser printer or a digital copier with which a full-color printing is possible. From such a background, to have both high image quality and high durability as functions required for a photoconductor has become an especially important issue.

As a photoconductor used for these electrophotographic laser printer and digital copier, a photoconductor with an organic photosensitive material (OPC) is widely used in general for reasons such as cost, productivity and free of pollution. In addition, a layer configuration of the OPC photoconductor is divided into a single-layer structure and a functionally separated laminated structure. For example, a PVK-TNF charge-transfer complex photoconductor as a first practical OPC had the former single-layer structure. Meanwhile, a PVK/a-Se multilayer photoconductor was invented independently by Hayashi and Regensburger in 1968, and later, a multilayer photoconductor was presented by Melz et al. in 1977 and by Schlosser in 1978, where the photoconductive layer, namely an organic pigment dispersion layer and an organic low-molecular-weight dispersed polymer layer, was composed totally of an organic material. These are also called as a functionally separated laminated photoconductor because of a concept that it is composed of a charge generation layer (CGL) which absorbs light and generate charge and a charge transport layer (CTL) which injects and transports the charge generated by the CGL and neutralizes a surface charge. By development of this functionally separated laminated photoconductor, sensitivity and durability have drastically improved compared to a single-layer photoconductor. Also, since individual molecular designs of materials having different functions, namely a charge generation material (CGM) and a charge transport material (CTM), are possible, choice of these materials has greatly increased. Because of these reasons, the functionally separated laminated photoconductor is a major layer configuration of the present OPC photoconductor.

A mechanism of an electrostatic latent image formation in a functionally separated photoconductor is as follows. A light is irradiated to a charged photoconductor, the light passes a charge transport layer and is absorbed by a charge generation material in a charge generation layer, and charge is generated. The charge generated thereby is injected into the charge transport layer at an interface between the charge generation layer and the charge transport layer, it is further transferred within the charge transport layer by means of an electric field, and it neutralize the surface charge of the photoconductor. Thereby, an electrostatic latent image is formed.

However, an organic photoconductor is subjected to severe film chipping due to repeated use. As the film chipping in the photoconductive layer progresses, background smear, image density decrease or image degradation caused by decrease in charge potential and degradation of light sensitivity of the photoconductor and scratches on a surface of the photoconductor tend to progress. Accordingly, abrasion resistance of the organic photoconductor has been conventionally pointed out as a big issue. Further, in recent years, high durability of a photoconductor has been more important than ever due to reduction in diameter of the photoconductor due to speeding up of an electrophotographic device or downsizing of an apparatus.

As a method for achieving improved abrasion resistance of a photoconductor, methods of lubricating, curing or incorporating a filler to a photoconductive layer, or a method of using a polymeric charge transport material instead of a low-molecular charge transport material (CTM) molecule dispersed polymer layer are widely known. However, suppression of chipping in a photoconductive layer by these methods causes a new problem. That is, it has been known that ozone, NOx, or other oxidizing substances produced by repeated use or the surrounding environment are adsorbed on a surface of the photoconductive layer, which leads to low resistivity of an outermost surface depending on the repeated use and the use environment, causing problems such as image deletion (image blurring). Conventionally, this blur-generating substance is chipped off along with the photoconductive layer, and the problem has been avoided to some degree. However, as described above, a new technique must be employed to meet recent demands for higher resolution and higher durability. There is a method of carrying a heater on a photoconductor to evaporate a blurring substance as one of the methods to reduce effects thereof, but this method is a big obstacle for downsizing of an apparatus and reduction of energy consumption. Also, an additive such as antioxidant is an effective method, but an ordinary additive does not have photoconductivity. Thus, addition of a large amount to a photoconductive layer causes problems of electrophotographic characteristics such as low sensitivity and increased residual potential.

As above, the electrophotographic photoconductor imparted with high wear resistance, or less chipping because of process design around the photoconductor cannot avoid effects on image quality such as occurrence of image blurring and decreased resolution as side effects, and it has been considered difficult to obtain both high durability and high image quality. High resistance is preferable for suppressing occurrence of image blurring, and low resistance is preferable for suppressing elevation of residual potential. These are in a trade-off relation, which makes it difficult to solve the problems.

Meanwhile, in Japanese Patent (JP-B) No. 4226749, an aromatic compound having a dialkylamino group as an acid scavenger of a photoconductor is disclosed. Also, diamine compounds are disclosed in Japanese Patent Applications Laid-Open (JP-A) No. 5-158258 and JP-A No. 2009-14851. These compounds are described to be effective for image quality after repeated use of a photoconductor and to solve the problems of image deletion (image blurring) by the blur generating substance such as oxidizing gas. However, due to low charge transportability, it is difficult to respond to the requests for high sensitivity and speeding up, and accordingly, there is a limit in an amount of addition.

Further, it is reported that stilbene compounds including a dialkylamino group disclosed in JP-A No. 60-196768, JP-B No. 2884353, etc. are effective for image blurring due to an oxidizing gas ([Itami et al., Konica Technical Report, Vol. 13, p. 37, 2000]).

However, since the stilbene compounds include a dialkylamino group as a substituent having a strong mesomeric effect (+M effect) at a resonance region of a triarylamine structure as a charge transport site, an ionization potential value as a whole is abnormally small. Therefore, charge retention capacity of a photoconductive layer which uses it solely as a charge transport material is initially poor or degrades severely due to repeated use, and it has a fatal defect that practical use is extremely difficult. Also, even though it is mixed with other charge transport materials as in the present invention, the stilbene compound has an ionization potential value considerably smaller than those materials. The stilbene compound becomes a hole trap site of transferred charge, and a resultant electrophotographic photoconductor has defects of significantly low sensitivity and large residual potential.

Also, diamine compounds effective for suppressing image degradation due to NOx, etc. are disclosed in JP-B No. 4101676 and JP-B No. 3949550. Reduction of sensitivity thereof is relatively small, but it is considered insufficient because it has a problem of decreased resolution due to cyclic fatigue.

Further, an amine compound in which a dialkylamino group is directly bound to a triarylamine structure is disclosed in JP-B No. 3996490. However, similarly to the stilbene compounds, a resultant electrophotographic photoconductor has a defect of significantly low sensitivity and high residual potential.

SUMMARY OF THE INVENTION

The present invention aims at providing: an electrophotographic photoconductor which stably provides a high-quality image by having high durability in long-term repeated use and by suppressing image density decrease or image degradation due to occurrence of image blurring; and an image forming method, an image forming apparatus and a process cartridge using the electrophotographic photoconductor, which require no replacement of the electrophotographic photoconductor, enable high-speed printing or apparatus downsizing due to reduction in photoconductor diameter and further stably provide high-quality image in repeated use.

As a result of extensive studies to solve the problems, the present inventors have found that the problems of image blurring (image deletion) due to the blur generating substance such as oxidizing gas may be solved by incorporating a specific amine compound in a photoconductive layer and completed the present invention.

The amine compound of the present invention as a means for solving the problems is represented by General Formula (I) below.

General Formula (I)

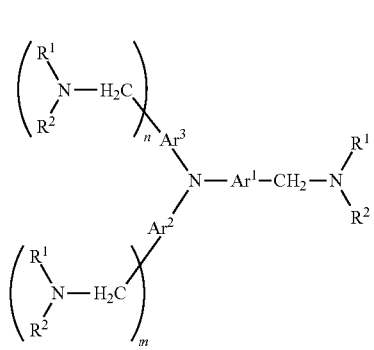

[In General Formula (I), $R^1$ and $R^2$ represent a substituted or unsubstituted alkyl group, a substituted or unsubstituted aralkyl group, or a substituted or unsubstituted aromatic hydrocarbon group, which may be identical or different; m and n are an integer of 1 or 0; $Ar^1$ represents a substituted or unsubstituted aromatic hydrocarbon group; $Ar^2$ and $Ar^3$ represent a substituted or unsubstituted alkyl group, a substituted or unsubstituted aralkyl group, or a substituted or unsubstituted aromatic hydrocarbon group; and $Ar^1$ and $Ar^2$ or $Ar^2$ and $Ar^3$ may bind to each other to form a substituted or unsubstituted heterocyclic group including a nitrogen atom.]

The amine compound of the present invention is preferably represented by any one of General Formulae (1) to (3) below.

General Formula (1)

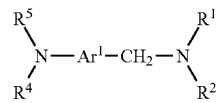

[In General Formula (1), $R^1$ and $R^2$ represent a substituted or unsubstituted alkyl group, a substituted or unsubstituted aralkyl group, or a substituted or unsubstituted aromatic hydrocarbon group, which may be identical or different; $Ar^1$ represents a substituted or unsubstituted aromatic hydrocarbon group; $R^4$ and $R^5$ represent a substituted or unsubstituted alkyl group, a substituted or unsubstituted aralkyl group, or a substituted or unsubstituted aromatic hydrocarbon group; and $Ar^1$ and $R^4$ or $R^4$ and $R^5$ may bind to each other to form a substituted or unsubstituted heterocyclic group including a nitrogen atom.]

General Formula (2)

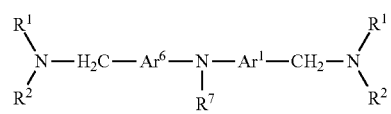

[In General Formula (2), $R^1$, $R^2$ and $R^7$ represent a substituted or unsubstituted alkyl group, a substituted or unsubstituted aralkyl group, or a substituted or unsubstituted aromatic hydrocarbon group, which may be identical or different; $R^1$ and $R^2$ may bind to each other to form a substituted or unsubstituted heterocyclic group including a nitrogen atom; $Ar^1$ and $Ar^6$ represent a substituted or unsubstituted aromatic hydrocarbon group.]

General Formula (3)

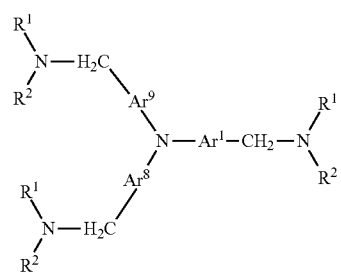

[In General Formula (3), $R^1$ and $R^2$ represent a substituted or unsubstituted alkyl group, a substituted or unsubstituted aralkyl group, or a substituted or unsubstituted aromatic hydrocarbon group, which may be identical or different; $R^1$ and $R^2$ may bind to each other to form a substituted or unsubstituted heterocyclic group including a nitrogen atom; $Ar^1$, $Ar^8$ and $Ar^9$ represent a substituted or unsubstituted aromatic hydrocarbon group.]

According to the present invention, an electrophotographic photoconductor which stably provides high-quality image by having high durability in long-term repeated use and by suppressing image density decrease or image degradation by occurrence of image blurring is provided. Also, by using the photoconductor, extremely superior effects may be exhibited that an image forming method, an image forming apparatus and a process cartridge which require no replacement of the photoconductor, enables high-speed printing or apparatus downsizing due to reduction in photoconductor diameter and further stably provide high-quality image in repeated use are provided.

That is, according to the present invention, by including the amine compound represented by General Formula (I), environmental resistances to repeated use and an oxidizing gas largely improve without sensitivity decrease, and thus an electrophotographic photoconductor which has high durability and provides a high-resolution image over a long period of time may be achieved. In addition, by the present invention, both high durability and high image quality of the electrophotographic photoconductor may be achieved, and the electrophotographic photoconductor which stably provides high-quality image over a long period of time, and an image forming method, an image forming apparatus and a process cartridge which use the same are provided.

Figure 1:
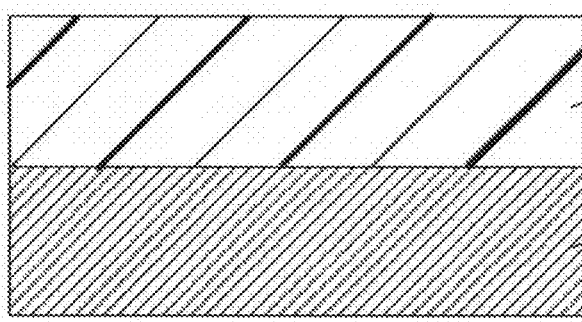
FIG. 1 is a cross-sectional diagram illustrating one example of an electrophotographic photoconductor of the present invention.

DETAILED DESCRIPTION OF THE INVENTION (Amine Compound)

An amine compound of the present invention is represented by General Formula (I) below.

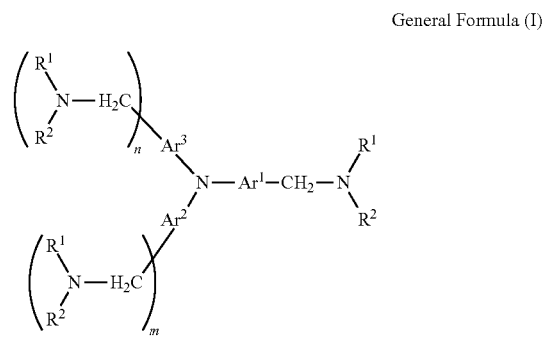

General Formula (I)

[In General Formula (I), $R^1$ and $R^2$ represent a substituted or unsubstituted alkyl group, a substituted or unsubstituted aralkyl group, or a substituted or unsubstituted aromatic hydrocarbon group, which may be identical or different; m and n are an integer of 1 or 0; $Ar^1$ represents a substituted or unsubstituted aromatic hydrocarbon group; $Ar^2$ and $Ar^3$ represent a substituted or unsubstituted alkyl group, a substituted or unsubstituted aralkyl group, or a substituted or unsubstituted aromatic hydrocarbon group; and $Ar^1$ and $Ar^2$ or $Ar^2$ and $Ar^3$ may bind to each other to form a substituted or unsubstituted heterocyclic group including a nitrogen atom.]

The amine compound represented by General Formula (I) is preferably an amine compound represented by any one of General Formulae (1) to (3) below.

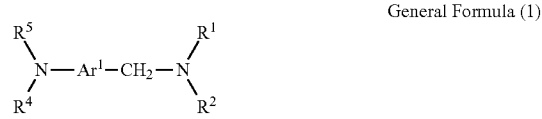

General Formula (1)

[In General Formula (1), $R^1$ and $R^2$ represent a substituted or unsubstituted alkyl group, a substituted or unsubstituted aralkyl group, or a substituted or unsubstituted aromatic hydrocarbon group, which may be identical or different; $Ar^1$ represents a substituted or unsubstituted aromatic hydrocarbon group; $R^4$ and $R^5$ represent a substituted or unsubstituted alkyl group, a substituted or unsubstituted aralkyl group, or a substituted or unsubstituted aromatic hydrocarbon group; and $Ar^1$ and $R^4$ or $R^4$ and $R^5$ may bind to each other to form a substituted or unsubstituted heterocyclic group including a nitrogen atom.]

General Formula (2)

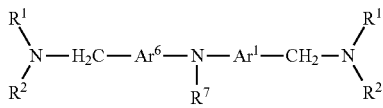

[In General Formula (2), $R^1$, $R^2$ and $R^7$ represent a substituted or unsubstituted alkyl group, a substituted or unsubstituted aralkyl group, or a substituted or unsubstituted aromatic hydrocarbon group, which may be identical or different; $R^1$ and $R^2$ may bind to each other to form a substituted or unsubstituted heterocyclic group including a nitrogen atom; $Ar^1$ and $Ar^6$ represent a substituted or unsubstituted aromatic hydrocarbon group.]

General Formula (3)

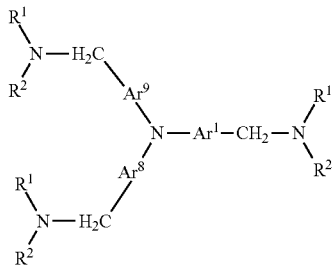

[In General Formula (3), $R^1$ and $R^2$ represent a substituted or unsubstituted alkyl group, a substituted or unsubstituted aralkyl group, or a substituted or unsubstituted aromatic hydrocarbon group, which may be identical or different; $R^1$ and $R^2$ may bind to each other to form a substituted or unsubstituted heterocyclic group including a nitrogen atom; $Ar^1$, $Ar^8$ and $Ar^9$ represent a substituted or unsubstituted aromatic hydrocarbon group.]

The amine compound represented by General Formula (I) is effective for maintaining image quality when a photoconductor is in repeated use. The reason is that, although it is not revealed at the moment, a neutralization effect to the oxidizing gas considered as a causative substance of image blurring is presumed since the alkylamino group included in the chemical structures is a strongly basic group [Shimada, Ikegami, Ricoh Technical Report, Vol. 33, p. 21-26, 2007]. Also, an amino group substituted by an aromatic hydrocarbon ring group is known as a functional group having superior charge transportability [Takahashi et al., *Denshi Shashin Gakkaishi* (Electrophotography), Vol. 25, No. 3, p. 16, 1986]. The amine compound used in the present invention is found to be a compound having high charge transportability since it includes this group. Further, by combining it with other charge transport materials, it has been found that sensitivity and repetition stability, etc. are further enhanced.

Also, the amine compound represented by General Formula (I) in particular is a compound in which a structural site including an alkylamino group effective for maintaining image quality and a structural site including an amino group substituted by an aromatic hydrocarbon ring group having superior charge transportability are bound via a methylene group. Thus, since the amine compound represented by General Formula (I) does not have an interaction having an electrically adverse effect of the stilbene compound including a dialkylamino group disclosed in JP-A No. 60-196768 and JP-B No. 2884353 cited in Description of the Related Art, or the amine compound in which a dialkylamino group is directly bound to a triarylamine structure of JP-B No. 3996490, it is considered that an electrophotographic photoconductor which has high durability in long-term repeated use, suppresses image density decrease or image degradation due to occurrence of image blurring and provides to stably a high-quality image may be provided.

The amine compound represented by General Formula (I) may be manufactured by a method described in an article (A. F. Abdel-Magid et al., J. Org. Chem., Vol. 61, No. 11, p. 3849-3862 (1996)) or a method described in an article (E. R. Burkhardt et al., Tetrahedron. Lett., Vol. 49, No. 35, p. 5152-5155 (2008)). That is, an aldehyde represented by General Formula (15) below and an amine compound represented by General Formula (16) below are subjected to a reaction in the presence of a reducing agent, at a temperature of around −50° C. to 100° C., preferably from a room temperature to a temperature of around 50° C.

General Formula (15)

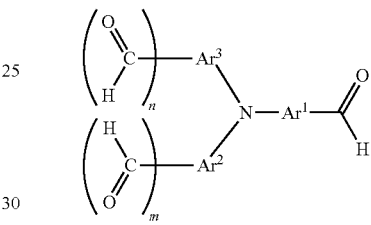

[In General Formula (15), m and n are an integer of 1 or 0; $Ar^1$ represents a substituted or unsubstituted aromatic hydrocarbon group; $Ar^2$ and $Ar^3$ represent a substituted or unsubstituted alkyl group, a substituted or unsubstituted aralkyl group, or a substituted or unsubstituted aromatic hydrocarbon group; $Ar^1$ and $Ar^2$ or $Ar^2$ and $Ar^3$ may bind to each other to form a substituted or unsubstituted heterocyclic group including a nitrogen atom.]

General Formula (16)

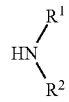

[In General Formula (16), $R^1$ and $R^2$ represent a substituted or unsubstituted alkyl group, a substituted or unsubstituted aralkyl group, or a substituted or unsubstituted aromatic hydrocarbon group, which may be identical or different.]

The diamine compound represented by General Formula (1) may be manufactured by a method described in an article (A. F. Abdel-Magid et al., J. Org. Chem., Vol. 61, No. 11, p. 3849-3862 (1996)) or a method described in an article (E. R. Burkhardt et al., Tetrahedron. Lett., Vol. 49, No. 35, p. 5152-5155 (2008)). That is, an aldehyde represented by General Formula (17) below and an amine compound represented by General Formula (16) below are subjected to a reaction in the presence of a reducing agent, at a temperature of around −50° C. to 100° C., preferably from a room temperature to a temperature of around 50° C.

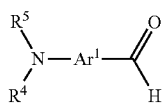

General Formula (17)

[In General Formula (17), $Ar^1$ represents a substituted or unsubstituted aromatic hydrocarbon group; $R^4$ and $R^5$ represent a substituted or unsubstituted alkyl group, a substituted or unsubstituted aralkyl group, or a substituted or unsubstituted aromatic hydrocarbon group; $Ar^1$ and $R^4$, or $R^4$ and $R^5$ may bind to each other to form a substituted or unsubstituted heterocyclic group including a nitrogen atom.]

Similarly, the triamine compound represented by General Formula (2) can be manufactured by reacting the aldehyde represented by General Formula (18) below with the amine compound represented by General Formula (16) above at the same temperature range.

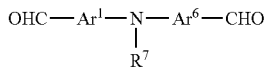

General Formula (18)

[In General Formula (18), $R^7$ represents a substituted or unsubstituted alkyl group, or a substituted or unsubstituted aromatic hydrocarbon group; and $Ar^1$ and $Ar^6$ represent a substituted or unsubstituted aromatic hydrocarbon group.]

Also, the triamine compound represented by General Formula (2) may be easily manufactured by a method described in an article (E. Elceand, A. S. Hay, Polymer, Vol. 37, No. 9, p. 1745 (1996)).

That is, it may be obtained by subjection a dihalide represented by General Formula (2A) below and a secondary amine compound represented by General Formula (2B) below to a reaction in a presence of a reducing agent at a temperature of around −50° C. to 100° C., preferably from a room temperature to around 50° C.

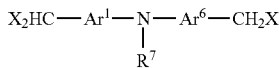

General Formula (2A)

[In General Formula (2A), $R^7$ represents a substituted or unsubstituted alkyl group or a substituted or unsubstituted aromatic hydrocarbon group; $Ar^1$ and $Ar^6$ represent a substituted or unsubstituted aromatic hydrocarbon group; X represents a halogen atom.]

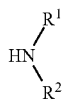

General Formula (2B)

[In General Formula (2B), $R^1$ and $R^2$ represent a substituted or unsubstituted alkyl group or a substituted or unsubstituted aromatic hydrocarbon group, which may be identical or different; $R^1$ and $R^2$ may bind to each other to form a substituted or unsubstituted heterocyclic group including a nitrogen atom.]

Also, the tetramine compound represented by General Formula (3) may be obtained by subjecting an aldehyde represented by General Formula (19) below and an amine compound represented by General Formula (16) to a reaction in a presence of a reducing agent, at a temperature of around −50° C. to 100° C., preferably from a room temperature to a temperature of around 50° C.

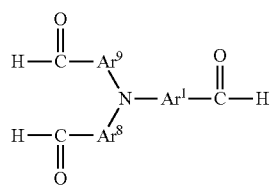

General Formula (19)

[In General Formula (19), $Ar^1$, $Ar^8$ and $Ar^9$ represent a substituted or unsubstituted aromatic hydrocarbon group.]

The reducing agent is not particularly restricted and may be appropriately selected according to purpose. Examples thereof include lithium aluminum hydride, lithium borohydride, sodium borohydride, sodium bis(2-methoxyethoxy) aluminum hydride, sodium cyanoborohydride, sodium triacetoxyborohydride, formic acid, a borane-tetrahydrofuran complex, a borane-N,N-diethylaniline complex, methylsulfide borane, and 5-ethyl-2-methylpyridine borane. Among these, sodium cyanoborohydride, sodium triacetoxyborohydride, and 5-ethyl-2-methylpyridine borane are preferable.

Also, a reaction solvent is not particularly restricted and may be appropriately selected according to purpose. Examples thereof include methanol, ethanol, isopropyl alcohol, acetonitrile, tetrahydrofuran, dichloroethane, dichloromethane, 1,4-dioxane, toluene, xylene, anisole and so on. Also, in order to accelerate the reaction, an acid catalyst such as acetic acid, hydrochloric acid, sulfuric acid, and p-toluene sulfonic acid may be added.

Examples of the alkyl group in the general formulae include a methyl group, an ethyl group, a propyl group, a butyl group, a hexyl group, an undecanyl group and so on. Also, examples of the aralkyl group include a benzyl group, a phenethyl group, a cumyl group, a naphthylmethyl group and so on. Also, examples of the aryl group include a derivative of a monocyclic aromatic ring such as phenyl, tolyl and xylyl, a naphthyl group and so on. Also, examples of the alkylene group include a divalent group that one hydrogen atom is removed from the alkyl group. Also, examples of the arylene group include a divalent group that one hydrogen atom is removed from the aryl group. Also, examples of the aromatic hydrocarbon group include an aromatic ring such as benzene, biphenyl, naphthalene, anthracene, fluorene and pyrene, an aromatic heterocyclic group such as pyridine, quinoline, thiophen, furan, oxazole, oxadiazole, and carbazole and so on.

Also, examples of a substituent thereof include: those exemplified as specific examples of the alkyl group; an alkoxy group such as methoxy group, ethoxy group, propoxy group, and butoxy group; a halogen atom such as fluorine atom, chlorine atom, bromine atom, and iodine atom; the aromatic hydrocarbon group; 2-arylethenyl group; a group of heterocycle such as pyrrolidine, piperidine, and piperazine and so on. Further, when $Ar^2$ and $Ar^3$ bind to each other to form a substituted or unsubstituted heterocyclic group including a nitrogen atom, examples of the heterocyclic group include a fused heterocyclic group in which an aromatic hydrocarbon group is fused to a pyrrolidino group, a piperidino group or a piperazino group and so on.

Hereinafter, preferable examples of compounds represented by General Formula (1), General Formula (2) and General Formula (3) are listed. Here, the present invention is not to be limited by these compounds.

TABLE 1-1

General Formula (1)

$$\begin{array}{c} R^5 \\ \diagdown \\ N-Ar^1-CH_2-N \\ \diagup \\ R^4 \end{array} \begin{array}{c} R^1 \\ \diagup \\ \diagdown \\ R^2 \end{array}$$

| Compound No. | Ar¹ | R⁴ | R⁵ | R¹ | R² |
|---|---|---|---|---|---|
| I-1 | phenylene | phenyl | phenyl | —CH₃ | —CH₃ |
| I-2 | phenylene | phenyl | phenyl | —CH₂CH₃ | —CH₂—phenyl |
| I-3 | phenylene | phenyl | phenyl | —CH₃ | —CH₂—phenyl |
| I-4 | phenylene | tolyl | tolyl | —CH₂—phenyl | —p-tolyl |
| I-5 | phenylene | tolyl | tolyl | —CH₂CH₃ | —CH₂—phenyl |
| I-6 | phenylene | tolyl | tolyl | —CH₂CH₃ | —p-tolyl |
| I-7 | phenylene | tolyl | tolyl | —CH₃ | —p-tolyl |
| I-8 | phenylene | tolyl | tolyl | —CH₂CH₂CH₃ | —p-tolyl |

TABLE 1-1-continued

General Formula (1)

$$\begin{array}{c} R^5 \\ | \\ N-Ar^1-CH_2-N \\ | \\ R^4 \end{array} \begin{array}{c} R^1 \\ \\ R^2 \end{array}$$

| Compound No. | Ar¹ | R⁴ | R⁵ | R¹ | R² |
|---|---|---|---|---|---|
| I-9 | 4-phenylene | 4-methylphenyl | 4-methylphenyl-CH₂ | —CH₂CH₃ | 4-methylbiphenyl |
| I-10 | 4-phenylene | 4-biphenyl | 4-methylphenyl-CH₂ | phenyl | 3-methylphenyl |
| I-11 | 4-phenylene | 4-biphenyl | 4-methylphenyl-CH₂ | phenyl-CH₂ | phenyl-CH₂ |
| I-12 | 4-phenylene | 4-biphenyl | 4-methylphenyl-CH₂ | phenyl-CH₂ | 4-methylphenyl |
| I-13 | 4-phenylene | 4-biphenyl | 4-methylphenyl-CH₂ | phenyl-CH₂ | 4-methylphenyl |
| I-14 | 4-phenylene | 4-biphenyl | 4-methylphenyl-CH₂ | 4-chlorophenyl-CH₂ | 4-methoxyphenyl |
| I-15 | 3-phenylene | 4-biphenyl | 4-methylphenyl-CH₂ | —CH₂CH₃ | 4-methylphenyl |
| I-16 | 4-phenylene | 4-biphenyl | 4-biphenyl | phenyl-CH₂ | phenyl-CH₂ |

TABLE 1-1-continued

General Formula (1)

$$\begin{array}{c} R^5 \\ \diagdown \\ R^4 \end{array} N-Ar^1-CH_2-N \begin{array}{c} R^1 \\ \diagup \\ R^2 \end{array}$$

| Compound No. | Ar¹ | R⁴ | R⁵ | R¹ | R² |
|---|---|---|---|---|---|
| I-17 | 3-methylphenyl | biphenyl | 4-methylbenzyl | —CH₂CH₃ | —CH₂CH₃ |
| I-18 | 2-methylphenyl | 4-methylphenyl | 4-methylphenyl | —CH₂CH₃ | 4-methylphenyl |
| I-19 | 2-methylphenyl | 4-methylphenyl | 4-methylphenyl | benzyl | benzyl |
| I-20 | 4-methylbiphenyl | phenyl | phenyl | —CH₃ | —CH₃ |
| I-21 | 4-methylbiphenyl | phenyl | phenyl | —CH₂CH₃ | benzyl |
| I-22 | 4-methylbiphenyl | phenyl | phenyl | benzyl | benzyl |
| I-23 | 4-methylbiphenyl | phenyl | phenyl | —CH₂CH₃ | 4-methylphenyl |
| I-24 | biphenyl | 4-methylphenyl | 4-methylphenyl | —CH₃ | —CH₃ |

TABLE 1-1-continued

General Formula (1)

$$\begin{array}{c} R^5 \\ \diagdown \\ N-Ar^1-CH_2-N \\ \diagup \\ R^4 \end{array} \begin{array}{c} R^1 \\ \diagup \\ \diagdown \\ R^2 \end{array}$$

| Compound No. | Ar¹ | R⁴ | R⁵ | R¹ | R² |
|---|---|---|---|---|---|
| I-25 | 4,4'-biphenylyl | 4-CH₃-C₆H₄ | 4-CH₃-C₆H₄ | —CH₂CH₃ | —CH₂-C₆H₅ |
| I-26 | 4,4'-biphenylyl | 4-CH₃-C₆H₄ | 4-CH₃-C₆H₄ | —CH₂-C₆H₅ | —CH₂-C₆H₅ |
| I-27 | 4-CH₃-biphenylyl | 4-CH₃-C₆H₄ | 4-CH₃-C₆H₄ | —CH₂CH₃ | 4-CH₃-C₆H₄ |
| I-28 | 4,4'-biphenylyl | 4-CH₃-C₆H₄ | 4-CH₃-C₆H₄ | —CH₂-naphthyl | —CH₂-C₆H₅ |
| I-29 | 4-CH₃-C₆H₄ | 4-CH₃-C₆H₄ | 4-(CH=CH-C₆H₅)-C₆H₄ | —CH₂-C₆H₅ | —CH₂-C₆H₅ |
| I-30 | 3,3'-di-CH₃-biphenylyl | C₆H₅ | C₆H₅ | —CH₂-C₆H₅ | —CH₂-C₆H₅ |
| I-31 | 2,6-dimethyl-naphthyl | C₆H₅ | C₆H₅ | —CH₂CH₃ | 4-CH₃-C₆H₄ |

TABLE 1-1-continued

General Formula (1)

$$R^5\!\!-\!\!N\!\!-\!\!Ar^1\!\!-\!\!CH_2\!\!-\!\!N\!\!-\!\!R^2$$
with $R^1$ and $R^4$ substituents

| Compound No. | Ar¹ | R⁴ | R⁵ | R¹ | R² |
|---|---|---|---|---|---|
| I-32 | 2,6-dimethylnaphthyl | 4-methylphenyl | 4-methylphenyl | —CH₂CH₃ | 4-methylphenyl |
| I-33 | 2,6-dimethylnaphthyl | 4-methylphenyl | 4-methylphenyl | benzyl | benzyl |
| I-34 | 9,10-dimethylanthracenyl | phenyl | phenyl | benzyl | benzyl |
| I-35 | 9,10-dimethylanthracenyl | 4-methylphenyl | 4-methylphenyl | benzyl | benzyl |
| I-36 | 9,9-dimethyl-2,7-dimethylfluorenyl | 4-methylphenyl | 4-methylphenyl | benzyl | benzyl |
| I-37 | 1,4-bis(4-methylphenyl)piperazinyl | phenyl | phenyl | benzyl | benzyl |

TABLE 1-1-continued

General Formula (1)

$$\begin{array}{c} R^5 \\ \diagdown \\ N-Ar^1-CH_2-N \\ \diagup \\ R^4 \end{array} \begin{array}{c} R^1 \\ \diagup \\ \diagdown \\ R^2 \end{array}$$

| Compound No. | Ar¹ | R⁴ | R⁵ | R¹ | R² |
|---|---|---|---|---|---|
| I-38 | (4,4'-piperazine-diyl-diphenyl) | 4-methylphenyl | 4-methylphenyl | -CH₂-phenyl | -CH₂-phenyl |
| I-39 | 4-methylphenyl | phenyl | phenyl | -CH₂CH₃ | 2-methylthiophene |
| I-40 | 4-methylbiphenyl | phenyl | phenyl | -CH₂CH₃ | 5-methyl-2,2'-bithiophene |
| I-41 | 4-methylbiphenyl | phenyl | phenyl | -CH₂CH₂CH₃, CH₃ | 5-methyl-2,2'-bithiophene |
| I-42 | 4-methylphenyl | phenyl | N-carbazolyl | -CH₂-phenyl | -CH₂-phenyl |
| I-43 | 4-methylphenyl | — | methylpyrene | -CH₂-phenyl | -CH₂-phenyl |
| I-44 | 4-methylphenyl | phenyl | 1,4-diphenyl-1,2,3,4-tetrahydroquinoxaline | -CH₂-phenyl | -CH₂-phenyl |

TABLE 1-1-continued

General Formula (1)

$$R^5\!-\!N(Ar^1\!-\!CH_2\!-\!N(R^1)(R^2))(R^4)$$

| Compound No. | Ar¹ | R⁴ | R⁵ | R¹ | R² |
|---|---|---|---|---|---|
| I-45 | 3-carbazolyl (N-Ar³) | — | phenyl | —CH₂—phenyl | —CH₂—phenyl |
| I-46 | 3-carbazolyl (N-Ar³) | — | —CH₂CH₃ | —CH₂—phenyl | —CH₂—phenyl |
| I-47 | 3-carbazolyl (N-Ar³) | — | 4-methylphenyl | —CH₂CH₃ | —CH₂—phenyl |
| I-48 | 4-methylphenyl | —CH₂—phenyl | —CH₂—phenyl | —CH₂CH₃ | —CH₂—phenyl |
| I-49 | 4-methylphenyl | —CH₂—phenyl | —CH₂—phenyl | —CH₂—phenyl | —CH₂—phenyl |

General Formula (2)
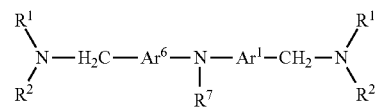
| No. | Ar¹ | Ar⁶ | R⁷ |
|---|---|---|---|
| Table 1-2-1 ||||
| II-1 |  |  | 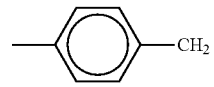 |
| II-2 |  |  | 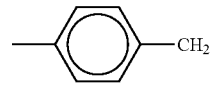 |
| II-3 |  |  | 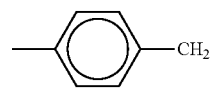 |
| II-4 |  |  | 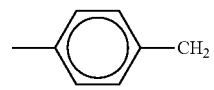 |
| II-5 |  |  | 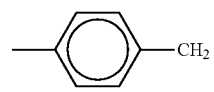 |
| II-6 |  |  | 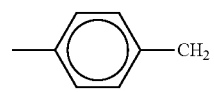 |
| II-7 |  |  | 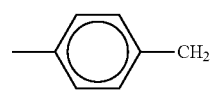 |
| II-8 |  |  | 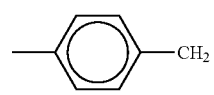 |
| II-9 |  |  | 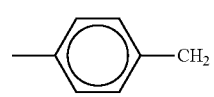 |
| II-10 |  |  | 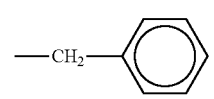 |
| II-11 |  |  | 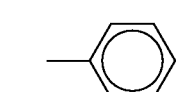 |
| II-12 |  |  | 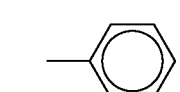 |
| II-13 |  |  | 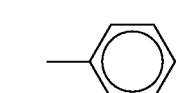 |
| II-14 |  |  | —CH$_2$CH$_3$ |

-continued
General Formula (2)
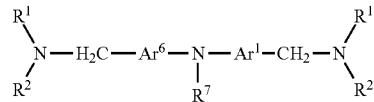
| No. | | | R¹ | R² |
|---|---|---|---|---|
| II-15 | 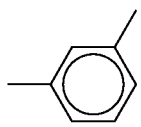 |  | | 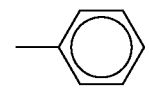 |
| II-1 | | | —CH₃ | —CH₃ |
| II-2 | | | —CH₂CH₃ | —CH₂—⬡ |
| II-3 | | | —CH₂—⬡ | —CH₂—⬡ |
| II-4 | | | —CH₃ | —⬡ |
| II-5 | | | —CH₂CH₃ | —⬡ |
| II-6 | | | —CH₃ | —⬡—CH₃ |
| II-7 | | | —CH₂CH₃ | —⬡—CH₃ |
| II-8 | | | —CH₂CH₂CH₃ | —⬡—CH₃ |
| II-9 | | | —CH₂CH₃ | —⬡—⬡—CH₃ |
| II-10 | | | —CH₂—⬡ | —CH₂—⬡ |
| II-11 | | | —CH₂—⬡ | —⬡—OCH₃ |
| II-12 | | | —CH₂CH₃ | —(pyrenyl) |
| II-13 | | | —CH₂—⬡—Cl | —(pyridyl) |

-continued
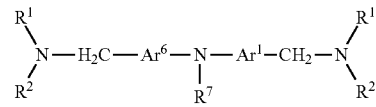 General Formula (2)
| | | | |
|---|---|---|---|
| II-14 | —CH₂CH₃ | | 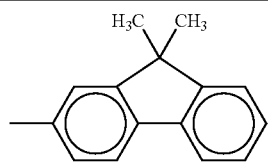 |
| II-15 | —CH₂CH₃ | |  |
Table 1-2-2
| | | | |
|---|---|---|---|
| II-16 | 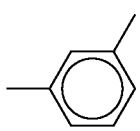 | 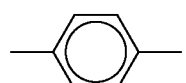 | 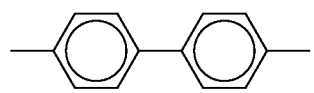 |
| II-17 | 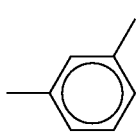 | 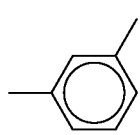 | 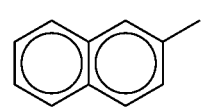 |
| II-18 | 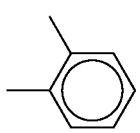 |  | 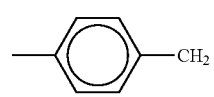 |
| II-19 | 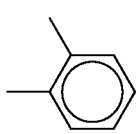 | 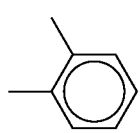 |  |
| II-20 | 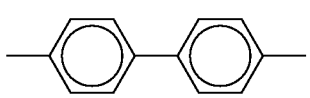 | 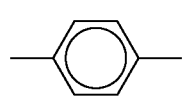 | 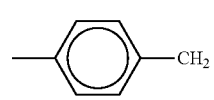 |
| II-21 | 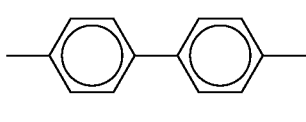 | 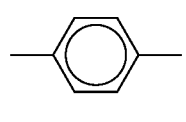 | 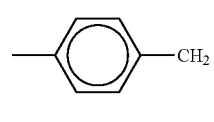 |
| II-22 | 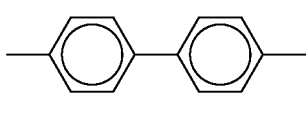 | 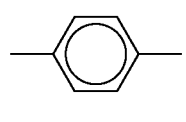 | 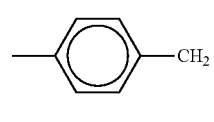 |
| II-23 | 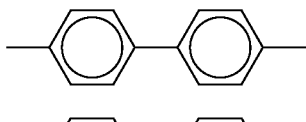 | 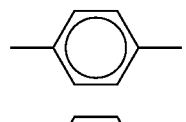 | 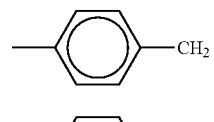 |
| II-24 | 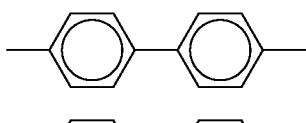 | 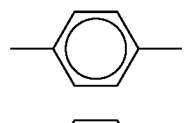 | 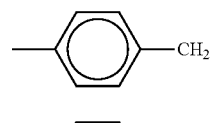 |
| II-25 | 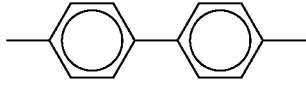 | 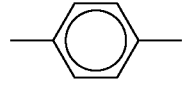 | 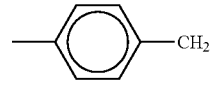 |

-continued
General Formula (2)
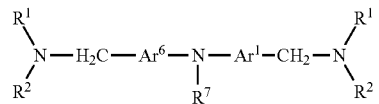
| No. | | | |
|---|---|---|---|
| II-26 | 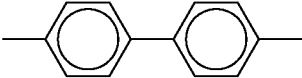 | 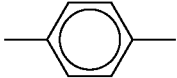 | 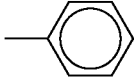 |
| II-27 | 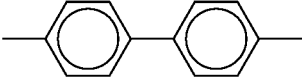 | 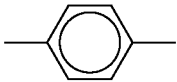 | 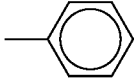 |
| II-28 | 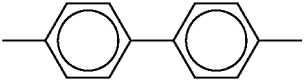 | 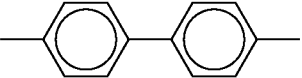 | 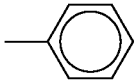 |
| II-29 | 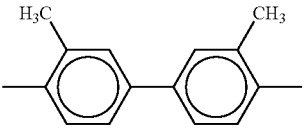 | 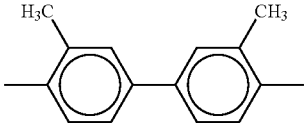 | 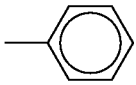 |
| II-30 | 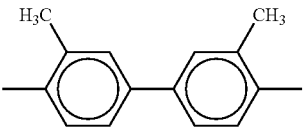 | 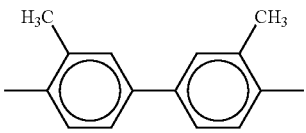 | 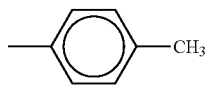 |
| No. | $R^1$ | $R^2$ |
|---|---|---|
| II-16 | 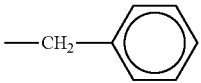 | 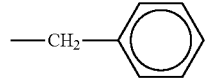 |
| II-17 | 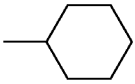 | 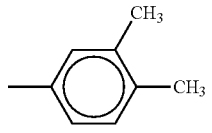 |
| II-18 | —CH$_2$CH$_3$ | 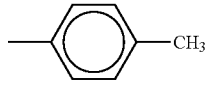 |
| II-19 | —CH$_3$ | 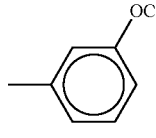 |
| II-20 | —CH$_3$ | —CH$_3$ |
| II-21 | —CH$_2$CH$_3$ | 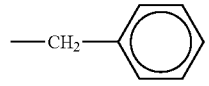 |
| II-22 | 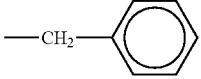 | 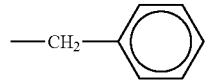 |
| II-23 | —CH$_2$CH$_3$ | 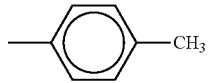 |

-continued
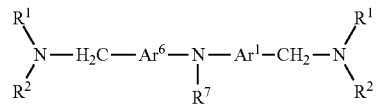
General Formula (2)
| | | | |
|---|---|---|---|
| II-24 | 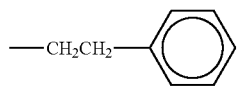 | | 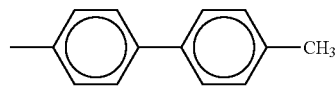 |
| II-25 | —CH₃ | | 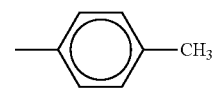 |
| II-26 | —CH₂CH₃ | | 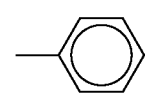 |
| II-27 | 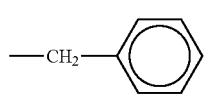 | | 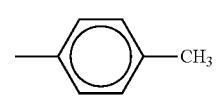 |
| II-28 | 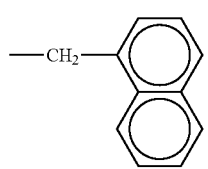 | | 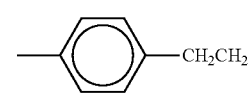 |
| II-29 | —CH₂CH₃ | | 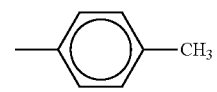 |
| II-30 | 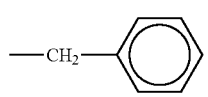 | | 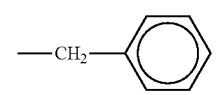 |
Table 1-2-3
| | | | |
|---|---|---|---|
| II-31 | 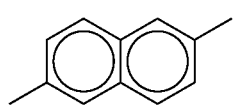 | 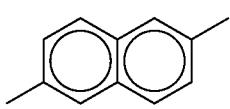 | 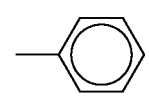 |
| II-32 | 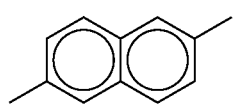 | 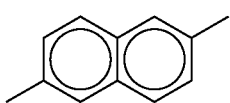 | 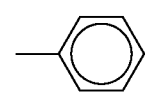 |
| II-33 | 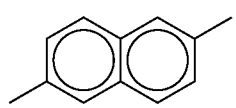 | 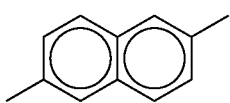 | 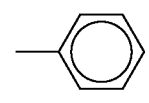 |
| II-34 | 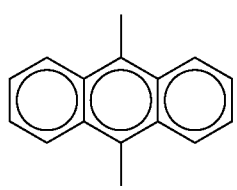 | 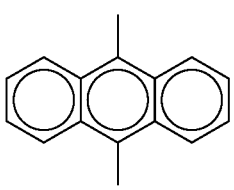 | 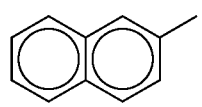 |

-continued
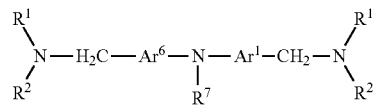
General Formula (2)
| No. | | | |
|---|---|---|---|
| II-35 | | | |
| II-36 | | | |
| II-37 | | | |
| II-38 | | | |
| II-39 | | | |
| II-40 | | | |
| II-41 | | | |
| II-42 | | | |
| II-43 | | | |
| No. | R¹ | R² |
|---|---|---|
| II-31 | —CH₂CH₃ | |
| II-32 | —CH₃ | |
| II-33 | | |

General Formula (2)
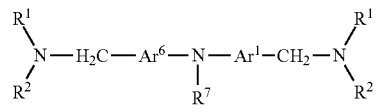
| | | |
|---|---|---|
| II-34 | —CH₂CH₃ |  |
| II-35 | —CH₃ | 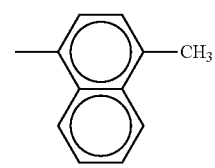 |
| II-36 | —CH₂CH₃ | 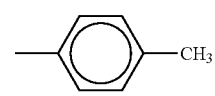 |
| II-37 | —CH₂CH₃ | 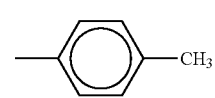 |
| II-38 | —CH₂CH₃ | 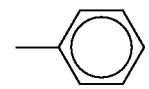 |
| II-39 | —CH₂CH₃ | 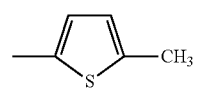 |
| II-40 | —CH₂CH₂CH₃<br>\|<br>CH₃ | 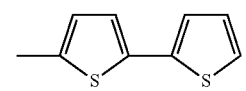 |
| II-41 | | 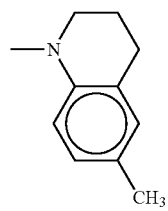 |
| II-42 | | 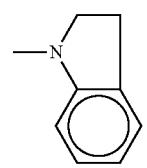 |
| II-43 | | 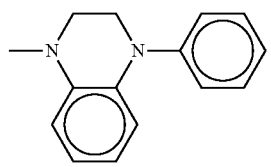 |

General Formula (3)
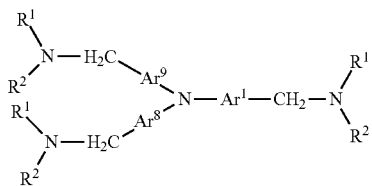
| No. | Ar¹ | Ar⁸ | Ar⁹ |
|---|---|---|---|
| | | Table 1-3-1 | |
| III-1 | -C₆H₄- | -C₆H₄- | -C₆H₄- |
| III-2 | -C₆H₄- | -C₆H₄- | -C₆H₄- |
| III-3 | -C₆H₄- | -C₆H₄- | -C₆H₄- |
| III-4 | -C₆H₄- | -C₆H₄- | -C₆H₄- |
| III-5 | -C₆H₄- | -C₆H₄- | -C₆H₄- |
| III-6 | -C₆H₄- | -C₆H₄- | -C₆H₄- |
| III-7 | -C₆H₄- | -C₆H₄- | -C₆H₄- |
| III-8 | -C₆H₄- | -C₆H₄- | -C₆H₄- |
| III-9 | -C₆H₄- | -C₆H₄- | -C₆H₄- |
| III-10 | -C₆H₄- | -C₆H₄- | -C₆H₄- |
| III-11 | -C₆H₄- | -C₆H₄- | -C₆H₄- |
| III-12 | -C₆H₄- | -C₆H₄- | -C₆H₄- |
| III-13 | -C₆H₄- | -C₆H₄- | -C₆H₄- |

-continued
General Formula (3)
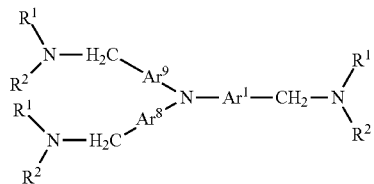
| No. | | R¹ | R² |
|---|---|---|---|
| III-14 | | | |
| III-15 | | | |
| III-1 | | —CH₃ | —CH₃ |
| III-2 | | —CH₂CH₃ | —CH₂—(phenyl) |
| III-3 | | —(p-tolyl) | —CH₂—(phenyl) |
| III-4 | | —CH₃ | —(p-tolyl) |
| III-5 | | —CH₂CH₃ | —(p-tolyl) |
| III-6 | | —CH₃ | —(C₆H₄)—CH₃ |
| III-7 | | —CH₂CH₃ | —(C₆H₄)—CH₃ |
| III-8 | | —CH₂CH₂CH₃ | —(C₆H₄)—CH₃ |
| III-9 | | —CH₂CH₃ | —(C₆H₄)—(C₆H₄)—CH₃ |
| III-10 | | —CH₂—(phenyl) | —CH₂—(phenyl) |
| III-11 | | —CH₂—(phenyl) | —(C₆H₄)—OCH₃ |

-continued
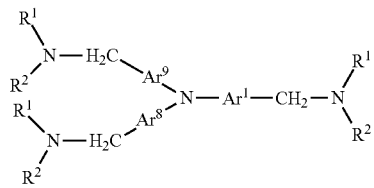
General Formula (3)
| | | |
|---|---|---|
| III-12 | —CH₂CH₃ | 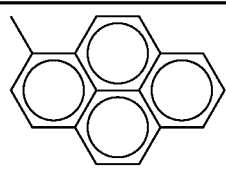 |
| III-13 | 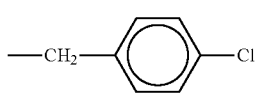 | 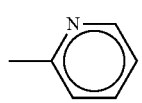 |
| III-14 | —CH₂CH₃ | 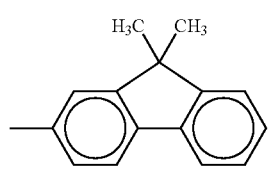 |
| III-15 | —CH₂CH₃ | 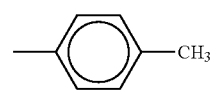 |
Table 1-3-2
| | | | |
|---|---|---|---|
| III-16 | 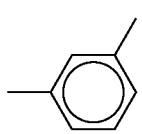 | 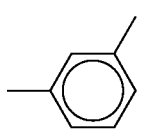 | 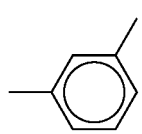 |
| III-17 | 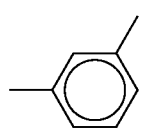 | 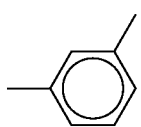 | 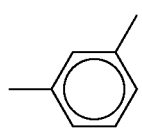 |
| III-18 | 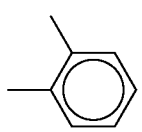 | 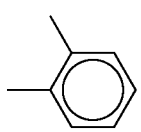 | 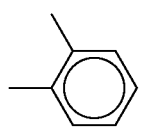 |
| III-19 | 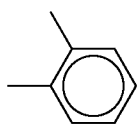 | 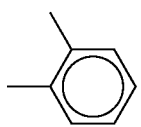 | 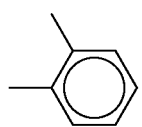 |
| III-20 | 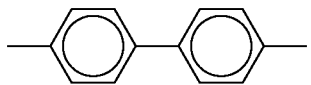 |  | 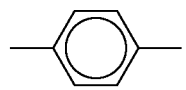 |
| III-21 | 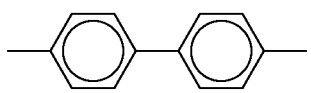 | 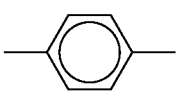 | 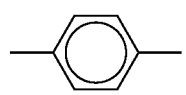 |
| III-22 | 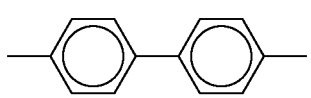 | 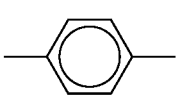 | 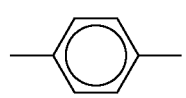 |

-continued
General Formula (3)
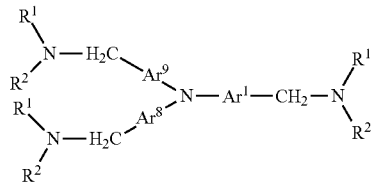
| No. | | | |
|---|---|---|---|
| III-23 | 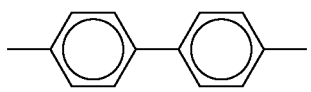 |  |  |
| III-24 | 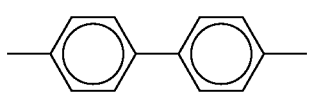 |  | 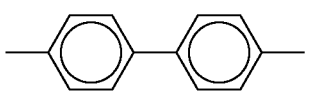 |
| III-25 | 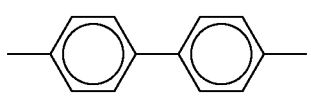 |  | 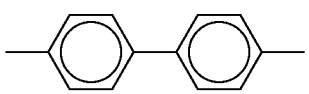 |
| III-26 | 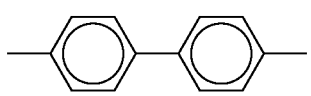 |  | 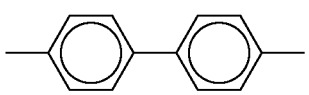 |
| III-27 | 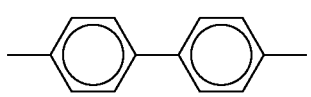 |  | 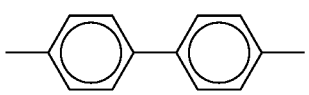 |
| III-28 | 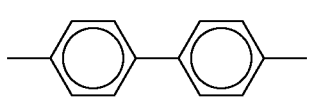 | 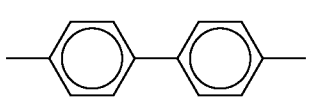 | 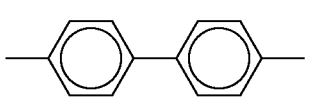 |
| III-29 | 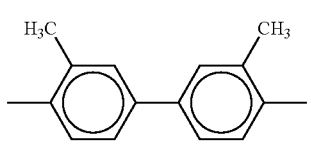 | 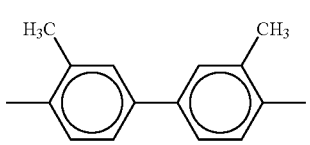 | 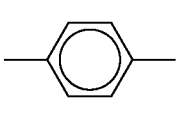 |
| III-30 | 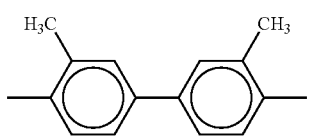 | 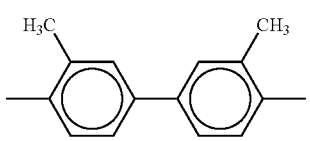 | 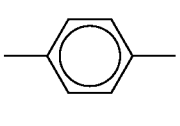 |
| No. | $R^1$ | $R^2$ |
|---|---|---|
| III-16 | 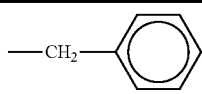 | 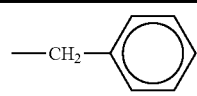 |
| III-17 | 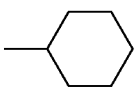 | 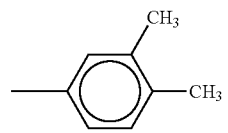 |
| III-18 |  —CH$_2$CH$_3$ | 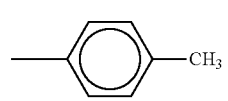 |
| III-19 | 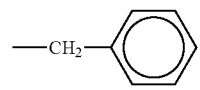 | 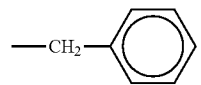 |
| III-20 | —CH$_3$ | —CH$_3$ |

General Formula (3)
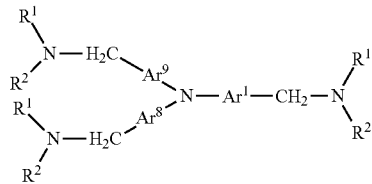
| | | | |
|---|---|---|---|
| III-21 | | —CH₂CH₃ | —CH₂—⟨Ph⟩ |
| III-22 | | —CH₂—⟨Ph⟩ | —CH₂—⟨Ph⟩ |
| III-23 | | —CH₂CH₃ | —⟨Ph⟩—CH₃ |
| III-24 | | —CH₂CH₂—⟨Ph⟩ | —⟨Ph⟩—⟨Ph⟩—CH₃ |
| III-25 | | —CH₃ | —⟨Ph⟩—CH₃ |
| III-26 | | —CH₂CH₃ | —⟨Ph⟩ |
| III-27 | | —CH₂—⟨Ph⟩ | —⟨Ph⟩—CH₃ |
| III-28 | | —CH₂—⟨Ph⟩ | —CH₂—⟨Ph⟩ |
| III-29 | | —CH₂CH₃ | —⟨Ph⟩—CH₃ |
| III-30 | | —CH₂—⟨Ph⟩ | —CH₂—⟨Ph⟩ |
Table 1-3-3
| | | | |
|---|---|---|---|
| III-31 | ⟨naphthyl⟩ | ⟨naphthyl⟩ | ⟨phenyl⟩ |
| III-32 | ⟨naphthyl⟩ | ⟨naphthyl⟩ | ⟨phenyl⟩ |
| III-33 | ⟨naphthyl⟩ | ⟨naphthyl⟩ | ⟨phenyl⟩ |

-continued
General Formula (3)
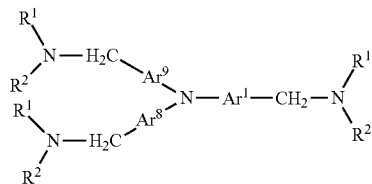
| | | | |
|---|---|---|---|
| III-34 | 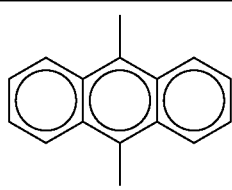 | 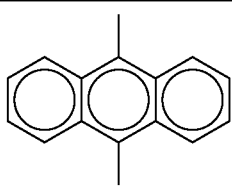 |  |
| III-35 | 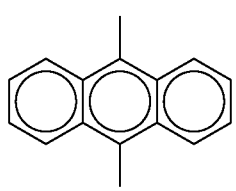 | 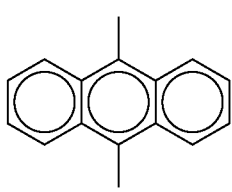 | 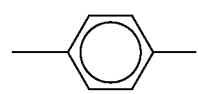 |
| III-36 | 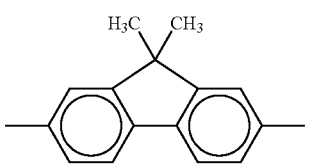 | 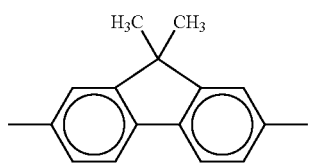 | 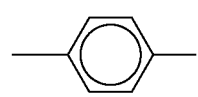 |
| III-37 | 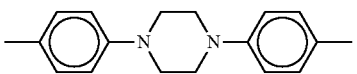 |  | 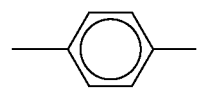 |
| III-38 | 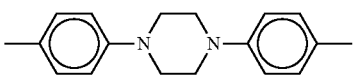 | 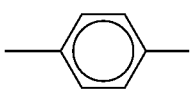 | 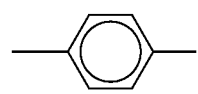 |
| III-39 | 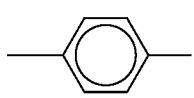 | 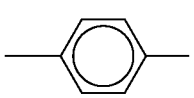 | 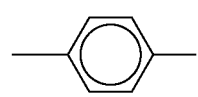 |
| III-40 | 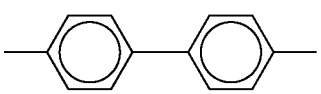 | 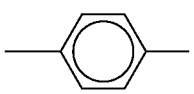 |  |
| III-41 | 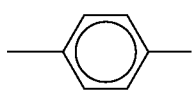 | 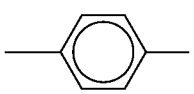 | 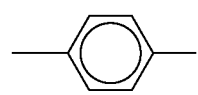 |
| III-42 | 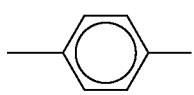 | 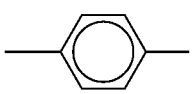 | 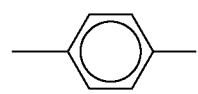 |
| III-43 | 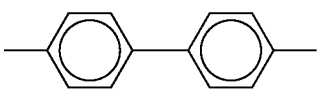 | 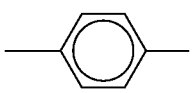 | 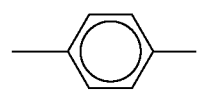 |
| No. | $R^1$ | $R^2$ |
|---|---|---|
| III-31 | —CH$_2$CH$_3$ |  |

General Formula (3)
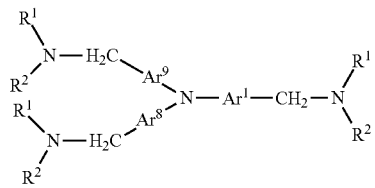
| | | |
|---|---|---|
| III-32 | —CH₃ | 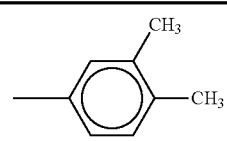 |
| III-33 | 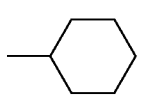 | 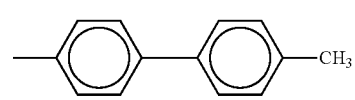 |
| III-34 | —CH₂CH₃ |  |
| III-35 | —CH₃ | 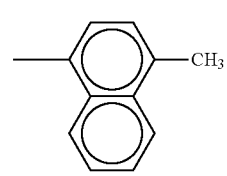 |
| III-36 | —CH₂CH₃ |  |
| III-37 | —CH₂CH₃ | 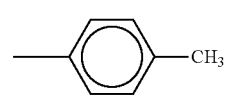 |
| III-38 | —CH₂CH₃ | 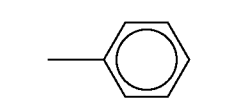 |
| III-39 | —CH₂CH₃ | 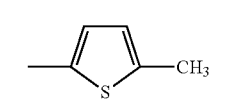 |
| III-40 | —CH₂CH₂CH₃ with CH₃ | 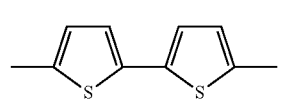 |
| III-41 | | 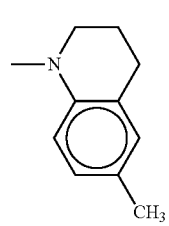 |
| III-42 | | 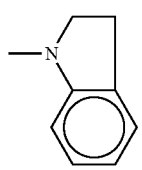 |

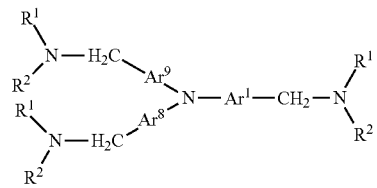
General Formula (3)

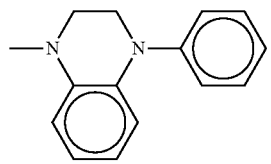
III-43

The amine compound of the present invention represented by General Formula (I) is not only useful as a photoconductive material in an electrophotographic photoconductor but also favorably used as an electronic device in an electronics field such as solar cells and optical discs.

(Electrophotographic Photoconductor)

An electrophotographic photoconductor of the present invention includes a substrate and at least a photoconductive layer on the substrate, preferably includes a protective layer as an outermost surface, and further includes other layers according to necessity.

Next, a layer configuration of the electrophotographic photoconductor of the present invention is explained based on FIG. 1 to FIG. 5. Here, FIG. 1 to FIG. 5 are cross-sectional diagrams illustrating examples of electrophotographic photoconductor of the present invention.

In a configuration of FIG. 1, a photoconductive layer 33, which is mainly composed of a charge generation material and a charge transport material, is disposed on an electrically conductive substrate 31. In this case, the amine compound of the present invention represented by General Formula (I) is included in the photoconductive layer 33.

Figure 2:
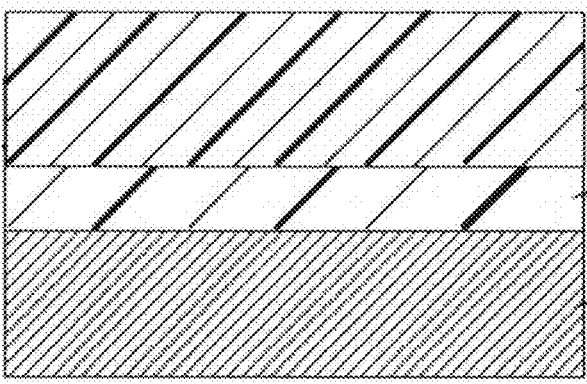
FIG. 2 is a cross-sectional diagram illustrating another example of an electrophotographic photoconductor of the present invention.

In a configuration of FIG. 2, a charge generation layer 35 mainly composed of a charge generation material and a charge transport layer 37 mainly composed of a charge transport material are laminated on an electrically conductive substrate 31.

Figure 3:
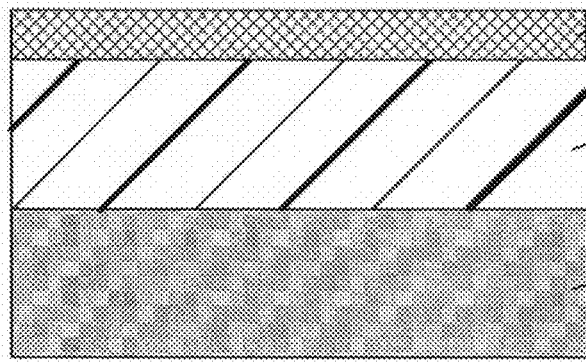
FIG. 3 is a cross-sectional diagram illustrating another example of an electrophotographic photoconductor of the present invention.

In a configuration of FIG. 3, a photoconductive layer 33 mainly composed of a charge generation material and a charge transport material is disposed on an electrically conductive substrate 31, and a protective layer 39 is disposed further on a surface of the photoconductive layer. In this case, the amine compound of the present invention represented by General Formula (I) may be included in the protective layer 39.

Figure 4:
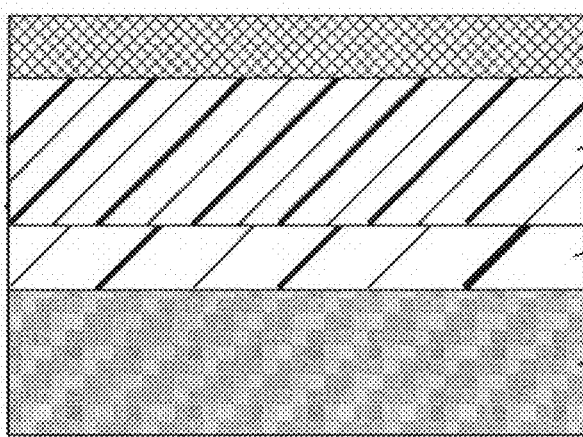
FIG. 4 is a cross-sectional diagram illustrating another example of an electrophotographic photoconductor of the present invention.

In a configuration of FIG. 4, a charge generation layer 35 mainly composed of a charge generation material and a charge transport layer 37 mainly composed of a charge transport material are laminated on an electrically conductive substrate 31, and a protective layer 39 is disposed further on the charge transport layer. In this case, the amine compound of the present invention represented by General Formula (I) may be included in the protective layer 39.

Figure 5:
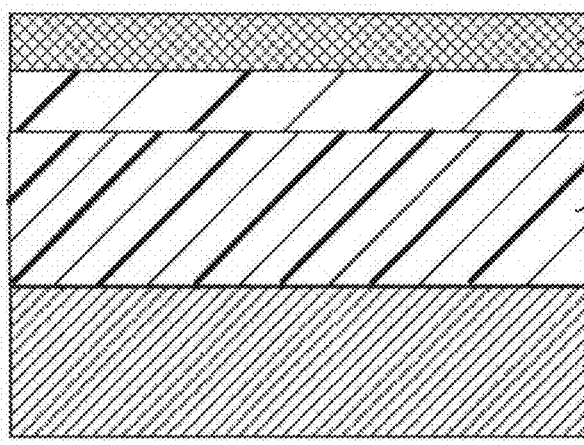
FIG. 5 is a cross-sectional diagram illustrating another example of an electrophotographic photoconductor of the present invention.

In a configuration of FIG. 5, a charge transport layer 37 mainly composed of a charge transport material and a charge generation layer 35 mainly composed of a charge generation material are laminated on an electrically conductive substrate 31, and a protective layer 39 is disposed further on the charge generation layer. In this case, the amine compound of the present invention represented by General Formula (I) may be included in the protective layer 39.

<Electrically Conductive Substrate>

As the electrically conductive substrate which constitutes the photoconductor of the present invention, an electrically conductive material having a volume resistivity of $10^{10}$ Ω·cm or less may be used. Examples thereof include: film-shaped or cylindrical plastic or paper coated with a metal such as aluminum, nickel, chromium, nichrome, copper, gold, silver, and platinum or a metal oxide such as tin oxide and indium oxide by vapor deposition or sputtering; a plate of aluminum, aluminum alloy, nickel, or stainless steel; and a tube obtained by forming a base tube from the plate by methods such as extrusion and drawing, followed by surface treatment such as cutting, super finishing and polishing. Also, an endless nickel belt and an endless stainless-steel belt disclosed in JP-A No. 52-36016 may also be used as the electrically conductive substrate 31.

Besides this, an electrically conductive layer obtained by dispersing an electrically conductive powder in an appropriate binder resin and coating the dispersion on the substrate may be used as the electrically conductive substrate 31. Examples of the electrically conductive powder include: metal powder such as carbon black, acetylene black, aluminum, nickel, iron, nichrome, copper, zinc, and silver; a metal oxide powder such as electrically conductive tin oxide and ITO; and so on.

The binder resin is not particularly restricted and may be appropriately selected according to purpose. Examples thereof include polystyrene, a styrene-acrylonitrile copolymer, a styrene-butadiene copolymer, a styrene-maleic anhydride copolymer, polyester, polyvinyl chloride, a vinyl acetate-vinyl chloride copolymer, polyvinyl acetate, polyvinylidene chloride, a polyarylate resin, a phenoxy resin, polycarbonate, a cellulose acetate resin, an ethylcellulose resin, polyvinyl butyral, polyvinyl formal, polyvinyltoluene, poly-N-vinylcarbazole, an acrylic resin, a silicone resin, an epoxy resin, a melamine resin, a urethane resin, a phenolic resin, an alkyd resin and so on.

The electrically conductive layer may be disposed by dispersing the electrically conductive powder and the binder resin in an appropriate solvent such as tetrahydrofuran, dichloromethane, methyl ethyl ketone, and toluene and coating the dispersion.

Further, an electrically conductive layer may be formed by disposing a heat-shrinkable tube that the electrically conductive powder is included in a material such as polyvinyl chloride, polypropylene, polyester, polystyrene, polyvinylidene chloride, polyethylene, chlorinated rubber and TEFLON (registered trademark) on an appropriate cylindrical substrate, which may be favorably used as the electrically conductive substrate.

<Photoconductive Layer>

Next, the photoconductive layer which constitutes the electrophotographic photoconductor of the present invention is explained. The photoconductive layer may be a single layer or a multilayer, but for convenience of explanation, a configuration of a charge generation layer and a charge transport layer is described first. Here, in the case of the photoconductive layer constituted by the charge generation layer and the charge transport layer, the amine compound of the present invention represented by General Formula (I) is preferably included in the charge transport layer.

<<Charge Generating Layer>>

The charge generation layer constituting the photoconductive layer is a layer mainly composed of a charge generation material.

The charge generation material is not particularly restricted and may be appropriately selected according to purpose. Examples thereof include: azo pigments such as C.I. Pigment Blue 25 (Color Index CI-21180), C.I. Pigment Red 41 (CI 21200), C.I. Acid Red 52 (CI 45100), C. I. Basic Red 3 (CI 45210), azo pigments having an carbazole skeleton (described in JP-A No. 53-95033), azo pigments having a distyrylbenzene skeleton (JP-A No. 53-133445), azo pigments having a triphenylamine skeleton (described in (JP-A No. 53-132347), azo pigments having a dibenzothiophene skeleton (described in JP-A No. 54-21728), azo pigments having an oxadiazole skeleton (described in JP-A No. 54-12742), azo pigments having a fluorenone skeleton (described in JP-A No. 54-22834), azo pigments having a bis-stilbene skeleton (described in JP-A No. 54-17733), azo pigments having a distyryloxadiazole skeleton (described in JP-A No. 54-2129), azo pigments having a distyrylcarbazole skeleton (described in JP-A No. 54-14967), and azo pigments having a benzanthrone skeleton; phthalocyanine pigments such as C.I. Pigment Blue 16 (CI 74100), y-type oxotitanium phthalocyanine (JP-A No. 64-17066), A(β)-type oxotitanium phthalocyanine, B(α)-type oxotitanium phthalocyanine, I-type oxotitanium phthalocyanine (described in JP-A No. 11-21466), II-type gallium phthalocyanine chloride (Iijima et al., The Chemical Society of Japan 67th Spring Annual Meeting, 1B4, 04 (1994)), V-type gallium phthalocyanine hydroxide (Daimon et al., The Chemical Society of Japan 67th Spring Annual Meeting, 1B4, 05 (1994)), and X-type metal-free phthalocyanine (U.S. Pat. No. 3,816,118); indigo pigments such as C.I. Vat Brown 5 (CI 73410) and C.I. Vat Dye (CI 73030); and perylene pigments such as Algo Scarlet B (manufactured by Bayer), Indanthrene Scarlet R (manufactured by Bayer). These may be used alone or in combination of two or more.

The charge generation layer is formed by dissolving a charge generation material in an appropriate solvent along with a binder resin according to necessity using a ball mill, an attritor, a sand mill or an ultrasonic wave, and applying this on the electrically conductive substrate followed by drying.

The binder resin used for the charge generation layer according to necessity is not particularly restricted and may be appropriately selected according to purpose. Examples thereof include polyamide, polyurethane, an epoxy resin, polyketone, polycarbonate, a silicone resin, an acrylic resin, polyvinyl butyral, polyvinyl formal, polyvinyl ketone, polystyrene, polysulfone, poly-N-vinylcarbazole, polyacrylamide, polyvinyl benzole, polyester, a phenoxy resin, a vinyl acetate-vinyl chloride copolymer, polyvinyl acetate, polyphenylene oxide, polyamide, polyvinyl pyridine, a cellulose-based resin, casein, polyvinyl alcohol, polyvinyl pyrrolidone and so on. These may be used alone or in combination of two or more.

A content of the binder resin is not particularly restricted and may be appropriately selected according to purpose. Nonetheless, it is preferably 0 parts by mass to 500 parts by mass, and more preferably 10 parts by mass to 300 parts by mass with respect to 100 parts by mass of the charge generation material. Here, addition of the binder resin may be before or after the dispersion.

The solvent used for forming the charge generation layer is not particularly restricted and may be appropriately selected according to purpose. Examples thereof include isopropanol, acetone, methyl ethyl ketone, cyclohexanone, tetrahydrofuran, dioxane, ethyl cellosolve, ethyl acetate, methyl acetate, dichloromethane, dichloroethane, monochlorobenzene, cyclohexane, toluene, xylene, ligroin and so on. These may be used alone or in combination of two or more. Among these, ketone solvents, ester solvents, and ether solvents are particularly preferable.

The charge generation layer coating solution is mainly composed of the charge generation material, the solvent and the binder resin, and any additive such as sensitizer, dispersant, surfactant and silicone oil may further be include therein.

A coating method of the coating solution for forming the charge generation layer is not particularly restricted and may be appropriately selected according to purpose. Examples thereof include a dip-coating method, a spray-coating method, a bead-coating method, a nozzle-coating method, a spinner-coating method, and a ring-coating method.

A thickness of the charge generation layer 35 is not particularly restricted and may be appropriately selected according to purpose. Nonetheless, it is preferably 0.10 µm to 5 µm, and more preferably 0.1 µm to 2 µm.

<<Charge Transport Layer>>

The charge transport layer is a layer mainly composed of a charge transport material, and it includes the amine compound of the present invention along with the charge transport material.

The charge transport material is divided into a hole transport material, an electron transport material and a charge transport polymers, which are explained below.

The hole transport material which constitutes the charge transport layer is not particularly restricted and may be appropriately selected according to purpose. Examples thereof include poly-N-carbazole and derivatives thereof, poly-γ-carbazolylethylglutamate and derivatives thereof, pyrene-formaldehyde condensate and derivatives thereof, polyvinyl pyrene, polyvinyl phenanthrene, oxazole derivatives, imidazole derivative, triphenylamine derivative, and compounds represented by General Formulae (20) to (37) below.

General Formula (20)

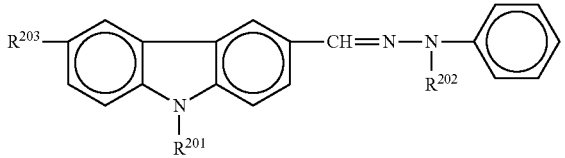

[In General Formula (20), $R^{201}$ represents a methyl group, an ethyl group, a 2-hydroxyethyl group or a 2-chloroethyl group; $R^{202}$ represents a methyl group, an ethyl group, a benzyl group or a phenyl group; and $R^{203}$ represents a hydrogen atom, a chlorine atom, a bromine atom, an alkyl group having 1 to 4 carbon atoms, an alkoxy group having 1 to 4 carbon atoms, a dialkylamino group or a nitro group.]

Examples of the compounds represented by General Formula (20) include 9-ethylcarbazole-3-aldehyde-1-methyl-1-phenylhydrazone, 9-ethylcarbazole-3-aldehyde-1-benzyl-1-phenylhydrazone, 9-ethylcarbazole-3-aldehyde-1,1-diphenylhydrazon and so on.

General Formula (21)

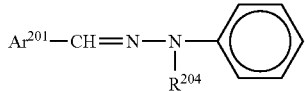

[In General Formula (21), $Ar^{201}$ represents a naphthalene ring, an anthracene ring, a pyrene ring and a substitution product thereof, a pyridine ring, a furan ring, or a thiophen ring; $R^{204}$ represents an alkyl group, a phenyl group, or a benzyl group.]

Examples of the compounds represented by General Formula (21) include 4-diethylaminostyryl-β-aldehyde-1-methyl-1-phenylhydrazone, 4-methoxynaphthalene-1-aldehyde-1-benzyl-1-phenylhydrazone and so on.

General Formula (22)

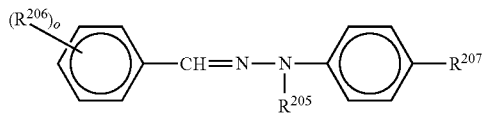

[In General Formula (22), $R^{205}$ represents an alkyl group, a benzyl group, a phenyl group or a naphthyl group; $R^{206}$ represents a hydrogen atom, an alkyl group having 1 to 3 carbon atoms, an alkoxy group having 1 to 3 carbon atoms, a dialkylamino group, a diaralkylamino group, or a substituted or unsubstituted diarylamino group; o represents an integer of 1 to 4, and when o is 2 or greater, $R^{206}$ is identical or different; $R^{207}$ represents a hydrogen atom or a methoxy group.]

Examples of the compounds represented by general formula (22) include 4-methoxybenzaldehyde-1-methyl-1-phenylhydrazone, 2,4-dimethoxybenzaldehyde-1-benzyl-1-phenylhydrazone, 4-diethylaminobenzaldehyde-1,1-diphenylhydrazon, 4-methoxybenzaldehyde-1-(4-methoxy)phenylhydrazone, 4-diphenylaminobenzaldehyde-1-benzyl-1-phenylhydrazone, 4-dibenzylaminobenzaldehyde-1,1-diphenylhydrazon and so on.

General Formula (23)

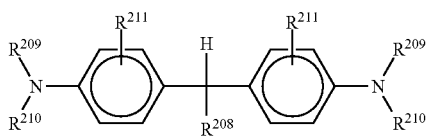

[In General Formula (23), $R^{208}$ represents an alkyl group having 1 to 11 carbon atoms, a substituted or unsubstituted phenyl group or heterocyclic group; $R^{209}$ and $R^{210}$ may be respectively identical or different, representing a hydrogen atom, an alkyl group having 1 to 4 carbon atoms, a hydroxyalkyl group, a chloroalkyl group or a substituted or unsubstituted aralkyl group, and also, $R^{209}$ and $R^{210}$ may bind to each other to form a heterocycle including a nitrogen atom; $R^{211}$ may be identical or different, representing a hydrogen atom, an alkyl group having 1 to 4 carbon atoms, an alkoxy group or a halogen atom.]

Examples of the compounds represented by General Formula (23) include 1,1-bis(4-dibenzylaminophenyl)propane, tris(4-diethylaminophenyl)methane, 2,2'-dimethyl-4,4'-bis(diethylamino)-triphenylmethane and so on.

General Formula (24)

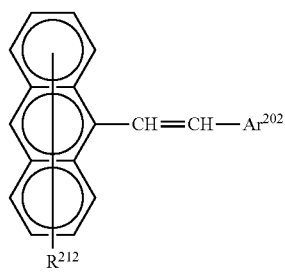

[In General Formula (24), $R^{212}$ represents a hydrogen atom or a halogen atom; $Ar^{202}$ represents a substituted or unsubstituted phenyl group, naphthyl group, anthryl group or carbazolyl group.]

Examples of the compounds represented by General Formula (24) include 9-(4-diethylaminostyryl)anthracene, 9-bromo-10-(4-diethylaminostyryl)anthracene and so on.

General Formula (25)

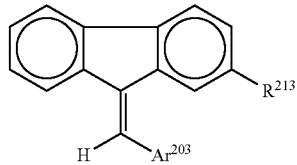

[In General Formula (25), $R^{213}$ represents a hydrogen atom, a halogen atom, a cyano group, an alkoxy group having 1 to 4 carbon atoms or an alkyl group having 1 to 4 carbon atoms; $Ar^{203}$ represents General Formula (25A) or General Formula (25B) below.

General Formula (25A)

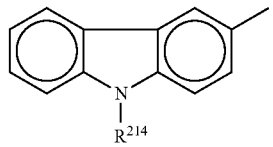

General Formula (25B)

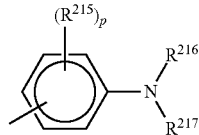

In Formula (25A), $R^{214}$ represents an alkyl group having 1 to 4 carbon atoms. In Formula (25B), $R^{215}$ represents a hydrogen atom, a halogen atom, an alkyl group having 1 to 4 carbon atoms, an alkoxy group having 1 to 4 carbon atoms, or a dialkylamino group; p is 1 or 2, and when p is 2, $R^{215}$ may be identical or different; $R^{216}$ and $R^{217}$ represent a hydrogen atom, a substituted or unsubstituted alkyl group having 1 to 4 carbon atoms, or a substituted or unsubstituted benzyl group.]

Examples of the compounds represented by General Formula (25) include 9-(4-dimethylaminobenzylidene)fluorene, 3-(9-fluorenylidene)-9-ethylcarbazole and so on.

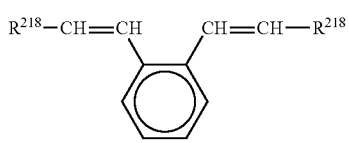

General Formula (26)

[In General Formula (26), $R^{218}$ represents: a carbazolyl group, a pyridyl group, a thienyl group, an indolyl group, or a furyl group; or a phenyl group, a styryl group, a naphthyl group, or an anthryl group, each of which is substituted or unsubstituted, where a substituent thereof is any one group selected from the group consisting of a dialkylamino group, an alkyl group, an alkoxy group, a carboxyl group or an ester thereof, a halogen atom, a cyano group, an aralkylamino group, an N-alkyl-N-aralkylamino group, an amino group, a nitro group and an acetylamino group.]

Examples of the compounds represented by General Formula (26) include 1,2-bis(4-diethylaminostyryl)benzene, 1,2-bis(2,4-dimethoxystyryl)benzene and so on.

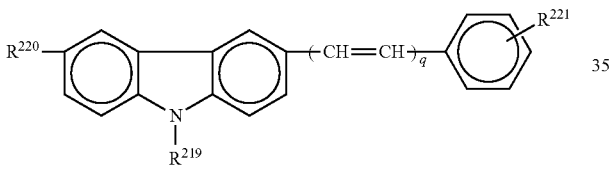

General Formula (27)

[In General Formula (27), $R^{219}$ represents a lower alkyl group, a substituted or unsubstituted phenyl group or benzyl group; $R^{220}$ and $R^{221}$ represent a hydrogen atom, a lower alkyl group, a lower alkoxy group, a halogen atom, a nitro group, an amino group or an amino group substituted by a lower alkyl group or a benzyl group; q represents an integer of 1 or 2.]

Examples of the compounds represented by General Formula (27) include 3-styryl-9-ethylcarbazole, 3-(4-methoxystyryl)-9-ethylcarbazole and so on.

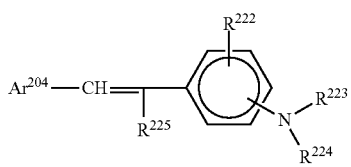

General Formula (28)

[In General Formula (28), $R^{222}$ represents a hydrogen atom, an alkyl group, an alkoxy group or a halogen atom; $R^{223}$ and $R^{224}$ represent a substituted or unsubstituted aryl group; $R^{225}$ represents a hydrogen atom, a lower alkyl group or a substituted or unsubstituted phenyl group; also, $Ar^{204}$ represents a substituted or unsubstituted phenyl group or naphthyl group.]

Examples of the compounds represented by General Formula (28) include 4-diphenylaminostilbene, 4-dibenzylaminostilbene, 4-ditolylaminostilbene, 1-(4-diphenylaminostyryl)naphthalene and so on.

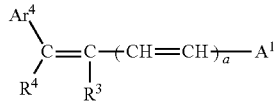

General Formula (29)

[In General Formula (29), a represents an integer of 0 or 1; $R^3$ represents a hydrogen atom, an alkyl group or a substituted or unsubstituted phenyl group; $Ar^4$ represents a substituted or unsubstituted aromatic hydrocarbon group; $R^4$ represents an alkyl group having 1 to 4 carbon atoms or a substituted or unsubstituted aromatic hydrocarbon group; $Ar^4$ and $R^4$ may jointly form a ring; $A^1$ represents a 9-anthryl group, a substituted or unsubstituted carbazolyl group, or General Formula (29A) or General Formula (29B) below; also, when a is 0, $A^1$ and $R^3$ may jointly form a ring.

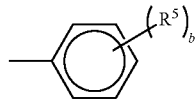

General Formula (29A)

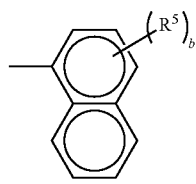

General Formula (29B)

In General Formula (29A) or (29B), $R^5$ represents a hydrogen atom, an alkyl group, an alkoxy group, a halogen atom or General Formula (29C) below; b represents an integer of 1 to 3, and when b is 2 or greater, $R^5$ may be identical or different.

General Formula (29C)

In General Formula (29C), $R^6$ and $R^7$ represents a substituted or unsubstituted aromatic hydrocarbon group, and $R^6$ and $R^7$ are identical or different and may form a ring.]

Examples of the compounds represented by General Formula (29) include 4'-diphenylamino-α-phenylstilbene, 4'-bis (4-methylphenylamino-α-phenylstilbene and so on.

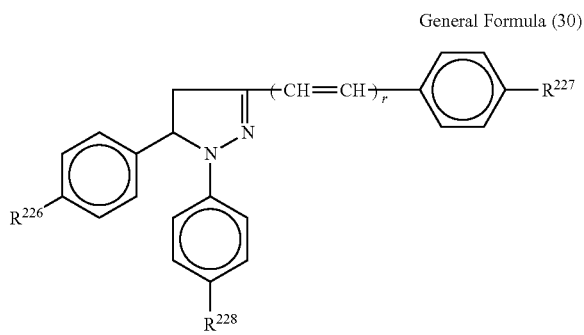

General Formula (30)

[In General Formula (30), $R^{226}$, $R^{227}$ and $R^{228}$ represent a hydrogen atom, a lower alkyl group, a lower alkoxy group, a halogen atom or a dialkylamino group; r represents 0 or 1.1

Examples of the compounds represented by General Formula (30) include 1-phenyl-3-(4-diethylaminostyryl)-5-(4-diethylaminophenyl)pyrazoline and so on.

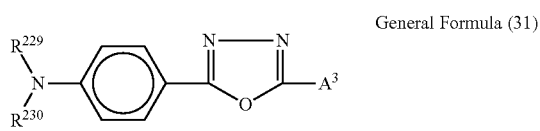

General Formula (31)

[In General Formula (31), $R^{229}$ and $R^{230}$ represent an alkyl group including a substituted alkyl group or a substituted or unsubstituted aryl group; $A^3$ represents a substituted amino group, a substituted or unsubstituted aryl group or allyl group.]

Examples of the compounds represented by General Formula (31) include 2,5-bis(4-diethylaminophenyl)-1,3,4-oxadiazole, 2-N,N-diphenylamino-5-(4-diethylaminophenyl)-1,3,4-oxadiazole, 2-(4-dimethylaminophenyl)-5-(4-diethylaminophenyl)-1,3,4-oxadiazole and so on.

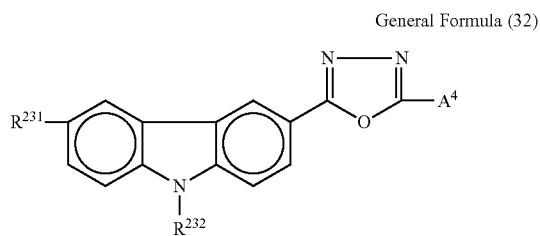

General Formula (32)

[In General Formula (32), $R^{231}$ represents a hydrogen atom, a lower alkyl group or a halogen atom; $R^{232}$ represents an alkyl group including a substituted alkyl group or a substituted or unsubstituted aryl group; $A^4$ represents a substituted amino group or a substituted or unsubstituted aryl group.]

Examples of the compounds represented by General Formula (32) include 2-N,N-diphenylamino-5-(N-ethylcarbazole-3-yl)-1,3,4-oxadiazole, 2-(4-diethylaminophenyl)-5-(N-ethylcarbazole-3-yl)-1,3,4-oxadiazole and so on.

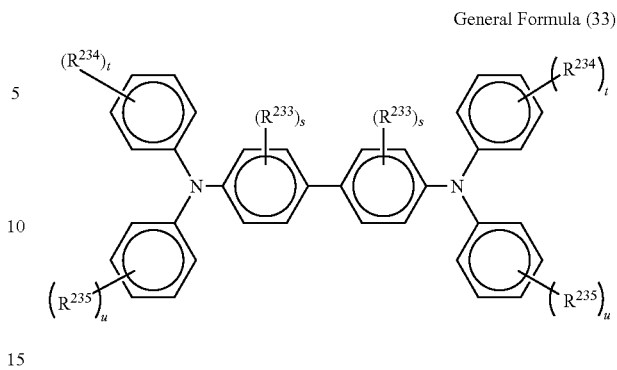

General Formula (33)

[In General Formula (33), $R^{233}$ represents a lower alkyl group, a lower alkoxy group or a halogen atom; $R^{234}$ and $R^{235}$ are identical or different, representing a hydrogen atom, a lower alkyl group, a lower alkoxy group or a halogen atom; s, t and u represent an integer of 0 to 4.]

Examples of the benzidine compounds represented by General Formula (33) include N,N'-diphenyl-N,N'-bis(3-methylphenyl)-[1,1'-biphenyl]-4,4'-diamine, 3,3'-dimethyl-N,N,N',N'-tetrakis(4-methylphenyl)-[1,1'-biphenyl]-4,4'-diamine and so on.

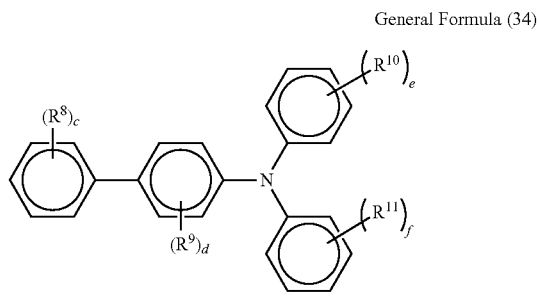

General Formula (34)

[In General Formula (34), $R^8$, $R^{10}$ and $R^{11}$ represent a hydrogen atom, an amino group, an alkoxy group, a thioalkoxy group, an aryloxy group, a methylenedioxy group, a substituted or unsubstituted alkyl group, a halogen atom, or a substituted or unsubstituted aryl group; $R^9$ represents a hydrogen atom, an alkoxy group, a substituted or unsubstituted alkyl group or a halogen atom; c, d, e and f represent an integer of 1, 2, 3 or 4, and when each thereof is an integer of 2, 3 or 4, corresponding $R^8$, $R^9$, $R^{10}$ or $R^{11}$ above is identical or different.]

Examples of the biphenylylamine compound represented by General Formula (34) include 4'-methoxy-N,N-diphenyl-[1,1'-biphenyl]-4-amine, 4'-methyl-N,N-bis(4-methylphenyl)-[1,1'-biphenyl]-4-amine, 4'-methoxy-N,N-bis(4-methylphenyl)-[1,1'-biphenyl]-4-amine, N,N-bis(3,4-dimethylphenyl)-[1,1'-biphenyl]-4-amine and so on.

General Formula (35)

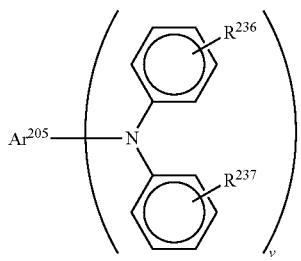

[In General Formula (35), $Ar^{205}$ represents a condensed polycyclic hydrocarbon group having 18 or less carbon atoms which may have one or more substituents; also, $R^{236}$ and $R^{237}$ represent a hydrogen atom, a halogen atom, a substituted or unsubstituted alkyl group, an alkoxy group, a substituted or unsubstituted phenyl group, and these are respectively are identical or different; v represents an integer of 1 or 2.]

Examples of the triarylamine compound represented by General Formula (35) include N,N-diphenyl-pyrene-1-amine, N,N-di-p-tolyl-pyrene-1-amine, N,N-di-p-tolyl-1-naphthylamine, N,N-di(p-tolyl)-1-phenanthrylamine, 9,9-dimethyl-2-(di-p-tolylamino)fluorene, N,N,N',N'-tetrakis(4-methylphenyl)-phenanthren-9,10-diamine, N,N,N',N'-tetrakis(3-methylphenyl)-m-phenylenediamine and so on.

General Formula (36)

[In General Formula (36), $Ar^5$ represents a substituted or unsubstituted aromatic hydrocarbon group; $A^2$ represents General Formula (36A) below.

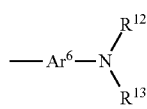
General Formula (36A)

(In General Formula (36A), $Ar^6$ represents a substituted or unsubstituted aromatic hydrocarbon group; $R^{12}$ and $R^{13}$ represent a substituted or unsubstituted alkyl group or a substituted or unsubstituted aryl group.)]

Examples of the diolefin aromatic compounds represented by General Formula (36) include 1,4-bis(4-diphenylaminostyryl)benzene, 1,4-bis[4-di(p-tolyl)aminostyryl]benzene and so on.

General Formula (37)

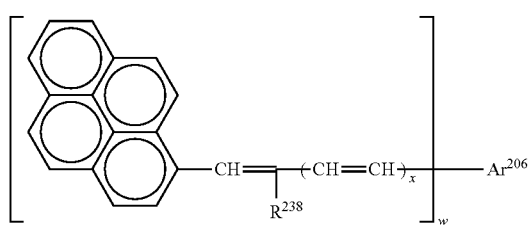

[In General Formula (37), $Ar^{206}$ represents a substituted or unsubstituted aromatic hydrocarbon group; $R^{238}$ represents a hydrogen atom, a substituted or unsubstituted alkyl group, or a substituted or unsubstituted aryl group; x represents 0 or 1, w represents 1 or 2, and when x=0 and w=1, $Ar^{206}$ and $R^{238}$ may jointly form a ring.]

Examples of the styrylpyrene compounds represented by General Formula (37) include 1-(4-diphenylaminostyryl)pyrene, 1-(N,N-di-p-tolyl-4-aminostyryl)pyrene and so on.

In the present invention, among the charge transport materials explained above, the materials represented by General Formula (29) and General Formula (34) are preferable. These materials are particularly superior in terms of mobility properties, charge injection properties from the charge generation materials, and electrostatic fatigue due to repeated charges and exposures among the low-molecular charge transport materials. Thus, by using them in a photoconductive layer, an electrophotographic photoconductor having high sensitivity and high stability may be obtained.

Also, an electron transport material which constitutes the charge transport layer is not particularly restricted and may be appropriately selected according to purpose. Examples thereof include chloranil, bromanil, tetracyanoethylene, tetracyanoquinodimethane, 2,4,7-trinitro-9-fluorenone, 2,4,5,7-tetranitro-9-fluorenone, 2,4,5,7-tetranitrothioxanthone, 2,4,8-trinitrothioxanthone, 2,6,8-trinitro-indeno4H-indeno[1,2-b]thiophen-4-one, 1,3,7-trinitrodibenzothiophene-5,5-dioxide and so on. Further, electron transport materials represented by General Formula (38) to (41) below may be favorably used.

These may be used alone or in combination of two or more.

General Formula (38)

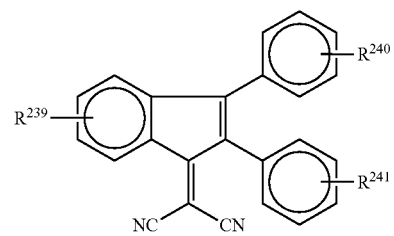

[In General Formula (38), $R^{239}$, $R^{240}$ and $R^{241}$ represent a hydrogen atom, a halogen atom, a substituted or unsubstituted alkyl group, an alkoxy group, or a substituted or unsubstituted phenyl group, and they are identical or different.]

General Formula (39)

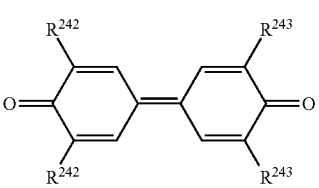

[In General Formula (39), $R^{242}$ and $R^{243}$ represent a hydrogen atom, a substituted or unsubstituted alkyl group, or a substituted or unsubstituted phenyl group, and they are identical or different.]

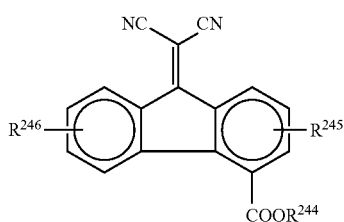

General Formula (40)

[In General Formula (40), $R^{244}$, $R^{245}$ and $R^{246}$ represent a hydrogen atom, a halogen atom, a substituted or unsubstituted alkyl group, an alkoxy group, or a substituted or unsubstituted phenyl group, and they are identical or different.]

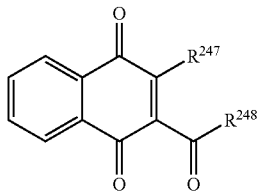

General Formula (41)

[In General Formula (41), $R^{247}$ represents an alkyl group which may have one or more substituents, or an aryl group which may have one or more substituents; $R^{248}$ represents an alkyl group which may have one or more substituents, an aryl group which may have one or more substituents, or a group represented by General Formula (41A) below.

—O—$R^{249}$  General Formula (41A)

In General Formula (41A), $R^{249}$ represents an alkyl group which may have one or more substituents, or an aryl group which may have one or more substituents.]

A binder resin which constitutes the charge transport layer is not particularly restricted and may be appropriately selected according to purpose. Examples thereof include thermoplastic or thermosetting resins such as polystyrene, styrene-acrylonitrile copolymer, styrene-butadiene copolymer, styrene-maleic anhydride copolymer, polyester, polyvinyl chloride, vinyl acetate-vinyl chloride copolymer, polyvinyl acetate, polyvinylidene chloride, polyarylate resin, phenoxy resin, polycarbonate, cellulose acetate resin, ethylcellulose resin, polyvinyl butyral, polyvinyl formal, polyvinyltoluene, poly-N-vinylcarbazole, acrylic resin, silicone resin, epoxy resin, melamine resin, urethane resin, phenolic resin and alkyd resin, and so on. These may be used alone or in combination of two or more.

When the charge transport material and the amine compound of the present invention is mixed and included in the charge transport layer, a total amount thereof is not particularly restricted and may be appropriately selected according to purpose. Nonetheless, with respect to 100 parts by mass of the binder resin, it is preferably 20 parts by mass to 300 parts by mass, and more preferably 40 parts by mass to 150 parts by mass.

An average thickness of the charge transport layer is not particularly restricted and may be appropriately selected according to purpose. Nonetheless, in terms of resolution and responsiveness, it is preferably 25 μm or less. Regarding a lower limit, although it varies depending on a system used (particularly charge potential, etc.), it is preferably 5 μm or greater.

A content of the amine compound of the present invention in the charge transport layer is not particularly restricted and may be appropriately selected according to purpose. Nonetheless, with respect to 100 parts by mass of the charge transport material, it is preferably 0.01 parts by mass to 150 parts by mass. When the content of the amine compound is small, resistance to an oxidizing gas is insufficient. When it is too large, elevation of a residual potential due to repeated use may become large.

A solvent used in forming the charge transport layer 37 is not particularly restricted and may be appropriately selected according to purpose. Examples thereof include tetrahydrofuran, dioxane, toluene, dichloromethane, monochlorobenzene, dichloroethane, cyclohexanone, methyl ethyl ketone, acetone, and so on. These may be used alone or in combination of two or more.

An antioxidant added to the charge transport layer is not particularly restricted. An ordinary antioxidant described hereinafter may be used, but (c) hydroquinone-based and (f) hindered amine-based compounds are particularly effective. Here, unlike the purpose described hereinafter, the antioxidant used here is merely used to prevent alteration of the amine compound used in the present invention. Thus, these antioxidants are preferably included in a coating solution in a process prior to adding the amine compound, and an added amount of 0.1 parts by mass to 200 parts by mass with respect to 100 parts by mass of the amine compound may exhibit a sufficient effect.

In the charge transport layer, charge transport polymers having a function as a charge transport material and a function as a binder resin are also favorably used. The charge transport layer composed of the charge transport polymers has superior abrasion resistance. The charge transport polymers are not particularly restricted and may be appropriately selected according to purpose. Nonetheless, polycarbonate including a triarylamine structure in a main chain or a side chain, or both thereof may be favorably used.

Among these, materials represented by General Formulae (11) to (13) and (42) to (51) below are favorably used.

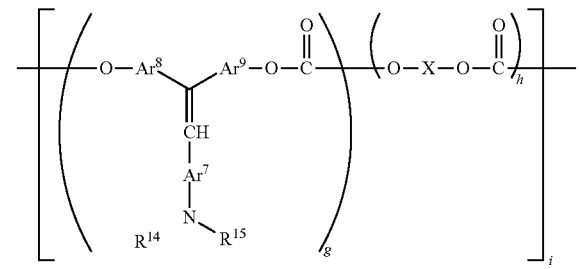

General Formula (11)

[In General Formula (11), $R^{14}$ and $R^{15}$ represent a substituted or unsubstituted aromatic hydrocarbon group; $Ar^7$, $Ar^8$ and $Ar^9$ represent identical or different aromatic hydrocarbon group; g and h represent compositions: $0.1 \leq g \leq 1$; $0 \leq h \leq 0.9$; i represents a number of repeating units and is an integer of 5 to 5,000.

X represents a divalent aliphatic group, a divalent cyclic aliphatic group, or a divalent group represented by General Formula (12) below.]

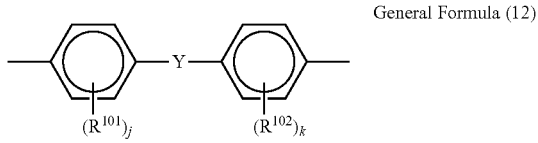
General Formula (12)

(In General Formula (12), each of $R^{101}$ and $R^{102}$ independently represents a substituted or unsubstituted alkyl group, an aromatic hydrocarbon group, or a halogen atom; j and k represent an integer of 0 to 4; Y represents a single bond, a linear, branched or cyclic alkylene group having 1 to 12 carbon atoms; —O—, —S—, —SO—, —SO$_2$—, —CO—, —CO—O—Z—O—CO— (where Z represents an divalent aliphatic group), or General Formula (13) below. Here, $R^{101}$ and $R^{102}$ are identical or different, respectively.)

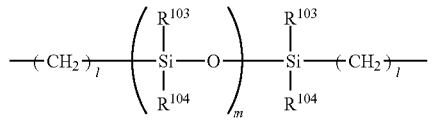
General Formula (13)

(In General Formula (13), l represents an integer of 1 to 20; m represents an integer of 1 to 2,000; $R^{103}$ and $R^{104}$ represent a substituted or unsubstituted alkyl group or aryl group. Here, $R^{103}$ and $R^{104}$ are identical or different, respectively.)

[In General Formula (43), $R^{255}$ and $R^{256}$ represent a substituted or unsubstituted aryl group; $Ar^{207}$, $Ar^{208}$ and $Ar^{209}$ represent an identical or different arylene group; X, g, h and i are the same as those in General Formula (11).]

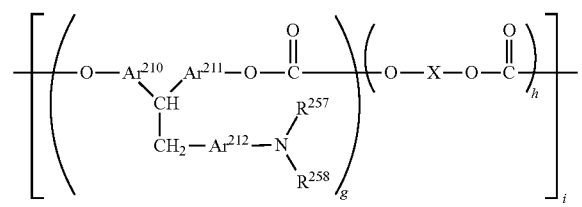
General Formula (44)

[In General Formula (44), $R^{257}$ and $R^{258}$ represent a substituted or unsubstituted aryl group; $Ar^{210}$, $Ar^{211}$ and $Ar^{212}$ represent an identical or different arylene group; X, g, h and i are the same as those in General Formula (11).]

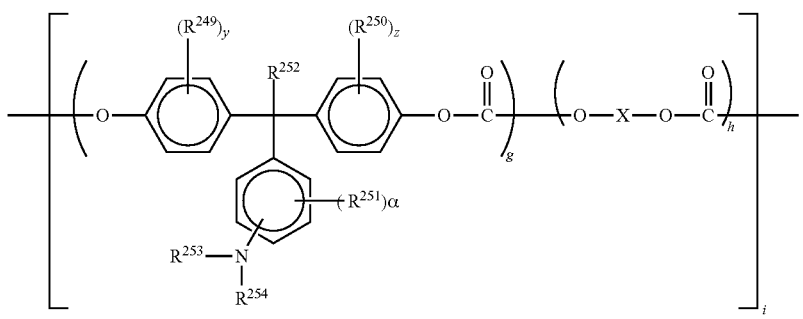
General Formula (42)

[In General Formula (42), each of $R^{249}$, $R^{250}$ and $R^{251}$ represents independently a substituted or unsubstituted alkyl group or a halogen atom; $R^{252}$ represents a hydrogen atom or a substituted or unsubstituted alkyl group; $R^{253}$ and $R^{254}$ represents a substituted or unsubstituted aryl group; each of y, z and α represents independently an integer of 0 to 4; X, g, h and i are the same as those in General Formula (11).]

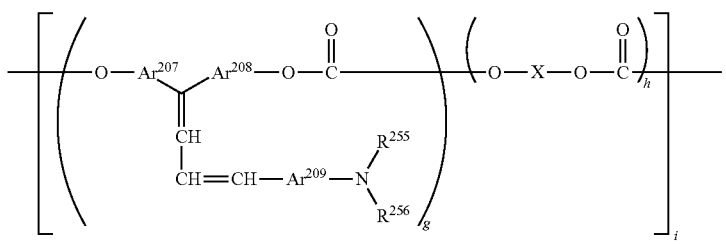
General Formula (43)

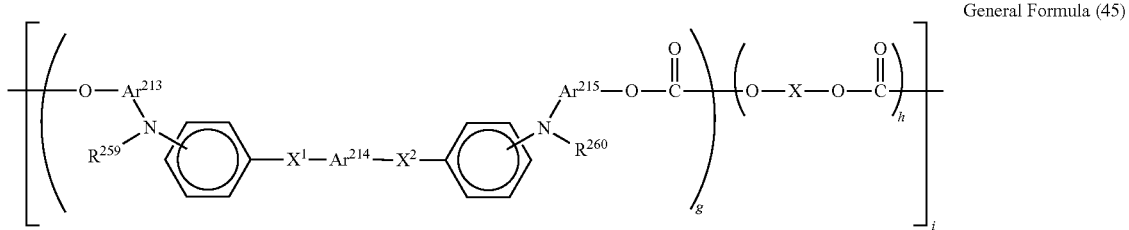

General Formula (45)

[In General Formula (45), $R^{259}$ and $R^{260}$ represent a substituted or unsubstituted aryl group; $Ar^{213}$, $Ar^{214}$ and $Ar^{215}$ represent an identical or different arylene group; $X_1$ and $X_2$ represent a substituted or unsubstituted ethylene group, or a substituted or unsubstituted vinylene group; X, g, h and i are the same as those in General Formula (11).]

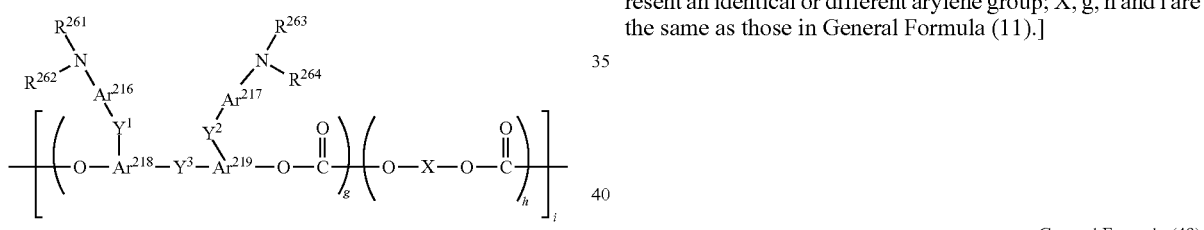

General Formula (46)

[In General Formula (46), $R^{261}$, $R^{262}$, $R^{263}$ and $R^{264}$ represent a substituted or unsubstituted aryl group; $Ar^{216}$, $Ar^{217}$, $Ar^{218}$ and $Ar^{219}$ represent an identical or different arylene group; $Y_1$, $Y_2$ and $Y_3$ represent a single bond, a substituted or unsubstituted alkylene group, a substituted or unsubstituted cycloalkylene group, a substituted or unsubstituted alkylene ether group, an oxygen atom, a sulfur atom, or a vinylene group, and they are identical or different; X, g, h and i are the same as those in General Formula (11).]

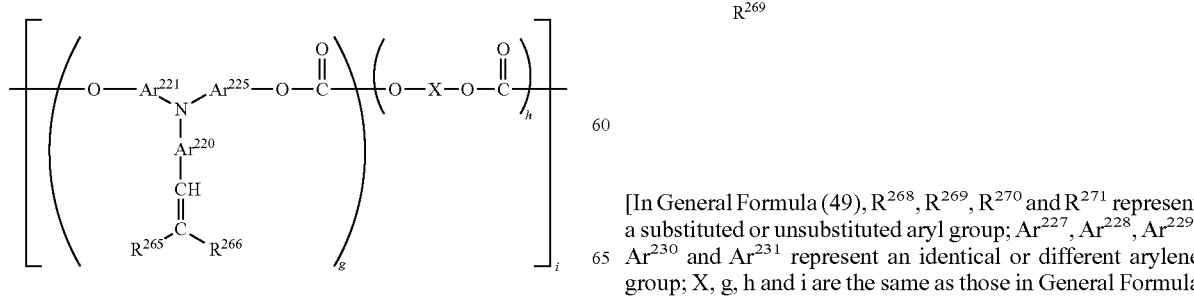

General Formula (47)

[In General Formula (47), $R^{265}$ and $R^{266}$ represent a hydrogen atom, or a substituted or unsubstituted aryl group; $R^{265}$ and $R^{266}$ may form a ring; $Ar^{220}$, $Ar^{221}$ and $Ar^{222}$ represent an identical or different arylene group; X, g, h and i are the same as those in General Formula (11).]

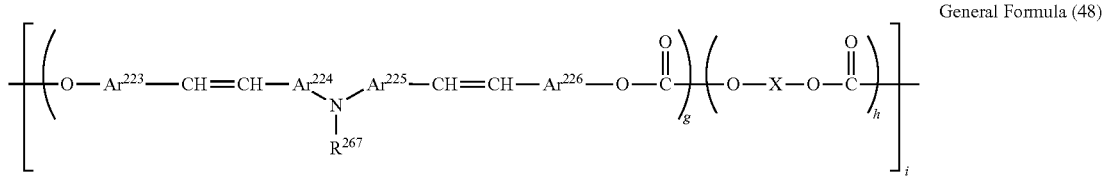

General Formula (48)

[In General Formula (48), $R^{267}$ represents a substituted or unsubstituted aryl group; $Ar^{223}$, $Ar^{224}$, $Ar^{225}$ and $Ar^{226}$ represent an identical or different arylene group; X, g, h and i are the same as those in General Formula (11).]

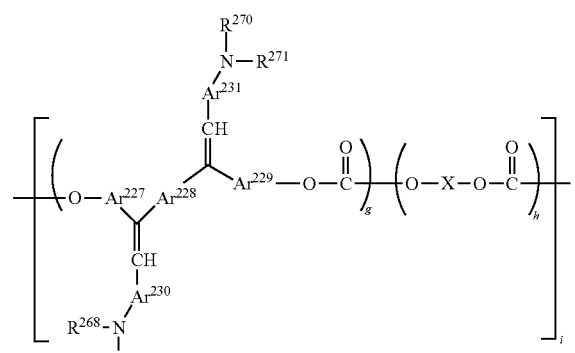

General Formula (49)

[In General Formula (49), $R^{268}$, $R^{269}$, $R^{270}$ and $R^{271}$ represent a substituted or unsubstituted aryl group; $Ar^{227}$, $Ar^{228}$, $Ar^{229}$, $Ar^{230}$ and $Ar^{231}$ represent an identical or different arylene group; X, g, h and i are the same as those in General Formula (11).]

General Formula (50)

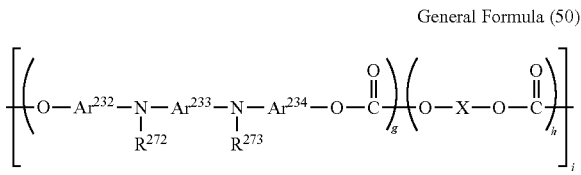

[In General Formula (50), $R^{272}$ and $R^{273}$ represent a substituted or unsubstituted aryl group; $Ar^{232}$, $Ar^{233}$ and $Ar^{234}$ represent an identical or different arylene group; X, g, h and i are the same as those in General Formula (11).]

General Formula (51)

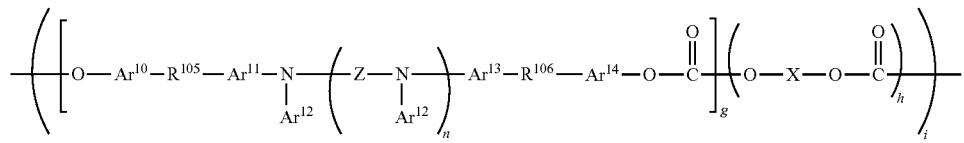

[In General Formula (51), $Ar^{10}$, $Ar^{11}$, $Ar^{12}$, $Ar^{13}$ and $Ar^{14}$ represent a substituted or unsubstituted aromatic hydrocarbon group; Z represents an aromatic hydrocarbon group or $Ar^{15}$-Za-$Ar^{15}$—, where $Ar^{15}$ represents a substituted or unsubstituted aromatic hydrocarbon group, Za represents O, S or an alkylene group; $R^{105}$ and $R^{106}$ represent a linear or branched alkylene group; n represents 0 or 1; g, h, i and X are the same as those in General Formula (11).]

The charge transport material is dissolved alone or with the binder resin in an appropriate solvent, which is applied on the charge generation layer followed by drying, and thereby the charge transport layer is formed. Also, a single, or two or more plasticizers, leveling agents, antioxidants and so on may be added according to necessity.

A coating method of a charge transport layer coating solution as obtained above is not particularly restricted and may be appropriately selected according to purpose. For example, conventional coating methods including a dip-coating method, a spray-coating method, a bead-coating method, a nozzle-coating method, a spinner-coating method, a ring-coating method, and so on may be used.

In the present invention, among the polymeric charge transport materials explained above, those represented by General Formula (11) and General Formula (51) are preferable. Since these have superior abrasion resistance and high mobility properties among the polymeric charge transport materials, a photoconductor having high durability and high sensitivity may be obtained by using them in the photoconductive layer.

<<Single-Layer Photoconductive Layer>>

Next, the photoconductive layer as a single layer is described.

The photoconductive layer may be formed by dissolving or dispersing the amine compound of the present invention represented by General Formula (I), a charge generation material, a charge transport material and a binder resin in an appropriate solvent and coating and drying it. Also, according to necessity, a plasticizer, a leveling agent, an antioxidant and so on may be added. As the charge generation material, those used for the charge generation layer in a multilayer structure described above may also be used.

The binder resin in the case of forming the single-layer photoconductive layer is not particularly restricted. In addition to the binder resins exemplified for the charge transport layer above, the binder resins exemplified for the charge generation layer may be mixed and used. Of course, charge transport polymers exemplified above may also be favorably used.

With respect to 100 parts by mass of the binder resin, a content of the charge generation material is preferably 5 parts by mass to 40 parts by mass, and a content of the charge transport material is preferably 0 parts by mass to 190 parts by mass, and more preferably 50 parts by mass to 150 parts by mass.

A coating solution obtained by dispersing the charge generation material and the binder resin along with the charge transport material with a disperser using a solvent such as tetrahydrofuran, dioxane, dichloroethane and cyclohexane is coated by a dip-coating method, a spray-coating method, a bead-coating method, a ring-coating method and so on, and thereby the photoconductive layer is formed.

An average thickness of the photoconductive layer is not particularly restricted and may be appropriately selected according to purpose. Nonetheless, it is preferably 5 μm to 25 μm.

—Undercoat Layer—

In the photoconductor of the present invention, an undercoat layer may be disposed between the electrically conductive substrate and the photoconductive layer.

The undercoat layer generally includes a resin as a main component. The resin preferably has high solvent resistance to ordinary organic solvents, considering that the photoconductive layer is applied thereon with a solvent. The resin is not particularly restricted and may be appropriately selected according to purpose. Examples thereof include a water-soluble resin such as polyvinyl alcohol, casein, and sodium polyacrylate; an alcohol-soluble resin such as copolymerized nylon, and methoxymethylated nylon; polyurethane, a melamine resin, a phenolic resin, an alkyd-melamine resin, an epoxy resin and so on; and a curable resin which forms a three-dimensional network structure.

To the undercoat layer, for preventing moiré, reducing residual potential, etc., pigment powder of a metal oxide exemplified by titanium oxide, silica, alumina, zirconium oxide, tin oxide, indium oxide and so on may be added.

Similarly to the photoconductive layer, the undercoat layer may be formed using an appropriate solvent and a coating method. Further, as the undercoat layer, a silane coupling agent, a titanate coupling agent, a chromium coupling agent and so on may also be used. Other than this, $Al_2O_3$ provided by anodic oxidation, organic substances such as poly-para-xylylene (parylene) or inorganic substances such as $SiO_2$, $SnO_2$, $TiO_2$, ITO and $CeO_2$ provided by vacuum thin-film formation may also be favorably used in the undercoat layer. Other than this, heretofore known substances may be used.

An average thickness of the undercoat layer is not particularly restricted and may be appropriately selected according to purpose. Nonetheless, it is preferably 0 μm to 5 μm.

—Protective Layer—

In the photoconductor of the present invention, for the purpose of protecting the photoconductive layer, a protective layer may be disposed on the photoconductive layer.

Examples of a material used for the protective layer include resins such as ABS resin, ACS resin, olefin-vinyl monomer copolymer, chlorinated polyether, aryl resin, phenolic resin, polyacetal, polyamide, polyamideimide, polyacrylate, polyallyl sulfone, polybutylene, polybutylene terephthalate, polycarbonate, polyether sulfone, polyethylene, polyethylene terephthalate, polyimide, acrylic resin, polymethylbenzene, polypropylene, polyphenylene oxide, polysulfone, polystyrene, polyarylate, AS resin, butadiene-styrene copolymer, polyurethane, polyvinyl chloride, polyvinylidene chloride, epoxy resin, and so on. Among these, in view of filler dispersibility, residual potential, and coating defects, polycarbonate, polyarylate are particularly preferable.

Also, the protective layer preferably includes a resin formed by curing a polymerizable monomer.

The polymerizable monomer is not particularly limited and may be appropriately selected according to purpose. Examples thereof include polymerizable monomers described in, for example, paragraphs [0042] to [0056] of JP-A No. 2012-058668.

The protective layer preferably includes a filler in view of improving abrasion resistance.

The filler is classified into an organic filler material and an inorganic filler material.

Examples of the organic filler material include: fluororesin powder such as polytetrafluoroethylene; and silicone resin powder and α-carbon powder.

Examples of the inorganic filler material include: powders of metals such as copper, tin, aluminum and indium; metal oxides such as silica, tin oxide, zinc oxide, titanium oxide, alumina, zirconium oxide, indium oxide, antimony oxide, bismuth oxide, calcium oxide, tin oxide doped with antimony, and indium oxide doped with tin; metal fluorides such as tin fluoride, calcium fluoride and aluminum fluoride, potassium titanate and boron nitride.

Among them, use of inorganic materials is advantageous from the viewpoint of increasing abrasion resistance, since they have higher hardness. In particular, metal oxides are preferably used.

The filler is preferably a filler having high electrical insulating property. It is particularly advantageous to use a filler having a pH of 5 or higher or a filler having a dielectric constant of 5 or higher. Titanium oxide, alumina, zinc oxide and zirconium oxide can be used particularly advantageously.

Needless to say, the filler having a pH of 5 or higher or the filler having a dielectric constant of 5 or higher may be used alone. Alternatively, two or more different kinds of fillers may be used in combination; e.g., the filler having a pH of 5 or higher may be mixed with another filler having a pH of 5 or lower, and the filler having a dielectric constant of 5 or higher may be mixed with another filler having a dielectric constant of 5 or lower.

In particular, α-type alumina is particularly useful from the viewpoint of increasing abrasion resistance and preventing image blurring, since it has high insulating property, high thermal stability, and a hexagonal close-packed structure exhibiting high abrasion resistance.

Moreover, the filler can be surface-treated with at least one surface treating agent. Surface-treating the filler is preferable from the viewpoint of dispersibility of the filler.

Decrease in dispersibility of the filler causes not only an increase in residual potential but also may cause a decrease in transparency of the coated film, formation of defects in the coated film, and a decrease in abrasion resistance, potentially leading to severe problems that inhibit high durability or high quality image formation.

The surface treating agent may be any conventionally-used surface treating agent, but preferably used is a surface treating agent able to maintain the insulating property of the filler.

From the viewpoints of improving filler dispersibility and preventing image blur, such surface treating agent is more preferably a titanate coupling agent, an aluminum coupling agent, a zircoaluminate coupling agent, a higher fatty acid, mixtures containing these agents or acids and a silane coupling agent; $Al_2O_3$, $TiO_2$, $ZrO_2$, silicone, aluminum stearate and mixtures thereof.

A treatment with a silane coupling agent alone causes a considerable degree of image blurring, while a treatment with the mixture containing the above surface treating agent and a silane coupling agent may suppress such disadvantageous effect caused by the silane coupling agent.

The amount of the surface treating agent is not particularly restricted but varies with the average primary particle diameter of the filler. It is preferably 3% by mass to 30% by mass, more preferably 5% by mass to 20% by mass.

When the surface treating agent is less than the lower limit, it cannot exhibit an effect of dispersing the filler. Whereas when the surface treating agent is too large, it causes a considerable increase in residual potential.

Also, the average primary particle diameter of the filler is preferably 0.01 μm to 0.5 μm from the viewpoint of improving optical transmittance and abrasion resistance of the charge transport layer 37.

When the average primary particle diameter of the filler is less than 0.01 μm, abrasion resistance, dispersibility, etc. are decreased. Whereas when it is more than 0.5 μm, there may be a case where the filler easily sediments and toner filming occurs.

The amount of the filler is not particularly limited and may be appropriately selected according to purpose, but is preferably 5% by mass to 50% by mass, more preferably 10% by mass to 40% by mass.

When it is less than 5% by mass, sufficient abrasion resistance may not be obtained. Whereas when it is more than 50% by mass, transparency of the charge transport layer may be degraded.

The solvent used for forming the protective layer is not particularly restricted and may be appropriately selected according to purpose. Examples thereof include tetrahydrofuran, dioxane, toluene, dichloromethane, monochlorobenzene, dichloroethane, cyclohexanone, methyl ethyl ketone, acetone and so on. Here, solvents having a high viscosity during dispersion are preferable, but solvents having high volatility during coating are preferable.

When a solvent which satisfy these conditions is not available, two or more solvents which have the respective properties may be mixed and used, which may be significantly effective for filler dispersibility or residual potential.

Also, the protective layer may include the amine compound of the present invention represented by General Formula (I). Further, addition of the low-molecular charge transport material or the charge transport polymers described for the charge transport layer is effective and useful in view of reducing residual potential and improving image quality.

A method for forming the protective layer is not particularly restricted and may be appropriately selected according to purpose. For example, conventional methods including a dip-coating method, a spray-coating method, a bead-coating method, a nozzle-coating method, a spinner-coating method, a ring-coating method and so on may be used. Among these, in view of uniform film formation, the spray-coating method is particularly preferable.

—Intermediate Layer—

In the photoconductor of the present invention, an intermediate layer may be disposed between the photoconductive layer and the protective layer.

The intermediate layer generally includes a binder resin as a main component. The binder resin is not particularly restricted and may be appropriately selected according to purpose. Examples thereof include polyamide, alcohol-soluble nylon, water-soluble polyvinyl butyral, polyvinyl butyral, polyvinyl alcohol, and so on.

As a method for forming the intermediate layer, a coating method generally used as above is employed.

An average thickness of the intermediate layer is not particularly restricted and may be appropriately selected according to purpose. Nonetheless, it is preferably 0.05 μm to 2 μm.

In the present invention, for the purpose of improving environmental resistance, especially preventing reduction of sensitivity and increase of residual potential, an antioxidant, a plasticizer, a lubricant, a ultraviolet absorber, and a leveling agent may be added to the respective layers of the charge generation layer, the charge transport layer, the single-layer photoconductive layer, the undercoat layer, the protective layer, the intermediate layer and so on. Typical materials of these compounds are described below.

Examples of the antioxidant include phenolic compounds, paraphenylenediamines, hydroquinones, organic sulfur compounds, organic phosphorus compounds, and so on.

Examples of the phenolic compounds include 2,6-di-t-butyl-p-cresol, butylated hydroxyanisoles, 2,6-di-t-butyl-4-ethylphenol, stearyl-β-(3,5-di-t-butyl-4-hydroxyphenyl)propionate, 2,2'-methylene-bis-(4-methyl-6-t-butylphenol), 2,2'-methylene-bis-(4-ethyl-6-t-butylphenol), 4,4'-thiobis-(3-methyl-6-t-butylphenol), 4,4'-butylidenebis-(3-methyl-6-t-butylphenol), 1,1,3-tris-(2-methyl-4-hydroxy-5-t-butylphenyl)butane, 1,3,5-trimethyl-2,4,6-tris(3,5-di-t-butyl-4-hydroxybenzyl)benzene, tetrakis-[methylene-3-(3',5'-di-t-butyl-4'-hydroxyphenyl)propionate]methane, bis[3,3'-bis(4'-hydroxy-3'-t-butylphenyl)butyric acid]glycol ester, tocopherols, and so on.

Examples of the paraphenylenediamines include N-phenyl-N'-isopropyl-p-phenylenediamine, N,N'-di-sec-butyl-p-phenylenediamine, to N-phenyl-N-sec-butyl-p-phenylenediamine, N,N'-di-isopropyl-p-phenylenediamine, N,N'-dimethyl-N,N'-di-t-butyl-p-phenylenediamine, and so on.

Examples of the hydroquinones include 2,5-di-t-octylhydroquinone, 2,6-didodecylhydroquinone, 2-dodecylhydroquinone, 2-dodecyl-5-chlorohydroquinone, 2-t-octyl-5-methylhydroquinone, 2-(2-octadecenyl)-5-methylhydroquinone, and so on.

Examples of the organic sulfur compounds include dilauryl-3,3'-thiodipropionate, distearyl-3,3'-thiodipropionate, ditetradecyl-3,3'-thiodipropionate, and so on.

Examples of the organic phosphorus compounds include triphenylphosphine, tri(nonylphenyl)phosphine, tri(di-nonylphenyl)phosphine, tricresylphosphine, tri(2,4-dibutylphenoxy)phosphine, and so on.

These compounds are known as antioxidants of rubbers, plastics and fats, and commercially available products may be easily obtained.

An added amount of the antioxidant is not particularly restricted and may be appropriately selected according to purpose. Nonetheless, it is preferably 0.01% by mass to 10% by mass with respect to the total mass of a layer to which the antioxidant is added.

Also, a plasticizer which may be added to the respective layers is not particularly restricted and may be appropriately selected according to purpose. Examples thereof include phosphate plasticizers, phthalate plasticizers, aromatic carboxylic acid ester plasticizers, aliphatic dibasic acid ester plasticizers, fatty acid ester derivatives, oxy acid ester plasticizers, epoxy plasticizers, dihydric alcohol ester plasticizers, chlorine-containing plasticizers, polyester plasticizers, sulfonic acid derivatives, citric acid derivatives, and other plasticizers.

Examples of the phosphate plasticizers include triphenyl phosphate, tricresyl phosphate, trioctyl phosphate, octyldiphenyl phosphate, trichloroethyl phosphate, cresyldiphenyl phosphate, tributyl phosphate, tri-2-ethylhexyl phosphate and so on.

Examples of the phthalate plasticizers include dimethyl phthalate, diethyl phthalate, diisobutyl phthalate, dibutyl phthalate, diheptyl phthalate, di-2-ethylhexyl phthalate, diisooctyl phthalate, di-n-octyl phthalate, dinonyl phthalate, diisononyl phthalate, diisodecyl phthalate, diundecyl phthalate, ditridecyl phthalate, dicyclohexyl phthalate, butylbenzyl phthalate, butyllauryl phthalate, methyloleyl phthalate, octyldecyl phthalate and so on.

Examples of the aromatic carboxylic acid ester plasticizers include trioctyl trimellitate, tri-n-octyl trimellitate, octyl oxybenzoate, and so on.

Examples of the aliphatic dibasic acid ester plasticizers include dibutyl adipate, di-n-hexyl adipate, di-2-ethylhexyl adipate, di-n-octyl adipate, n-octyl-n-decyl adipate, diisodecyl adipate, dicapryl adipate, di-2 ethylhexyl azelate, dimethyl sebacate, diethyl sebacate, dibutyl sebacate, di-n-octyl sebacate, di-2-ethylhexyl sebacate, di-2-ethoxyethyl sebacate, dioctyl succinate, diisodecyl succinate, dioctyl tetrahydrophthalate, di-n-octyl tetrahydrophthalate, and so on.

Examples of the fatty acid ester derivatives include butyl oleate, glycerin monooleic acid ester, methyl acetylricinolate, pentaerythritol ester, dipentaerythritol hexaester, triacetin, tributyrin, and so on.

Examples of the oxy acid ester plasticizers include methyl acetylricinolate, butyl acetylricinoleate, butyl phthalylbutylglycolate, tributyl acetylcitrate, and so on.

Examples of the epoxy plasticizers include epoxidized soybean oil, epoxidized linseed oil, butyl epoxystearate, decyl epoxystearate, octyl epoxystearate, benzyl epoxystearate, dioctyl epoxyhexahydrophthalate, didecyl epoxyhexahydrophthalate, and so on.

Examples of the dihydric alcohol ester plasticizers include diethylene glycol dibenzoate, triethylene glycol di-2-ethylbutyrate, and so on.

Examples of the chlorine-containing plasticizers include chlorinated paraffin, chlorinated diphenyl, chlorinated fatty acid methyl ester, methoxy chlorinated fatty acid methyl ester, and so on.

Examples of the polyester plasticizers include polypropylene adipate, polypropylene sebacate, polyester, acetylated polyester, and so on.

Examples of the sulfonic acid derivatives include p-toluenesulfonamide, o-toluenesulfonamide, p-toluenesulfoneethylamide, o-toluenesulfoneethylamide, p-toluenesulfone-N-cyclohexylamide, and so on.

Examples of the citric acid derivatives include triethyl citrate, triethyl acetylcitrate, tributyl citrate, tributyl acetylcitrate, tri-2-ethylhexyl acetylcitrate, n-octyldecyl acetylcitrate, and so on.

Examples of the other plasticizers include terphenyl, partially hydrogenated terphenyl, camphor, 2-nitrodiphenyl, dinonylnaphthalene, methyl abietate, and so on.

The lubricant which may be added to the respective layers is not particularly restricted and may be appropriately selected according to purpose. Examples thereof include hydrocarbon compounds, aliphatic acid compounds, fatty acid amide compounds, ester compounds, alcohol compounds, metal soaps, natural waxes, and other lubricant.

Examples of the hydrocarbon compounds include liquid paraffin, paraffin wax, microwax, low-polymer polyethylene, and so on.

Examples of the fatty acid compounds include lauric acid, myristic acid, palmitic acid, stearic acid, arachidic acid, behenic acid, and so on.

Examples of the fatty acid amide compounds include stearyl amide, palmityl amide, oleic amide, methylenebis (stearic amide), ethylenebis(stearic amide), and so on.

Examples of the ester compounds include lower alcohol esters of a fatty acid, polyhydric alcohol esters of a fatty acid, fatty acid polyglycol esters, and so on.

Examples of the alcohol compounds include cetyl alcohol, stearyl alcohol, ethylene glycol, polyethylene glycol, polyglycerol, and so on.

Examples of the metal soaps include lead stearate, cadmium stearate, barium stearate, calcium stearate, zinc stearate, magnesium stearate, and so on.

Examples of the natural waxes include carnauba wax, candelilla wax, bees wax, spermaceti, insects wax, montan wax, and so on.

Examples of the other lubricants include silicone compounds, fluorine compounds, and so on.

The ultraviolet absorber which may be added to the respective layers is not particularly restricted and may be appropriately selected according to purpose. Examples thereof include benzophenone-based ultraviolet absorbers, salicylate-based ultraviolet absorbers, benzotriazole-based ultraviolet absorbers, cyanoacrylate-based ultraviolet absorbers, quencher (metal complex-based) ultraviolet absorbers, HALS (hindered amine), and so on.

Examples of the benzophenone-based ultraviolet absorbers include 2-hydroxybenzophenone, 2,4-dihydroxybenzophenone, 2,2',4-trihydroxybenzophenone, 2,2',4,4'-tetrahydroxybenzophenone, 2,2'-dihydroxy-4-methoxybenzophenone, and so on.

Examples of the salicylate-based ultraviolet absorbers include phenyl salicylate, 2,4-di-t-butylphenyl-3,5-di-t-butyl-4-hydroxybenzoate, and so on.

Examples of the benzotriazole-based ultraviolet absorbers include (2'-hydroxyphenyl)benzotriazole, (2'-hydroxy-5'-methylphenyl)benzotriazole, (2'-hydroxy-5'-methylphenyl) benzotriazole, (2'-hydroxy-3'-tertiarybutyl-5'-methylphenyl)-5-chlorobenzotriazole, and so on.

Examples of the cyanoacrylate-based ultraviolet absorbers include ethyl 2-cyano-3,3-diphenylacrylate, methyl 2-carbomethoxy-3(paramethoxy)acrylate, and so on.

Examples of the quencher (metal complex-based) ultraviolet absorbers include nickel (2,2'-thiobis(4-t-octyl)phenolate) N-butylamine, nickel dibutyldithiocarbamate, cobalt dicyclohexyldithiophosphate, and so on.

Examples of the HALS (hindered amine) include bis(2,2,6,6-tetramethyl-4-piperidyl)sebacate, bis(1,2,2,6,6-pentamethyl-4-piperidyl)sebacate, 1-[2-[3-(3,5-di-t-butyl-4-hydroxyphenyl)propionyloxy]ethyl]-4-[3-(3,5-di-t-butyl-4-hydroxyphenyl)propionyloxy]-2,2,6,6-tetramethylpyridine, 8-benzyl-7,7,9,9-tetramethyl-3-octyl-1,3,8-triazaspiro[4,5] undecane-2,4-dione, 4-benzoyloxy-2,2,6,6-tetramethylpiperidine, and so on.

(Image Forming Apparatus and Image Forming Method)

An image forming apparatus of the present invention includes at least an electrophotographic photoconductor, a charging unit, an exposure unit, a developing unit, and a transfer unit, and it further includes other units appropriately selected according to necessity such as fixing unit, cleaning unit, neutralizing unit, recycling unit and controlling unit.

The electrophotographic photoconductor is the electrophotographic photoconductor of the present invention.

An image forming method used in the present invention includes at least a charging step, an exposing step, a developing step, and a transfer step, and it further includes other steps selected according to necessity such as fixing step, cleaning step, neutralizing step, recycling step and controlling step.

The image forming method used in the present invention may be favorably carried out by the image forming apparatus of the present invention; the charging step may be carried out by the charging unit; the exposing step may be carried out by the exposure unit; the developing step may be carried out by the developing unit; the transfer step may be carried out by the transfer unit; and the other steps may be carried out by the other units.

—Charging Step and Charging Unit—

The charging step is a step of charging a surface of the electrophotographic photoconductor, and it is carried out by the charging unit.

The charging unit is not particularly restricted as long as it applies a voltage on a surface of the electrophotographic photoconductor to charge it uniformly, and it may be appropriately selected according to purpose. Nonetheless, a non-contact charging unit in which the electrophotographic photoconductor is charged in a non-contact manner is used.

Examples of the non-contact charging unit include: a non-contact charger, a needle-electrode device and a solid discharge element which use corona discharge; electrically conductive or semiconductive charging rollers arranged with a small gap with the electrophotographic photoconductor; and so on. Among these, the corona discharge is particularly preferable.

The corona discharge is a non-contact charging method which provides positive or negative ions generated by corona discharge in the air to a surface of the electrophotographic photoconductor, and there are a coroton charger which is characterized by providing a predetermined amount of charge to the electrophotographic photoconductor and a scorotron charger characterized by providing a predetermined electric potential.

The coroton charger is composed of a casing electrode which occupies half of a space around a discharge wire and a discharge wire which is placed at an approximate center thereof.

The scorotron charger is a charger that a grid electrode is added to the coroton charger, and the grid electrode is arranged at a position distant from a surface of the electrophotographic photoconductor by 1.0 mm to 2.0 mm.

—Exposing Step and Exposure Unit—

The exposure may be carried out, for example, by image-wise exposure of a surface of the electrophotographic photoconductor using the exposure unit.

Optical systems in the exposure are divided into an analog optical system and a digital optical system. The analog optical system is an optical system that a document is projected by the optical system directly on the electrophotographic photoconductor, and the digital optical system is an optical system that image information is provided as electrical signals, which are converted to optical signals, and that an image is formed by exposing the electrophotographic photoconductor.

The exposure unit is not particularly restricted as long as image-wise exposure may be carried out on a surface of the electrophotographic photoconductor charged by the charging unit, and it may be appropriately selected according to purpose. Nonetheless, for example, various exposure devices including a duplication optical system, a rod lens array system, a laser optical system, a liquid crystal shutter optical system, a led optical system, and so on may be used.

Here, in the present invention, a back light system in which image-wise exposure is carried out from a back side of the electrophotographic photoconductor may be employed.

—Developing Step and Developing Unit—

The developing step is a step for forming a visible image by developing the electrostatic latent image using a toner or a developer.

Formation of the visible image may be carried out, for example, by developing the electrostatic latent image using the toner or the developer, and it may be carried out by the developing unit.

The developing unit is not particularly restricted as long as it may develop using the toner or the developer, for example, and it may be appropriately selected from heretofore known units. For example, a developing unit which contains the toner or the developer and includes at least a developing device that may provide the toner or the developer to the electrostatic latent image in a contact or non-contact manner may be favorably used.

The developing device may be of a dry developing method or a wet developing method, and also it may be a single-color developing device or a multi-color developing device. For example, a developing device which includes a stirrer which frictionally stirs to charge the toner or the developer and a rotatable magnet roller may be favorably used.

In the developing device, for example, the toner and the carrier are mixed and stirred. The toner is charged by the friction therefrom and is maintained in a state of ear standing on a surface of the rotating magnet roller, and a magnetic brush is formed. Since the magnet roller is arranged near the electrophotographic photoconductor (photoconductor), a part of the toner which constitutes the magnetic brush formed on the surface of the magnet roller moves to the surface of the electrophotographic photoconductor by an electrical attractive force. As a result, the electrostatic latent image is developed by the toner, and a visible image is formed by the toner on a surface of the electrophotographic photoconductor.

The developer to be contained in the developing device is a developer including the toner, but the developer may be a one-component developer or a two-component developer.

—Transfer Step and Transfer Unit—

The transfer step is a step for transferring the visible image on a recording medium, and a preferable aspect includes a primary transfer that, using an intermediate transfer body, a visible image is transferred on the intermediate transfer body and a secondary transfer that the visible image is transferred on the recording medium. An aspect including a primary transfer step that a visible image is transferred on an intermediate transfer body using a toner of two or more colors, or preferably a full-color toner as the toner, to form a composite transfer image and a secondary transfer step that the composite transfer image is transferred on the recording medium is more preferable.

The transfer may be carried out, for example, by charging the electrophotographic photoconductor using a transfer charger to charge the visible image, and it may be carried out using the transfer unit. As the transfer unit, an aspect including a primary transfer unit which forms a composite transfer image by transferring a visible image on an intermediate transfer body and a secondary transfer unit which transfers the composite transfer image on a recording medium is preferable.

Here, the intermediate transfer body is not particularly restricted and may be appropriately selected from heretofore known transfer bodies according to purpose. For example, a transfer belt and so on may be favorably used.

The transfer unit (the primary transfer unit and the secondary transfer unit) preferably includes at least a transfer device which imparts electrostatic charge on the visible image formed on the electrophotographic photoconductor to a side of the recording medium. The transfer unit may be one, or two or more. Examples of the transfer device include a corona transfer device, a transfer belt, a transfer roller, a pressure transfer roller, an adhesive transfer device and so on by corona discharge.

Here, the recording medium is typically plain paper but is not particularly restricted as long as a non-fixed image after development may be transferred, and it may be appropriately selected according to purpose. A PET base for OHP may also be used.

—Fixing Step and Fixing Unit—

The fixing step is a step for fixing a visible image transferred on a recording medium using a fixing apparatus. It may be carried out each time a toner of respective colors is transferred on the recording medium, or it may be carried out once when the toners of respective colors are laminated.

The fixing unit is not particularly restricted and may be appropriately selected according to purpose. Nonetheless, a unit including a fixing member and a heat source which heats the fixing member is used.

As the fixing member, for example, a combination of an endless belt and a roller, a combination of a roller and a roller, and so on may reduce a warm-up period, and a combination of an endless belt and a roller, having a small heat capacity, is preferable in view of achieving energy saving and expanding fixable range.

The neutralizing step is a step for neutralizing by applying a neutralizing bias on the electrophotographic photoconductor, and it may be favorably carried out using a neutralizing unit.

The neutralizing unit is not particularly restricted as long as it may apply a neutralizing bias on the electrophotographic photoconductor. It may be appropriately selected from heretofore known neutralizing devices, and a neutralizing lamp and so on is favorably used.

The cleaning step is a step for removing the toner remaining on the electrophotographic photoconductor, and it may be favorably carried out by a cleaning unit. Here, without using a cleaning unit, it is possible to employ a method of aligning the charge of the residual toner with a rubbing member and recovering with the developing roller.

The cleaning unit is not particularly restricted as long as the electrophotographic toner remaining on the electrophotographic photoconductor may be removed, and it may be appropriately selected from heretofore known cleaners. For example, a magnetic brush cleaner, an electrostatic brush cleaner, a magnetic roller cleaner, a blade cleaner, a brush cleaner, a web cleaner and so on may be favorably used.

The recycling step is a step for recycling the toner removed by the cleaning step and recycling it to the developing unit, and it may be favorably carried out by a recycling unit. The recycling unit is not particularly restricted, and heretofore known conveying units may be used.

The controlling step is a step for controlling the respective steps, and it may be favorably carried out by a controlling unit.

The controlling unit is not particularly restricted as long as it may control operations of the respective units, and it may be appropriately selected according to purpose. For example, devices such as sequencer and computer may be used.

Next, the image forming method, the image forming apparatus and the process cartridge of the present invention are explained in detail using diagrams.

Figure 6:
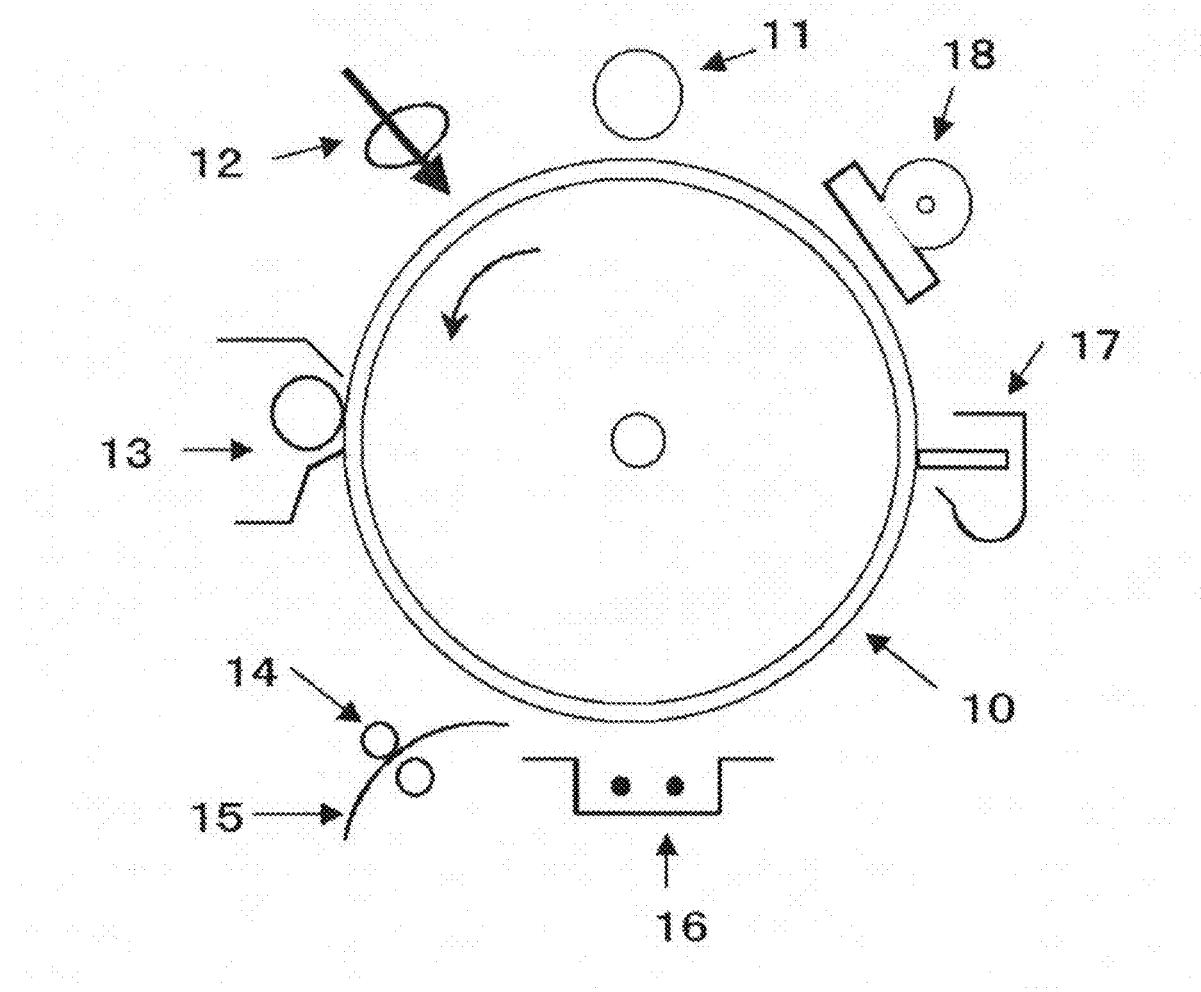
FIG. 6 is a schematic diagram illustrating one example of an electrophotographic process and an image forming apparatus of the present invention.

FIG. 6 is a schematic diagram for explaining the electrophotographic process and the image forming apparatus of the present invention, and examples below also belong to the scope of the present invention.

A photoconductor 10 rotates in a direction of an arrow in FIG. 6, and around the photoconductor 10, a charging member 11, an image exposure member 12, a developing member 13, a transfer member 16, a cleaning member 17, a neutralization member 18 and so on are arranged. Here, there are cases where the cleaning member 17 and the neutralization member 18 are omitted.

The image forming apparatus basically operates as follows. By the charging member 11, a surface of the photoconductor 10 is almost uniformly charged. Next, by the image exposure member 12, an image corresponding to input signals is written with a light, and an electrostatic latent image is formed. Next, by the developing member 13, this electrostatic latent image is developed, and a toner image is formed on a surface of the photoconductor. The formed toner image is transferred by a transfer member on transfer paper 15 sent by a conveying roller 14 to a transfer position. This toner image is fixed on the transfer paper by a fixing apparatus not shown. A part of the toner which is not transferred on the transfer paper is cleaned by the cleaning member 17. Next, the charge remaining on the photoconductor is neutralized by the neutralization member 18, and the operation moves to a next cycle.

As illustrated in FIG. 6, the photoconductor 10 has a shape of a drum, but it may be sheet-shaped, or it may be an endless belt. As the charging member 11 and the transfer member 16, a corotron, a scorotron, a solid charger (solid state charger), and in addition, a roller-shaped charging member and a brush-shaped charging member, and so on may be used, and any heretofore known device may be used.

Meanwhile, as light sources including the image exposure member 12, the neutralization member 18 and so on, a light-emitting element in general may be used, including a fluorescent lamp, a tungsten lamp, a halogen lamp, a mercury lamp, a sodium lamp, a light-emitting diode (LED), a laser diode (LD), a electroluminescence (EL) and so on.

Among these, the LD (laser diode) or the LED (light-emitting diode) are mainly used for the digital method.

In order to irradiate a light only of desired wavelength region, various filters including a sharp-cut filter, a band-pass filter, a near-infrared-cut filter, a dichroic filter, an interference filter, a light-balancing filter and so on may also be used.

By providing a step combined with light irradiation such as transfer step, neutralizing step, cleaning step and pre-exposure step, the light source, a light is irradiated on the photoconductor 10 from the light source. Here, an effect of fatigue on the photoconductor 10 by an exposure on the photoconductor 10 in the neutralizing step is large, which in particular may cause reduction of charge or increase of residual potential.

Accordingly, there are cases where neutralization is possible by applying a reverse bias in the charging step or the cleaning step instead of neutralization by exposure, which may be effective in view of enhanced durability of the photoconductor.

When the electrophotographic photoconductor 10 is positively (negatively) charged and image exposure is carried out, a positive (negative) electrostatic latent image is formed on a surface of the photoconductor. When this is developed using a toner (electroscopic particles) having a negative (positive) polarity, a positive image is obtained. Also, when it is developed using a toner having a positive (negative) polarity, a negative image is obtained.

A heretofore known method is applied to the developing unit, and also a heretofore known method is used for the neutralizing unit.

Among contaminants which adhere to a surface of the photoconductor, discharging substances generated by charging or external additives included in the toner are easily affected by humidity, causing an abnormal image, and paper dust is one of the causative substance of such an abnormal image. Adhesion of these substances on the photoconductor not only makes an abnormal image to occur more easily but also tends to reduce abrasion resistance or cause uneven wear. Thus, because of the above reason, a configuration that the photoconductor and paper are not directly in contact with each other is more preferable in view of high image quality.

The toner developed by the developing member 13 on the photoconductor 10 is transferred to transfer paper 15. The toner is not completely transferred; rather, a part of the toner remains on the photoconductor 10. Such a toner is removed from the photoconductor 10 by the cleaning member 17.

As this cleaning member, heretofore known ones including a cleaning blade and a cleaning brush is used. Also, there are cases the both are used in combination.

The photoconductor of the present invention may be applied to a small-diameter photoconductor because it has achieved high light and high stability. Thus, as an image forming apparatus or a method thereof with which the photoconductor is used more effectively, it is extremely effectively used with a so-called tandem image forming apparatus, which is equipped with a plurality of photoconductor corresponding to developing units corresponding to toners of plurality of colors and carries out a parallel operation thereby. In the tandem image forming apparatus, at least four (4) colors of toners, yellow (Y), magenta (M), cyan (C), black (K), required for full-color printing and developing units which hold them are disposed, and further at least four (4) photoconductors which corresponds thereto are disposed. Accordingly, it enables an extremely fast full-color printing compared to a conventional image forming apparatus for full-color printing.

Figure 7:
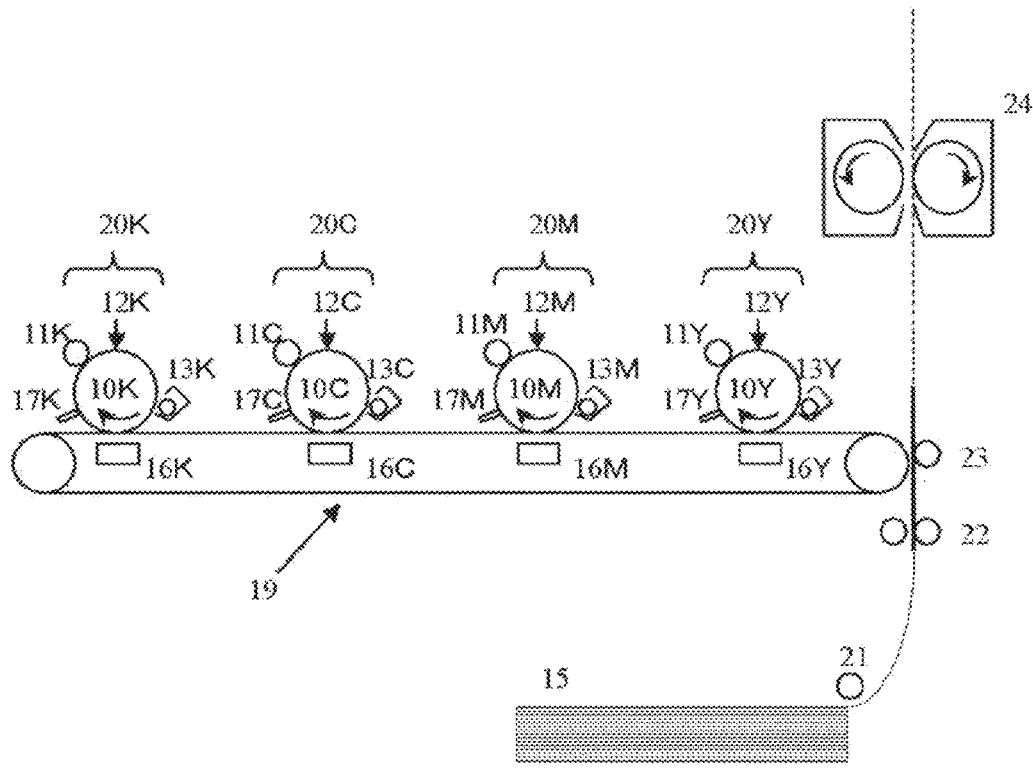
FIG. 7 is a schematic diagram illustrating another example of an electrophotographic process and an image forming apparatus of the present invention.

FIG. 7 is a schematic diagram for explaining a tandem full-color electrophotographic device of the present invention, and a modification described below also belongs to the scope of the present invention.

In FIG. 7, photoconductors 10C (cyan), 10M (magenta), 10Y (yellow) and 10K (black) are drum-shaped photoconductors 10. These photoconductors 10C, 10M, 10Y and 10K rotate in a direction of arrows in the diagram, and around them, at least in an order of rotation, charging members 11C, 11M, 11Y and 11K, developing members 13C, 13M, 13Y and 13K, and cleaning members 17C, 17M, 17Y and 17K are arranged.

Between the charging members 11C, 11M, 11Y and 11K and the developing members 13C, 13M, 13Y and 13K and from a back side of photoconductors 10, laser lights 12C, 12M, 12Y and 12K are irradiated from an exposure member not shown, and electrostatic latent images are formed on the photoconductor 10C, 10M, 10Y and 10K.

Thereafter, four (4) image forming elements 20C, 20M, 20Y and 20K around the photoconductor 10C, 10M, 10Y and 10K are arranged in parallel along a transfer conveying belt 19 as a transfer material conveying unit.

The transfer conveying belt 19 is in contact with the photoconductors 10C, 10M, 10Y and 10K between the developing members 13C, 13M, 13Y and 13K and the cleaning members 17C, 17M, 17Y and 17K of the image forming units 20C, 20M, 20Y and 20K. On a back side (back surface) of the transfer conveying belt 19 corresponding to a side of the photoconductor 10, transfer members 16C, 16M, 16Y and 16K are disposed for applying a transfer bias. The image forming elements 20C, 20M, 20Y and 20K are different in terms of the colors of the toners within the developing apparatus, and other than that, they have identical configuration.

In a color electrophotographic device of a configuration illustrated in FIG. 7, image forming operations are carried out as follows. First, in the respective image forming elements 20C, 20M, 20Y and 20K, the photoconductors 10C, 10M, 10Y and 10K are charged by the charging members 11C, 11M, 11Y and 11K which rotate in a direction taken around by the photoconductors 10. Next, at exposure units disposed outside the photoconductors 10 (not shown), electrostatic latent images corresponding to images of respective colors to be formed is formed by the laser lights 12C, 12M, 12Y and 12K.

Next, latent images are developed by the developing members 13C, 13M, 13Y and 13K, and toner images are formed. The developing members 13C, 13M, 13Y and 13K are developing member which carries out development with toners of C (cyan), M (magenta), Y (yellow) and K (black), respectively, and the toner images of the respective colors formed on the four (4) photoconductors 10C, 10M, 10Y and 10K are superimposed on the transfer belt 19.

Transfer paper 15 is sent out from a tray by a paper-feed roller 21, stopped temporarily at a pair of registration rollers 22, and sent to a transfer member 23 at a timing of image formation on the photoconductors. The toner image held on the transfer belt 19 is transferred on the transfer paper 15 by an electric field formed by a potential difference between a transfer bias applied on the transfer member 23 and the transfer belt 19. The toner image transferred on the transfer paper is conveyed, and the toner is fixed on the transfer paper by a fixing member 24, and discharged to a discharging unit not shown. Also, residual toners which are not transferred at the transfer unit and remaining on the photoconductors 10C, 10M, 10Y and 10K are collected by cleaning members 17C, 17M, 17Y and 17K provided in the respective units.

An intermediate transfer method illustrated in FIG. 7 is particularly effective in an image forming apparatus with which full-color printing is possible. After forming a plurality of toner images once on an intermediate transfer body, the images are transferred to paper at once, which allows easier control of preventing color shift and is effective for high image quality.

There are various materials and shapes such as drum and belt for the intermediate transfer body, and in the present invention, it is possible to use any conventionally heretofore known intermediate transfer body may be used. This is effective and useful for enhanced durability and image quality of the photoconductor.

Here, in the example of FIG. 7, the image forming elements are aligned in the order of C (cyan), M (magenta), Y (yellow) and K (black) from an upstream side to a downstream side of the transfer paper conveying direction. However, the order is not limited thereto, and the color order may be arbitrarily determined. Also, when a document of only a black color is to be created, it is particularly effective to use a mechanism that the image forming element 20C, 20M and 20Y other than the black color halt in the present invention.

The image forming unit described above may be incorporated in a copying apparatus, a facsimile, or a printer in a fixed manner, or it may be incorporated in these apparatuses in a form of a process cartridge.

<Process Cartridge>

The process cartridge used in the present invention includes: an electrophotographic photoconductor; a developing unit which develops an electrostatic latent image formed on the electrophotographic photoconductor using a toner to form a visible image; and a charging unit, a cleaning unit, a transfer unit or a neutralizing unit, or any combination thereof, wherein it is detachably attached to an image forming apparatus main body, and wherein the electrophotographic photoconductor of the present invention is used as the electrophotographic photoconductor.

Figure 8:
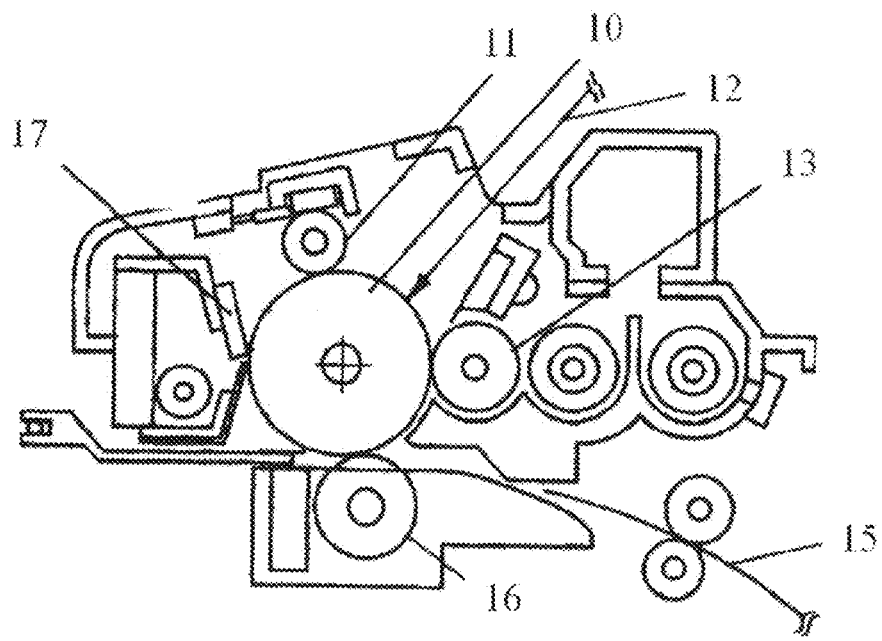
FIG. 8 is a schematic diagram illustrating one example of a process cartridge of the present invention.

The process cartridge is one piece of apparatus (component), as to illustrated in FIG. 8, including internally a photoconductor 10, and further including a charging member 11, an image exposure member 12, a developing member 13, a transfer member 16, a cleaning member 17, and a neutralization member.

High-speed full-color printing is possible with the tandem image forming apparatus because it may transfer a plurality of toner images at once.

However, since at least four (4) of the electrophotographic photoconductors are required, increase in the size of the apparatus cannot be avoided. In addition, depending on an amount of a toner used, an amount of wear varied between the photoconductors, which reduced reproducibility of the colors or causes an abnormal image. Thus, there are many problems with the apparatus.

The image forming apparatus, image forming method and process cartridge of the present invention uses the electrophotographic photoconductor of the present invention, and a small-diameter photoconductor may be applied since it has achieved high light sensitivity and high stability. Since effects of increase in residual or degradation of potential sensitivity are suppressed, difference in the residual potential and sensitivity in repeated use over time is small even though amounts of usage of the four (4) electrophotographic photoconductors vary. Thus, a full-color image having superior color reproducibility may be obtained even after repeated use for a long period of time.

EXAMPLES

Hereinafter, the present invention is explained in reference to examples, but the present invention is not to be limited by the examples. Here, parts denote parts by mass, and % denotes % by mass.

Example 1

Synthesis Example 1 (Synthesis of Compound No. I-4)

Under a stream of argon, 12.06 g (40.0 mmol) of an aldehyde compound represented by Structural Formula (M1) below, 8.68 g (44.0 mmol) of dibenzylamine, 13.39 g (60.0 mmol) of sodium triacetoxyborohydride, and 100 mL of tetrahydrofuran (THF) were stirred at a room temperature for 2 hours.

Structural Formula (M1)

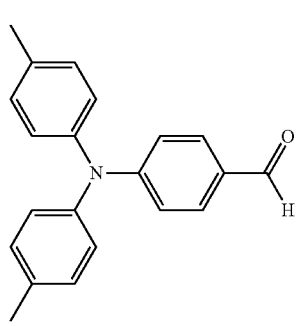

After completion of a reaction, 100 mL of a 1-M aqueous solution of sodium carbonate was poured into the content, which was stirred for 30 minutes and extracted with ethyl acetate. An organic layer was washed with water and concentrated under a reduced pressure to distill the solvent, and a yellow oily substance was obtained. This was subjected to a silica gel column chromatography process [eluent: toluene/cyclohexane=1:1 (v/v)], and obtained white crystals were recrystallized with a mixed solvent of ethyl acetate and methanol. Thereby, a diamine compound of Compound No. I-4 represented by Structural Formula (M2) below was obtained as colorless rod-shaped crystals. A yield amount was 16.05 g, a yield ratio was 83.1%, and a melting point was 99.0° C. to 100.0° C.

Structural Formula (M2)

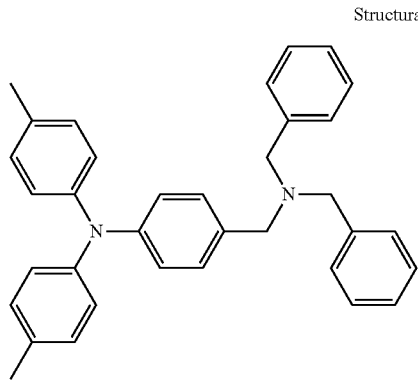

The obtained crystals were analyzed using an LC-MS, and a peak of 483.52 corresponding to a molecular ion [M+H]$^+$ that a proton was attached to the objective diamine compound of Compound No. 4 (calculated molecular weight: 482.66) was observed.

Figure 9:
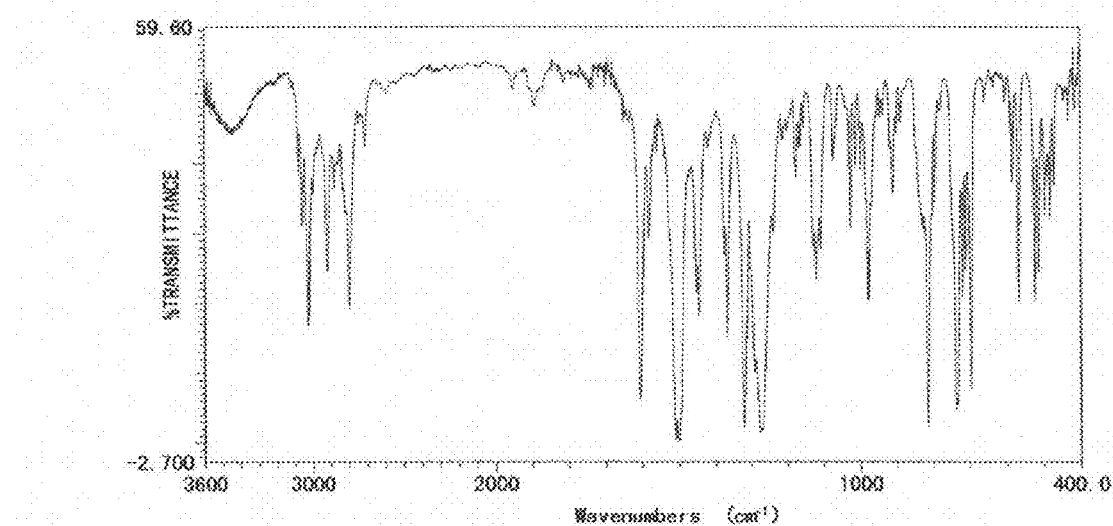
FIG. 9 is an infrared absorption spectrum of a diamine compound obtained in Example 1.

An infrared absorption spectrum (KBr tablet method) is illustrated in FIG. 9.

Example 2

Synthesis Example 2 (Synthesis of Compound No. I-5)

Under a stream of argon, 5.00 g (16.6 mmol) of an aldehyde compound represented by Structural Formula (M3), 2.75 g (18.3 mmol) of N-ethyl-p-toluidine, 5.18 g (23.2 mmol) of sodium triacetoxyborohydride, and 70 mL of tetrahydrofuran (THF) were stirred at an internal temperature of 25° C. for 22 hours.

Structural Formula (M3)

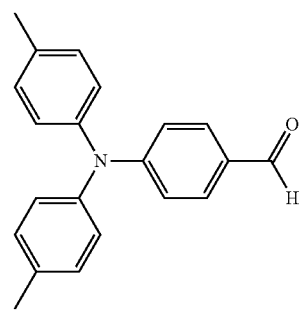

After 22 hours, 50 mL of a 1-M aqueous solution of sodium carbonate was poured into the content, which was stirred for 30 minutes and extracted with ethyl acetate. An organic layer was washed with water, concentrated and subjected to a silica gel column chromatography process [eluent: toluene], and a diamine compound of Compound No. I-5 represented by Structural Formula (M4) was obtained as a colorless viscous liquid. A yield amount was 2.59 g (6.2 mmol), and a yield ratio was 37.3%.

Structural Formula (M4)

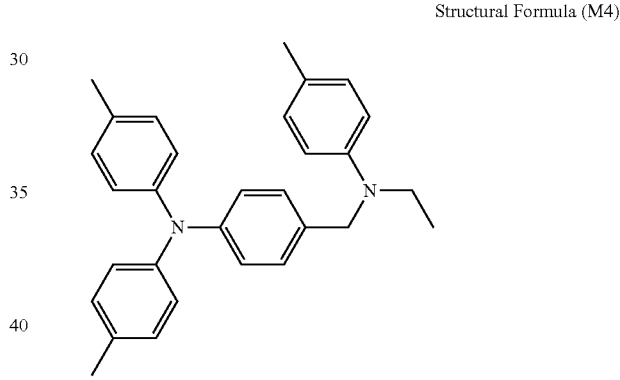

The obtained colorless viscous liquid was analyzed using an LC-MS, and a peak of 421.60 corresponding to a molecular ion [M+H]$^+$ that a proton was attached to the objective diamine compound of Compound No. I-5 (calculated molecular weight: 420.59) was observed.

Figure 10:
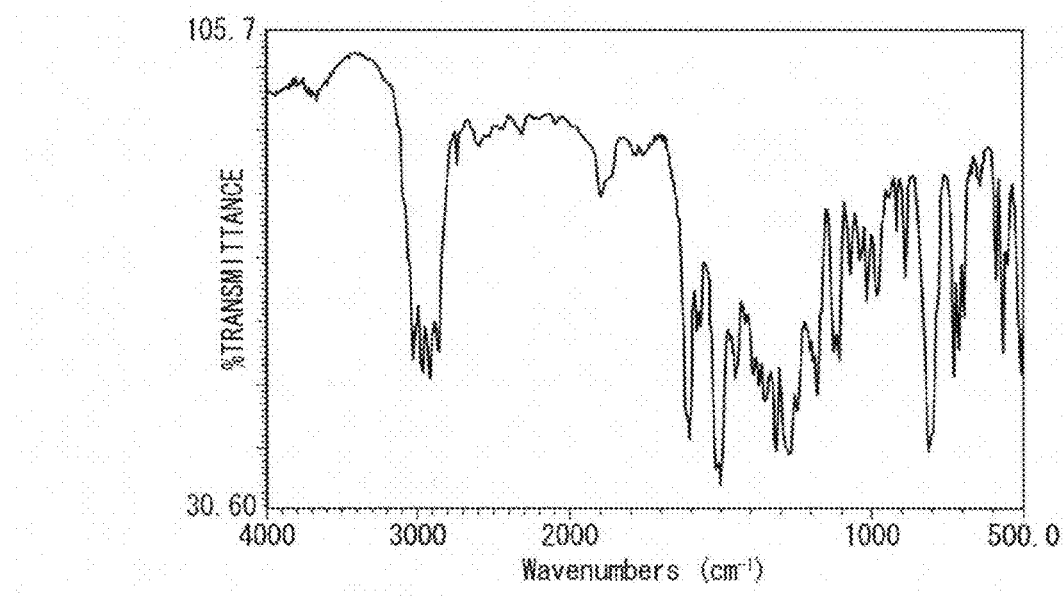
FIG. 10 is an infrared absorption spectrum of a diamine compound obtained in Example 2.

An infrared absorption spectrum (NaCl method) is illustrated in FIG. 10.

Example 3

Synthesis Example 3 (Synthesis of Compound No. I-6)

Under a stream of argon, 5.00 g (16.6 mmol) of an aldehyde compound represented by Structural Formula (M5), 2.69 g (18.3 mmol) of N-ethylbenzylamine, 5.18 g (23.2 mmol) of sodium triacetoxyborohydride, and 70 mL of tetrahydrofuran (THF) were stirred at an internal temperature of 25° C. for 4 hours.

Structural Formula (M5)

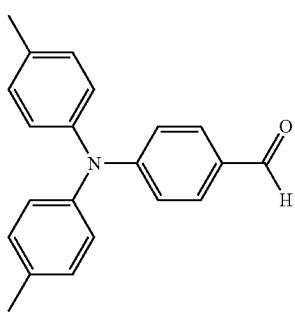

After 4 hours, 50 mL of a 1-M aqueous solution of sodium carbonate was poured into the content, which was stirred for 30 minutes and extracted with ethyl acetate. An organic layer was washed with water, concentrated, and subjected to a silica gel column chromatography process [eluent: toluene], and a diamine compound of Compound No. I-6 represented by Structural Formula (M6) below as a colorless viscous liquid. A yield amount was 4.56 g (10.8 mmol), and a yield ratio was 65.1%.

Structural Formula (M6)

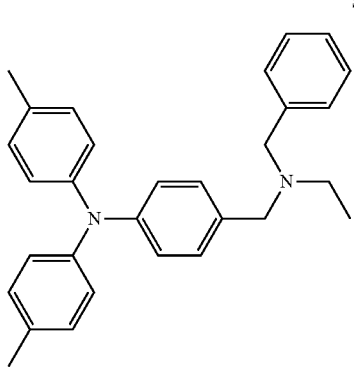

The obtained colorless viscous liquid was analyzed using an LC-MS, and a peak of 421.52 corresponding to a molecular ion $[M+H]^+$ that a proton was attached to the objective diamine compound of Compound No. I-6 (calculated molecular weight: 420.59) was observed.

Figure 11:
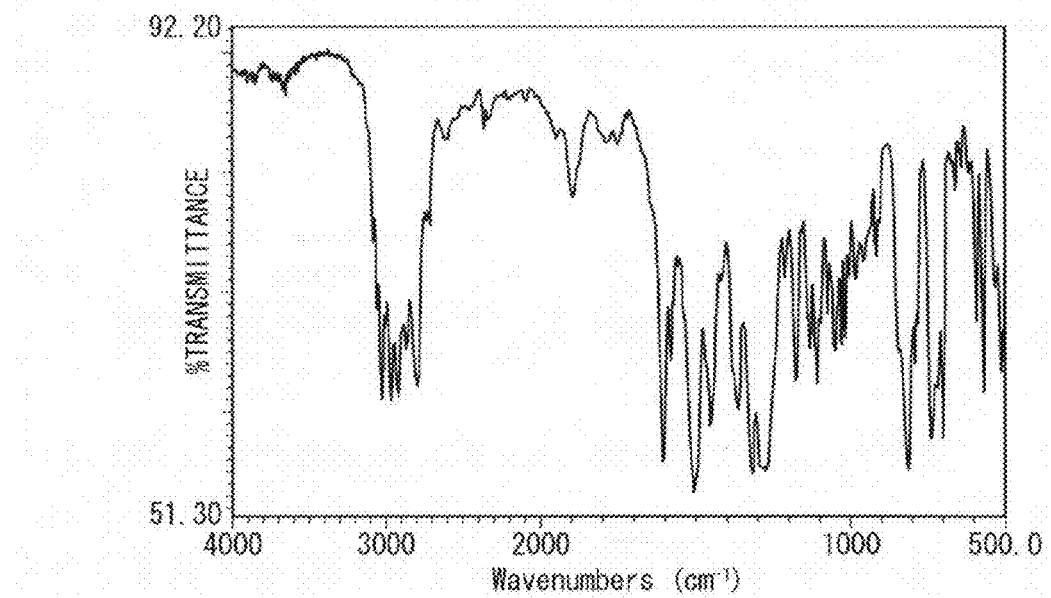
FIG. 11 is an infrared absorption spectrum of a diamine compound obtained in Example 3.

An infrared absorption spectrum (NaCl method) is illustrated in FIG. 11.

Example 4

Figure 12:
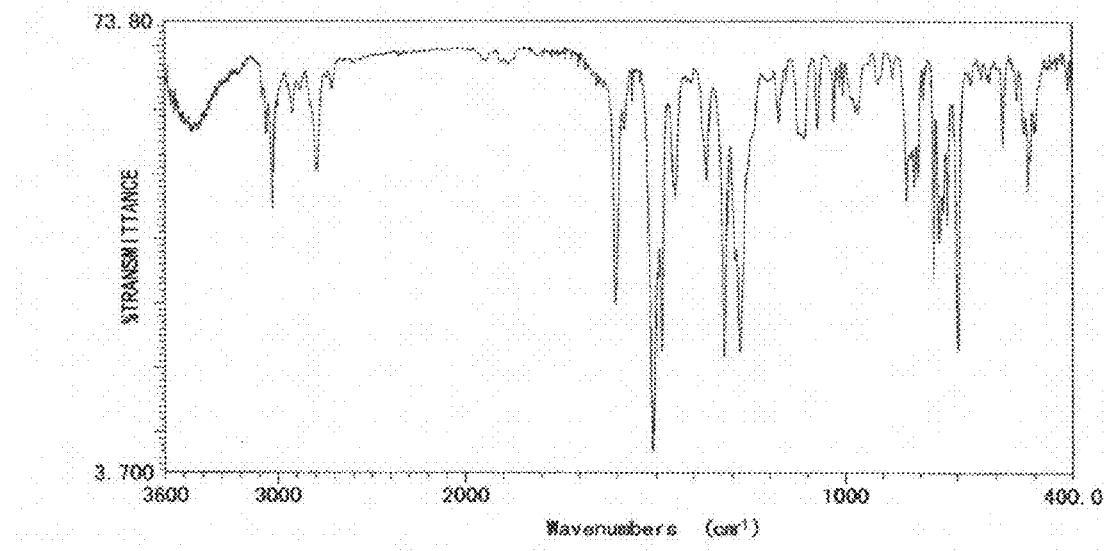
FIG. 12 is an infrared absorption spectrum of a diamine compound obtained in Example 4.

Compound No. I-11 below was synthesized by operating similarly to Example 1. Results are shown in Table 2 below, and an infrared absorption spectrum (KBr tablet method) is illustrated in FIG. 12.

Example 5

Figure 13:
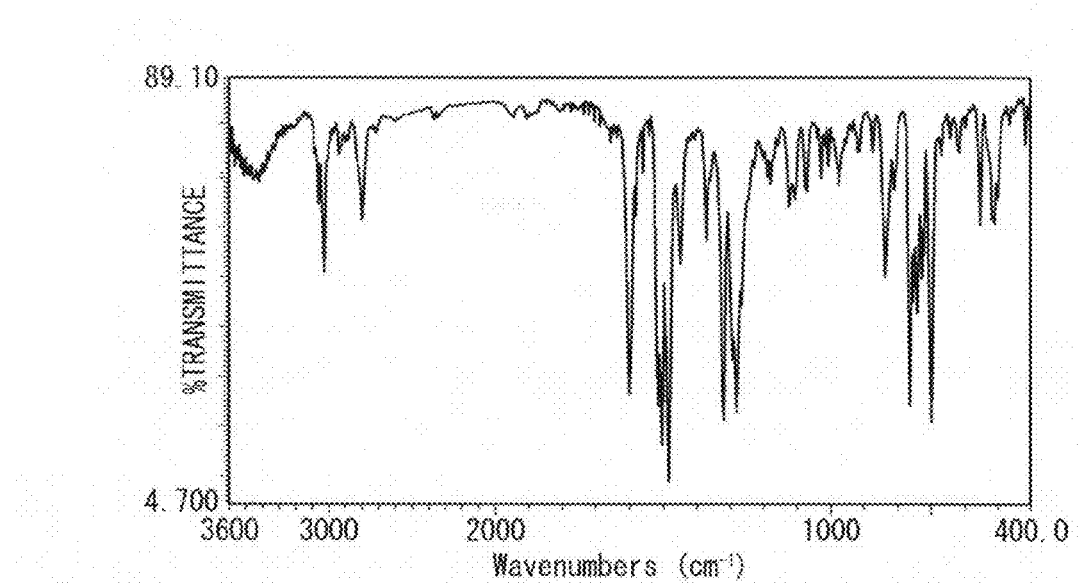
FIG. 13 is an infrared absorption spectrum of a diamine compound obtained in Example 5.

Results are shown in Table 2 below, and an infrared absorption spectrum (KBr tablet method) is illustrated in FIG. 13.

Example 6

Figure 14:
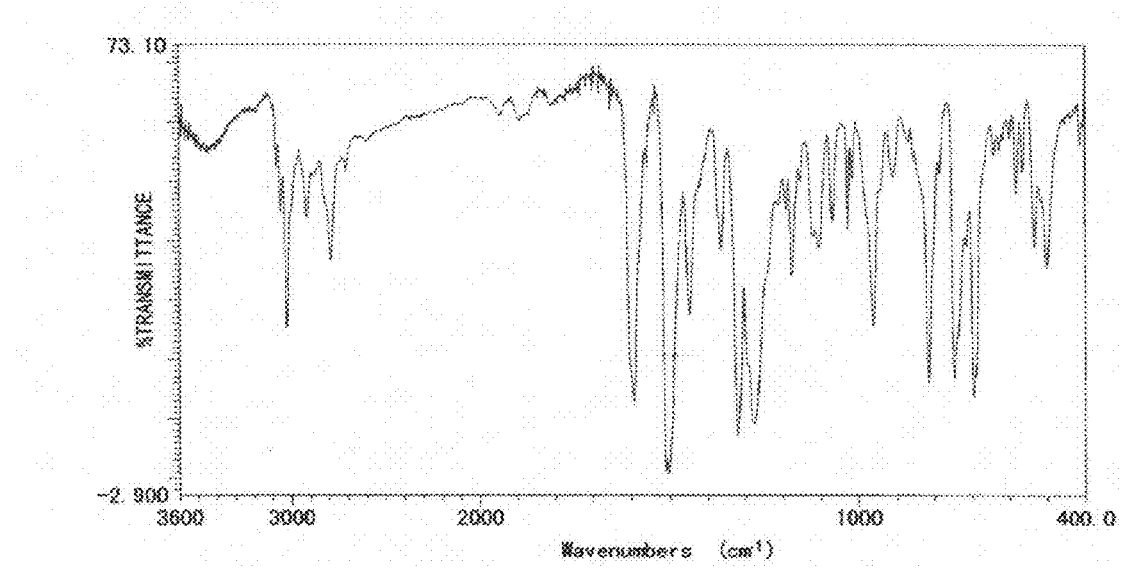
FIG. 14 is an infrared absorption spectrum of a diamine compound obtained in Example 6.

Compound No. I-29 below was synthesized by operating similarly to Example 1. Results are shown in Table 2 below, and an infrared absorption spectrum (KBr tablet method) is illustrated in FIG. 14.

Example 7

Figure 15:
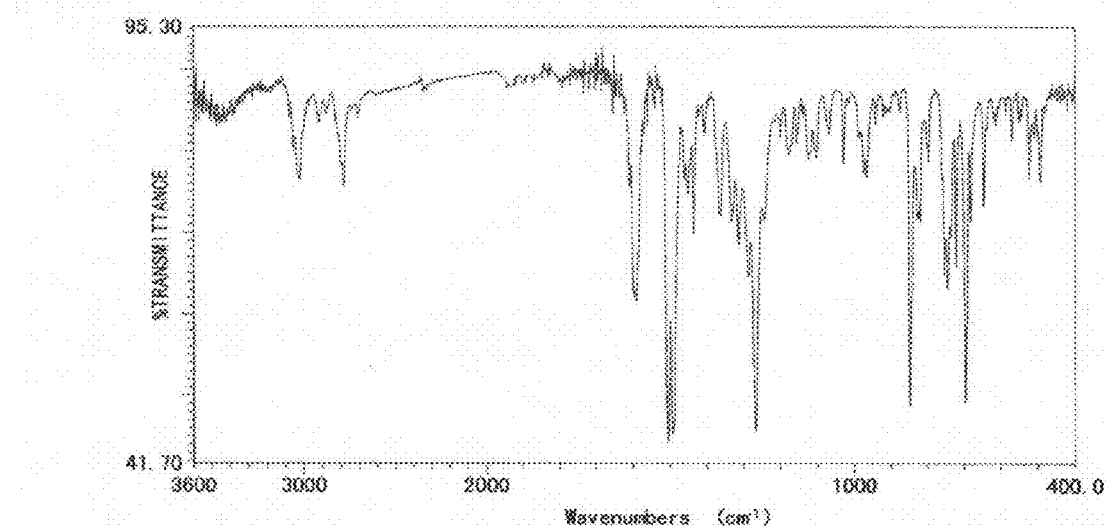
FIG. 15 is an infrared absorption spectrum of a diamine compound obtained in Example 7.

Compound No. I-43 below was synthesized by operating similarly to Example 1. Results are shown in Table 2 below, and an infrared absorption spectrum (KBr tablet method) is illustrated in FIG. 15.

TABLE 2

| Example No. | Compound No. | Yield Ratio (%) | Melting Point (° C.) |
|---|---|---|---|
| 4 | I-11 | 56.0 | 87.0-89.0 |
| 5 | I-16 | 67.0 | 154.0-155.0 |
| 6 | I-29 | 52.0 | Yellow viscous liquid |
| 7 | I-43 | 72.0 | 138.0-139.0 |

Example 8 to Example 15

Also, similarly to Example 1, diamine compounds of Table 3 were synthesized, identified and used in manufacturing electrophotographic photoconductors described hereinafter.

TABLE 3

| Example No. | Diamine compound No. | Photoconductor used |
|---|---|---|
| Example 8 | I-1 | Used in Photoconductors 1, 35, 111 |
| Example 9 | I-2 | Used in Photoconductors 3, 36, 120 |
| Example 10 | I-3 | Used in Photoconductors 3, 36, 120 |
| Example 11 | I-21 | Used in Photoconductors 9, 42 |
| Example 12 | I-22 | Used in Photoconductors 10, 43 |
| Example 13 | I-25 | Used in Photoconductors 11, 44 |
| Example 14 | I-26 | Used in Photoconductors 45, 36, 144, 150 |
| Example 15 | I-36 | Used in Photoconductors 14, 47 |

Example 16

Synthesis Example 8 (Synthesis of Compound No. II-3)

Under a stream of argon, 20 mL of tetrahydrofuran (THF) was added to 1.58 g (5.00 mmol) of a diformyl compound represented by the following structural formula, 2.17 g (11.0 mmol) of dibenzylamine, 2.54 g (12.0 mmol) of [NaBH(OOCCH$_3$)$_3$], and 0.66 g of acetic acid, which was stirred at a room temperature for 3 hours.

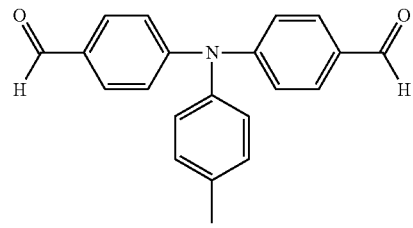 [SMILES: Cc1ccc(N(c2ccc(C=O)cc2)c2ccc(C=O)cc2)cc1]

A saturated aqueous solution of sodium hydrogen carbonate was poured into the content until it became neutral, which was stirred for 30 minutes and extracted with ethyl acetate. An extracted organic layer was washed with water, concentrated under a reduced pressure, and subjected to a silica gel column chromatography process [eluent: toluene], and 2.97 g of a triamine compound of Compound No. II-3 represented by the following structural formula was obtained as a transparent oily substance (a yield ratio of 87.6%).

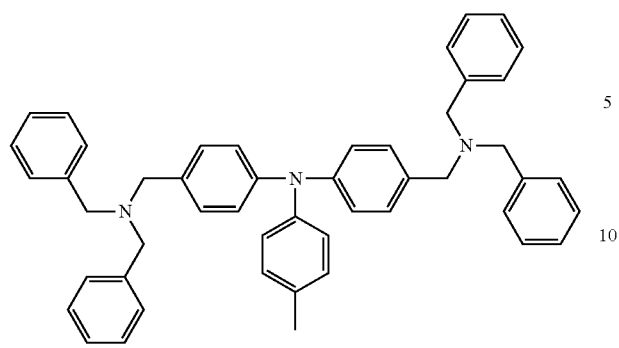

Figure 16:
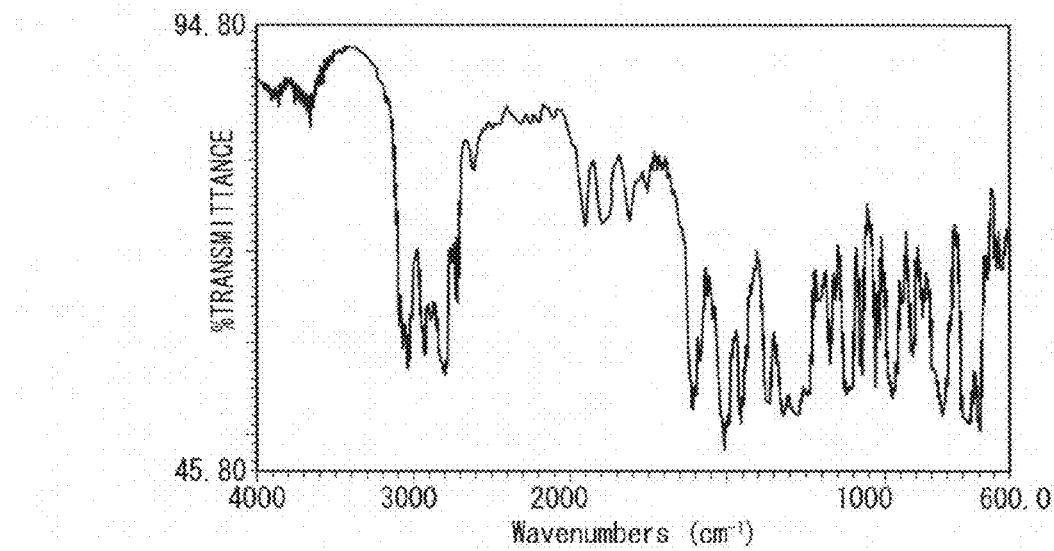
FIG. 16 is an infrared absorption spectrum of a triamine compound obtained in Example 16.

The obtained crystals were analyzed using an LC-MS, and a peak of 678.38 corresponding to a molecular ion $[M+H]^+$ that a proton was attached to the objective triamine compound of Compound No. II-3 (calculated molecular weight: 677.92) was observed. An infrared absorption spectrum (KBr tablet method) is illustrated in FIG. 16.

Example 17 to Example 39

Also, similarly to Example 16, triamine compounds of Table 4 below were synthesized, identified and used in manufacturing electrophotographic photoconductors described hereinafter.

TABLE 4

| Example No. | Triamine compound No. | Photoconductor used |
|---|---|---|
| Example 17 | II-1 | Used in Photoconductors 26, 50 |
| Example 18 | II-2 | Used in Photoconductors 27, 51 |
| Example 19 | II-4 | Used in Photoconductors 28, 52 |
| Example 20 | II-5 | Used in Photoconductors 29, 53 |
| Example 21 | II-6 | Used in Photoconductors 114, 122 |
| Example 22 | II-11 | Used in Photoconductors 30, 54 |
| Example 23 | II-14 | Used in Photoconductors 31, 55 |
| Example 24 | II-16 | Used in Photoconductors 32, 56, 72 |
| Example 25 | II-17 | Used in Photoconductors 94, 115, 123, 128, 137 |
| Example 26 | II-18 | Used in Photoconductors 33, 57, 152 |
| Example 27 | II-21 | Used in Photoconductors 34, 58 |
| Example 28 | II-22 | Used in Photoconductor 73 |
| Example 29 | II-23 | Used in Photoconductors 35, 59 |
| Example 30 | II-24 | Used in Photoconductor 138 |
| Example 31 | II-26 | Used in Photoconductors 95, 116 |
| Example 32 | II-27 | Used in Photoconductors 36, 60 |
| Example 33 | II-29 | Used in Photoconductors 37, 61 |
| Example 34 | II-30 | Used in Photoconductor 139 |
| Example 35 | II-31 | Used in Photoconductors 38, 62 |
| Example 36 | II-36 | Used in Photoconductor 129 |
| Example 37 | II-37 | Used in Photoconductor 74 |
| Example 38 | II-39 | Used in Photoconductor 96 |
| Example 39 | II-41 | Used in Photoconductors 39, 63 |

Example 40

Synthesis Example 9 (Synthesis of Compound No. III-10)

Under a stream of argon, 40 mL of tetrahydrofuran (THF) was added to 3.29 g (10.0 mmol) of a triformyl compound represented by the following structural formula, 6.51 g (33.0 mmol) of dibenzylamine, and 10.04 g (45.0 mmol) of sodium triacetoxyborohydride [NaBH(OOCCH$_3$)$_3$], which was stirred at a room temperature for 3 hours.

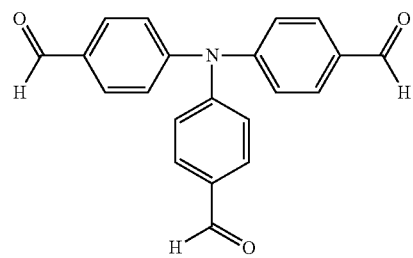 [SMILES: O=Cc1ccc(N(c2ccc(C=O)cc2)c2ccc(C=O)cc2)cc1]

A saturated aqueous solution of sodium hydrogen carbonate was poured into the content until it became neutral, which was stirred for 30 minutes and extracted with ethyl acetate. An extracted organic layer was washed with water and concentrated under a reduced pressure, and pale yellow crystals were obtained. It was subjected to a silica gel column chromatography process [eluent: toluene]. Obtained white crystals were recrystallized with a mixed solvent of ethyl acetate and ethanol, and a tetramine compound of Compound No. III-10 represented by the following structural formula was obtained as colorless needle crystals. A yield amount was 5.32 g, a yield ratio was 60.9%, and melting point was 137.0° C. to 138.0° C. Also, in order to use for electrophotographic photoconductors described hereinafter, a tetramine compound of Compound No. 111-2 and a tetramine compound of Compound No. III-23 were similarly synthesized and identified.

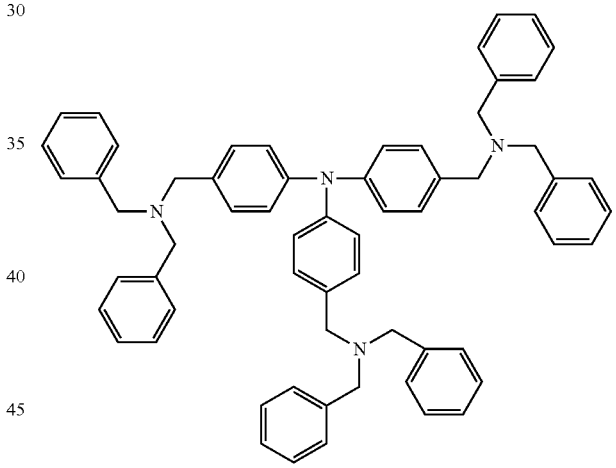

Figure 17:
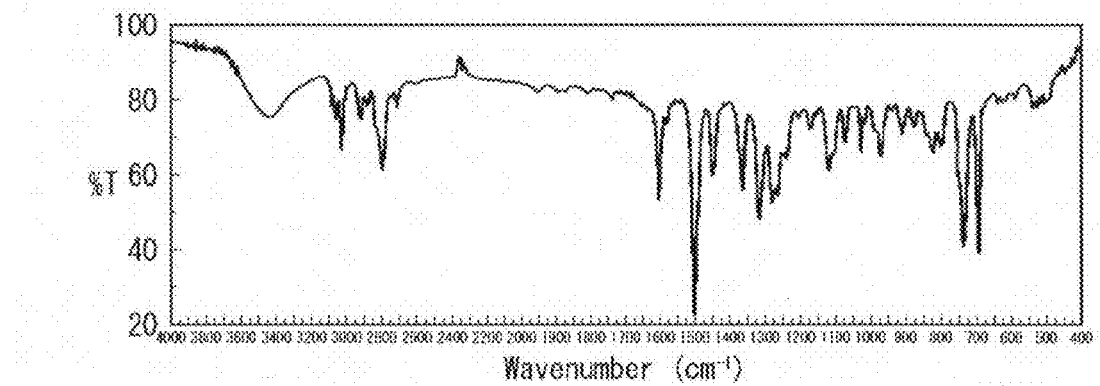
FIG. 17 is an infrared absorption spectrum of a tetramine compound obtained in Example 40.

The obtained crystals were analyzed using an LC-MS, and a peak of 873.49 corresponding to a molecular ion $[M+H]^+$ that a proton was attached to the objective tetramine compound of Compound No. III-10 (calculated molecular weight: 873.18) was observed. An infrared absorption spectrum (KBr tablet method) is illustrated in FIG. 17.

Example 41

Electrophotographic Photoconductor 1

On an aluminum cylinder, an undercoat layer coating solution, a charge generation layer coating solution, and a charge transport layer coating solution having the following compositions were sequentially applied by a dip-coating method followed by drying, and an undercoat layer having a thickness of 3.5 μm, a charge generation layer having a thickness of 0.2 μm, and a charge transport layer having a thickness of 20 μm were formed (Photoconductor 1).

(Undercoat Layer Coating Solution)

| Titanium dioxide powder: | 400 parts |
|---|---|
| Melamine resin: | 65 parts |
| Alkyd resin: | 120 parts |
| 2-Butanone: | 400 parts |

(Charge Generation Layer Coating Solution)

| Fluorenone bisazo pigment of Structural Formula (46) below: | 12 parts |
|---|---|
| Polyvinyl butyral (BX-1, manufactured by Sekisui Chemical Co., Ltd.): | 5 parts |
| 2-Butanone: | 200 parts |
| Cyclohexanone: | 400 parts |

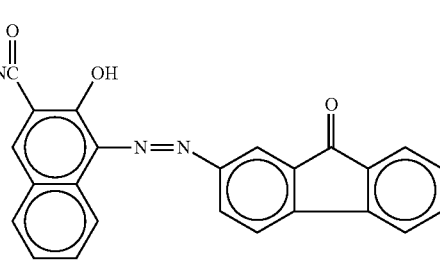

Structural Formula (46)

(Charge Transport Layer Coating Solution)

| Polycarbonate resin (Z POLYCA, manufactured by Teijin Chemicals Ltd.): | 10 parts |
|---|---|
| Diamine compound of Exemplary Compound No. I-4: | 10 parts |
| Tetrahydrofuran: | 100 parts |

Thus prepared Electrophotographic Photoconductor 1 was mounted on a cartridge for an electrophotographic process, and using remodeled IMAGIO MP 2550 manufactured by Ricoh Company, Ltd. which employed a corona charging method (scorotron type) as a charging method and a 655-nm laser diode (LD) as an image exposure light source with a dark potential set to 800(−V), a repeated test corresponding to continuous printing of 100,000 sheets in total was carried out. At that time, images and light potentials at an initial stage and after the repeated test were evaluated.

Also, regarding an image, 10 sheets of a dot image having a pixel density of 600 dpi×600 dpi and an image density of 5% were continuously printed out, and a dot shape thereof was observed by a stereomicroscope. A quality of the image was evaluated in the following five (5) stages (5 was superior, and 1 was inferior). Results are shown in Table 5-1.

(Image Quality Evaluation Criteria)

5: Satisfactory with clear outline.

4: Compared to 5, decrease in image density (small) was observed.

3: Compared to 5, decrease in image density (medium) was observed.

2: Compared to 5, decrease in image density (large) was observed.

1: Compared to 5, decrease in image density (large) was observed, and moreover, the image could not be determined.

Example 42

Electrophotographic Photoconductor 2

Electrophotographic Photoconductor 2 was prepared in the same manner as Example 41 except that a diamine compound of Exemplary Compound No. I-1 shown in Table 5-1 was used instead of the diamine compound of Exemplary Compound No. I-4 in Example 41, and it was evaluated similarly to Example 41. Results are shown in Table 5-1.

Example 43

Electrophotographic Photoconductor 3

Electrophotographic Photoconductor 3 was prepared in the same manner as Example 41 except that a diamine compound of Exemplary Compound No. I-2 shown in Table 5-1 was used instead of the diamine compound of Exemplary Compound No. I-4 in Example 41, and it was evaluated similarly to Example 41. Results are shown in Table 5-1.

Example 44

Electrophotographic Photoconductor 4

Electrophotographic Photoconductor 4 was prepared in the same manner as Example 41 except that a diamine compound of Exemplary Compound No. I-3 shown in Table 5-1 was used instead of the diamine compound of Exemplary Compound No. I-4 in Example 41, and it was evaluated similarly to Example 41. Results are shown in Table 5-1.

Example 45

Electrophotographic Photoconductor 5

Electrophotographic Photoconductor 5 was prepared in the same manner as Example 41 except that a diamine compound of Exemplary Compound No. I-5 shown in Table 5-1 was used instead of the diamine compound of Exemplary Compound No. I-4 in Example 41, and it was evaluated similarly to Example 41. Results are shown in Table 5-1.

Example 46

Electrophotographic Photoconductor 6

Electrophotographic Photoconductor 6 was prepared in the same manner as Example 41 except that a diamine compound

Example 47

Electrophotographic Photoconductor 7

Electrophotographic Photoconductor 7 was prepared in the same manner as Example 41 except that a diamine compound of Exemplary Compound No. I-11 shown in Table 5-1 was used instead of the diamine compound of Exemplary Compound No. I-4 in Example 41, and it was evaluated similarly to Example 41. Results are shown in Table 5-1.

Example 48

Electrophotographic Photoconductor 8

Electrophotographic Photoconductor 8 was prepared in the same manner as Example 41 except that a diamine compound of Exemplary Compound No. I-16 shown in Table 5-1 was used instead of the diamine compound of Exemplary Compound No. I-4 in Example 41, and it was evaluated similarly to Example 41. Results are shown in Table 5-1.

Example 49

Electrophotographic Photoconductor 9

Electrophotographic Photoconductor 9 was prepared in the same manner as Example 41 except that a diamine compound of Exemplary Compound No. I-21 shown in Table 5-1 was used instead of the diamine compound of Exemplary Compound No. I-4 in Example 41, and it was evaluated similarly to Example 41. Results are shown in Table 5-1.

Example 50

Electrophotographic Photoconductor 10

Electrophotographic Photoconductor 10 was prepared in the same manner as Example 41 except that a diamine compound of Exemplary Compound No. I-22 shown in Table 5-1 was used instead of the diamine compound of Exemplary Compound No. I-4 in Example 41, and it was evaluated similarly to Example 41. Results are shown in Table 5-1.

Example 51

Electrophotographic Photoconductor 11

Electrophotographic Photoconductor 11 was prepared in the same manner as Example 41 except that a diamine compound of Exemplary Compound No. I-25 shown in Table 5-1 was used instead of the diamine compound of Exemplary Compound No. I-4 in Example 41, and it was evaluated similarly to Example 41. Results are shown in Table 5-1.

Example 52

Electrophotographic Photoconductor 12

Electrophotographic Photoconductor 12 was prepared in the same manner as Example 41 except that a diamine compound of Exemplary Compound No. I-26 shown in Table 5-1 was used instead of the diamine compound of Exemplary Compound No. I-4 in Example 41, and it was evaluated similarly to Example 41. Results are shown in Table 5-1.

Example 53

Electrophotographic Photoconductor 13

Electrophotographic Photoconductor 13 was prepared in the same manner as Example 41 except that a diamine compound of Exemplary Compound No. I-29 shown in Table 5-1 was used instead of the diamine compound of Exemplary Compound No. I-4 in Example 41, and it was evaluated similarly to Example 41. Results are shown in Table 5-1.

Example 54

Electrophotographic Photoconductor 14

Electrophotographic Photoconductor 14 was prepared in the same manner as Example 41 except that a diamine compound of Exemplary Compound No. I-36 shown in Table 5-1 was used instead of the diamine compound of Exemplary Compound No. I-4 in Example 41, and it was evaluated similarly to Example 41. Results are shown in Table 5-1.

Example 55

Electrophotographic Photoconductor 15

Electrophotographic Photoconductor 15 was prepared in the same manner as Example 41 except that a diamine compound of Exemplary Compound No. I-43 shown in Table 5-1 was used instead of the diamine compound of Exemplary Compound No. I-4 in Example 41, and it was evaluated similarly to Example 41. Results are shown in Table 5-1.

Example 56

Electrophotographic Photoconductor 16

Electrophotographic Photoconductor 16 was prepared in the same manner as Example 41 except that a triamine compound of an exemplary compound shown in Table 5-2 was used instead of the diamine compound of Exemplary Compound No. I-4 in Example 41, and it was evaluated similarly to Example 41. Results are shown in Table 5-2.

Example 57

Electrophotographic Photoconductor 17

Electrophotographic Photoconductor 17 was prepared in the same manner as Example 41 except that a triamine compound of an exemplary compound shown in Table 5-2 was used instead of the diamine compound of Exemplary Compound No. I-4 in Example 41, and it was evaluated similarly to Example 41. Results are shown in Table 5-2.

Example 58

Electrophotographic Photoconductor 18

Electrophotographic Photoconductor 18 was prepared in the same manner as Example 41 except that a triamine compound of an exemplary compound shown in Table 5-2 was used instead of the diamine compound of Exemplary Compound No. I-4 in Example 41, and it was evaluated similarly to Example 41. Results are shown in Table 5-2.

Example 59

Electrophotographic Photoconductor 19

Electrophotographic Photoconductor 19 was prepared in the same manner as Example 41 except that a triamine compound of an exemplary compound shown in Table 5-2 was used instead of the diamine compound of Exemplary Compound No. I-4 in Example 41, and it was evaluated similarly to Example 41. Results are shown in Table 5-2.

Example 60

Electrophotographic Photoconductor 20

Electrophotographic Photoconductor 20 was prepared in the same manner as Example 41 except that a triamine compound of an exemplary compound shown in Table 5-2 was used instead of the diamine compound of Exemplary Compound No. I-4 in Example 41, and it was evaluated similarly to Example 41. Results are shown in Table 5-2.

Example 61

Electrophotographic Photoconductor 21

Electrophotographic Photoconductor 21 was prepared in the same manner as Example 41 except that a triamine compound of an exemplary compound shown in Table 5-2 was used instead of the diamine compound of Exemplary Compound No. I-4 in Example 41, and it was evaluated similarly to Example 41. Results are shown in Table 5-2.

Example 62

Electrophotographic Photoconductor 22

Electrophotographic Photoconductor 22 was prepared in the same manner as Example 41 except that a triamine compound of an exemplary compound shown in Table 5-2 was used instead of the diamine compound of Exemplary Compound No. I-4 in Example 41, and it was evaluated similarly to Example 41. Results are shown in Table 5-2.

Example 63

Electrophotographic Photoconductor 23

Electrophotographic Photoconductor 23 was prepared in the same manner as Example 41 except that a triamine compound of an exemplary compound shown in Table 5-2 was used instead of the diamine compound of Exemplary Compound No. I-4 in Example 41, and it was evaluated similarly to Example 41. Results are shown in Table 5-2.

Example 64

Electrophotographic Photoconductor 24

Electrophotographic Photoconductor 24 was prepared in the same manner as Example 41 except that a triamine compound of an exemplary compound shown in Table 5-2 was used instead of the diamine compound of Exemplary Compound No. I-4 in Example 41, and it was evaluated similarly to Example 41. Results are shown in Table 5-2.

Example 65

Electrophotographic Photoconductor 25

Electrophotographic Photoconductor 25 was prepared in the same manner as Example 41 except that a triamine compound of an exemplary compound shown in Table 5-2 was used instead of the diamine compound of Exemplary Compound No. I-4 in Example 41, and it was evaluated similarly to Example 41. Results are shown in Table 5-2.

Example 66

Electrophotographic Photoconductor 26

Electrophotographic Photoconductor 26 was prepared in the same manner as Example 41 except that a triamine compound of an exemplary compound shown in Table 5-2 was used instead of the diamine compound of Exemplary Compound No. I-4 in Example 41, and it was evaluated similarly to Example 41. Results are shown in Table 5-2.

Example 67

Electrophotographic Photoconductor 27

Electrophotographic Photoconductor 27 was prepared in the same manner as Example 41 except that a triamine compound of an exemplary compound shown in Table 5-2 was used instead of the diamine compound of Exemplary Compound No. I-4 in Example 41, and it was evaluated similarly to Example 41. Results are shown in Table 5-2.

Example 68

Electrophotographic Photoconductor 28

Electrophotographic Photoconductor 28 was prepared in the same manner as Example 41 except that a triamine compound of an exemplary compound shown in Table 5-2 was used instead of the diamine compound of Exemplary Compound No. I-4 in Example 41, and it was evaluated similarly to Example 41. Results are shown in Table 5-2.

Example 69

Electrophotographic Photoconductor 29

Electrophotographic Photoconductor 29 was prepared in the same manner as Example 41 except that a triamine compound of an exemplary compound shown in Table 5-2 was used instead of the diamine compound of Exemplary Compound No. I-4 in Example 41, and it was evaluated similarly to Example 41. Results are shown in Table 5-2.

Example 70

Electrophotographic Photoconductor 30

Electrophotographic Photoconductor 30 was prepared in the same manner as Example 41 except that a triamine compound of an exemplary compound shown in Table 5-2 was used instead of the diamine compound of Exemplary Compound No. I-4 in Example 41, and it was evaluated similarly to Example 41. Results are shown in Table 5-2.

Example 71

Electrophotographic Photoconductor 31

Electrophotographic Photoconductor 31 was prepared in the same manner as Example 41 except that a tetramine compound of an exemplary compound shown in Table 5-3 was used instead of the diamine compound of Exemplary Compound No. I-4 in Example 41, and it was evaluated similarly to Example 41. Results are shown in Table 5-3.

Example 72

Electrophotographic Photoconductor 32

Electrophotographic Photoconductor 32 was prepared in the same manner as Example 41 except that a tetramine compound of an exemplary compound shown in Table 5-3 was used instead of the diamine compound of Exemplary Compound No. I-4 in Example 41, and it was evaluated similarly to Example 41. Results are shown in Table 5-3.

Example 73

Electrophotographic Photoconductor 331

Electrophotographic Photoconductor 33 was prepared in the same manner as Example 41 except that a tetramine compound of an exemplary compound shown in Table 5-3 was used instead of the diamine compound of Exemplary Compound No. I-4 in Example 41, and it was evaluated similarly to Example 41. Results are shown in Table 5-3.

TABLE 5-1

| Example No. | Photo-conductor No. | Diamine compound No. | Initial Light potential (-V) | Initial Image quality | After printing 100,000 sheets Light potential (-V) | After printing 100,000 sheets Image quality |
|---|---|---|---|---|---|---|
| 41 | 1 | I-4 | 50 | 5 | 70 | 5 |
| 42 | 2 | I-1 | 60 | 5 | 85 | 5 |
| 43 | 3 | I-2 | 50 | 5 | 90 | 5 |
| 44 | 4 | I-3 | 50 | 5 | 75 | 5 |
| 45 | 5 | I-5 | 55 | 5 | 75 | 5 |
| 46 | 6 | I-6 | 55 | 5 | 75 | 5 |
| 47 | 7 | I-11 | 50 | 5 | 70 | 5 |
| 48 | 8 | I-16 | 65 | 5 | 80 | 5 |
| 49 | 9 | I-21 | 50 | 5 | 100 | 4 |
| 50 | 10 | I-22 | 70 | 5 | 80 | 5 |
| 51 | 11 | I-25 | 50 | 5 | 115 | 4 |
| 52 | 12 | I-26 | 65 | 5 | 85 | 5 |
| 53 | 13 | I-29 | 55 | 5 | 75 | 5 |
| 54 | 14 | I-36 | 70 | 5 | 105 | 4 |
| 55 | 15 | I-43 | 50 | 5 | 70 | 5 |

TABLE 5-2

| Example No. | Photo-conductor No. | Triamine compound No. | Initial Light potential (-V) | Initial Image quality | After printing 100,000 sheets Light potential (-V) | After printing 100,000 sheets Image quality |
|---|---|---|---|---|---|---|
| 56 | 16 | II-3 | 50 | 5 | 70 | 5 |
| 57 | 17 | II-1 | 60 | 5 | 90 | 5 |
| 58 | 18 | II-2 | 50 | 5 | 65 | 5 |
| 59 | 19 | II-4 | 45 | 5 | 70 | 5 |
| 60 | 20 | II-5 | 50 | 5 | 75 | 5 |
| 61 | 21 | II-11 | 60 | 5 | 75 | 5 |
| 62 | 22 | II-14 | 60 | 5 | 85 | 5 |
| 63 | 23 | II-16 | 75 | 5 | 85 | 5 |
| 64 | 24 | II-18 | 50 | 5 | 100 | 4 |
| 65 | 25 | II-21 | 70 | 5 | 95 | 5 |
| 66 | 26 | II-23 | 50 | 5 | 105 | 5 |
| 67 | 27 | II-27 | 65 | 5 | 90 | 5 |
| 68 | 28 | II-29 | 55 | 5 | 110 | 4 |
| 69 | 29 | II-31 | 70 | 5 | 85 | 5 |
| 70 | 30 | II-41 | 50 | 5 | 90 | 5 |

TABLE 5-3

| Example No. | Photo-conductor No. | Tetramine compound No. | Initial Light potential (-V) | Initial Image quality | After printing 100,000 sheets Light potential (-V) | After printing 100,000 sheets Image quality |
|---|---|---|---|---|---|---|
| 71 | 31 | III-2 | 55 | 5 | 75 | 5 |
| 72 | 32 | III-10 | 50 | 5 | 60 | 5 |
| 73 | 33 | III-23 | 60 | 5 | 65 | 5 |

Example 74

Electrophotographic Photoconductor 34

Electrophotographic Photoconductor 34 was prepared in the same manner as Example 41 except that the charge transport layer coating solution in Example 41 was changed to that having the following composition.

(Charge Transport Layer Coating Solution)

| | |
|---|---|
| Polycarbonate resin (Z POLYCA, manufactured by Teijin Chemicals Ltd.): | 10 parts |
| Diamine compound of Exemplary Compound No. I-4: | 1 part |
| Charge transport material of Structural Formula (47): | 9 parts |
| Tetrahydrofuran: | 100 parts |

Structural Formula (47)

Example 75

Electrophotographic Photoconductor 35

Electrophotographic Photoconductor 35 was prepared in the same manner as Example 74 except that a diamine compound of Exemplary Compound No. in Table 6-1 was used instead of the diamine compound of Exemplary Compound No. I-4 in Example 74, and it was evaluated similarly to Example 41. Results are shown similarly in Table 6-1.

Example 76

Electrophotographic Photoconductor 36

Electrophotographic Photoconductor 36 was prepared in the same manner as Example 74 except that a diamine compound of Exemplary Compound No. in Table 6-1 was used instead of the diamine compound of Exemplary Compound No. I-4 in Example 74, and it was evaluated similarly to Example 41. Results are shown similarly in Table 6-1.

Example 77

Electrophotographic Photoconductor 37

Electrophotographic Photoconductor 37 was prepared in the same manner as Example 74 except that a diamine compound of Exemplary Compound No. in Table 6-1 was used instead of the diamine compound of Exemplary Compound No. I-4 in Example 74, and it was evaluated similarly to Example 41. Results are shown similarly in Table 6-1.

Example 78

Electrophotographic Photoconductor 38

Electrophotographic Photoconductor 38 was prepared in the same manner as Example 74 except that a diamine compound of Exemplary Compound No. in Table 6-1 was used instead of the diamine compound of Exemplary Compound No. I-4 in Example 74, and it was evaluated similarly to Example 41. Results are shown similarly in Table 6-1.

Example 79

Electrophotographic Photoconductor 39

Electrophotographic Photoconductor 39 was prepared in the same manner as Example 74 except that a diamine compound of Exemplary Compound No. in Table 6-1 was used instead of the diamine compound of Exemplary Compound No. I-4 in Example 74, and it was evaluated similarly to Example 41. Results are shown similarly in Table 6-1.

Example 80

Electrophotographic Photoconductor 40

Electrophotographic Photoconductor 40 was prepared in the same manner as Example 74 except that a diamine compound of Exemplary Compound No. in Table 6-1 was used instead of the diamine compound of Exemplary Compound No. I-4 in Example 74, and it was evaluated similarly to Example 41. Results are shown similarly in Table 6-1.

Example 81

Electrophotographic Photoconductor 41

Electrophotographic Photoconductor 41 was prepared in the same manner as Example 74 except that a diamine compound of Exemplary Compound No. in Table 6-1 was used instead of the diamine compound of Exemplary Compound No. I-4 in Example 74, and it was evaluated similarly to Example 41. Results are shown similarly in Table 6-1.

Example 82

Electrophotographic Photoconductor 42

Electrophotographic Photoconductor 42 was prepared in the same manner as Example 74 except that a diamine compound of Exemplary Compound No. in Table 6-1 was used instead of the diamine compound of Exemplary Compound No. I-4 in Example 74, and it was evaluated similarly to Example 41. Results are shown similarly in Table 6-1.

Example 83

Electrophotographic Photoconductor 43

Electrophotographic Photoconductor 43 was prepared in the same manner as Example 74 except that a diamine compound of Exemplary Compound No. in Table 6-1 was used instead of the diamine compound of Exemplary Compound No. I-4 in Example 74, and it was evaluated similarly to Example 41. Results are shown similarly in Table 6-1.

Example 84

Electrophotographic Photoconductor 44

Electrophotographic Photoconductor 44 was prepared in the same manner as Example 74 except that a diamine compound of Exemplary Compound No. in Table 6-1 was used instead of the diamine compound of Exemplary Compound No. I-4 in Example 74, and it was evaluated similarly to Example 41. Results are shown similarly in Table 6-1.

Example 85

Electrophotographic Photoconductor 45

Electrophotographic Photoconductor 45 was prepared in the same manner as Example 74 except that a diamine compound of Exemplary Compound No. in Table 6-1 was used instead of the diamine compound of Exemplary Compound No. I-4 in Example 74, and it was evaluated similarly to Example 41. Results are shown similarly in Table 6-1.

Example 86

Electrophotographic Photoconductor 46

Electrophotographic Photoconductor 46 was prepared in the same manner as Example 74 except that a diamine compound of Exemplary Compound No. in Table 6-1 was used instead of the diamine compound of Exemplary Compound No. I-4 in Example 74, and it was evaluated similarly to Example 41. Results are shown similarly in Table 6-1.

Example 87

Electrophotographic Photoconductor 47

Electrophotographic Photoconductor 47 was prepared in the same manner as Example 74 except that a diamine compound of Exemplary Compound No. in Table 6-1 was used instead of the diamine compound of Exemplary Compound No. I-4 in Example 74, and it was evaluated similarly to Example 41. Results are shown similarly in Table 6-1.

Example 88

Electrophotographic Photoconductor 48

Electrophotographic Photoconductor 48 was prepared in the same manner as Example 74 except that a diamine compound of Exemplary Compound No. in Table 6-1 was used instead of the diamine compound of Exemplary Compound No. I-4 in Example 74, and it was evaluated similarly to Example 41. Results are shown similarly in Table 6-1.

Example 89

Electrophotographic Photoconductor 49

Electrophotographic Photoconductor 49 was prepared in the same manner as Example 74 except that a triamine compound of Exemplary Compound No. in Table 6-2 was used instead of the diamine compound of Exemplary Compound No. I-4 in Example 74, and it was evaluated similarly to Example 41. Results are shown similarly in Table 6-2.

Example 90

Electrophotographic Photoconductor 50

Electrophotographic Photoconductor 50 was prepared in the same manner as Example 74 except that a triamine compound of Exemplary Compound No. in Table 6-2 was used instead of the diamine compound of Exemplary Compound No. I-4 in Example 74, and it was evaluated similarly to Example 41. Results are shown similarly in Table 6-2.

Example 91

Electrophotographic Photoconductor 51

Electrophotographic Photoconductor 51 was prepared in the same manner as Example 74 except that a triamine compound of Exemplary Compound No. in Table 6-2 was used instead of the diamine compound of Exemplary Compound No. I-4 in Example 74, and it was evaluated similarly to Example 41. Results are shown similarly in Table 6-2.

Example 92

Electrophotographic Photoconductor 52

Electrophotographic Photoconductor 52 was prepared in the same manner as Example 74 except that a triamine compound of Exemplary Compound No. in Table 6-2 was used instead of the diamine compound of Exemplary Compound No. I-4 in Example 74, and it was evaluated similarly to Example 41. Results are shown similarly in Table 6-2.

Example 93

Electrophotographic Photoconductor 53

Electrophotographic Photoconductor 53 was prepared in the same manner as Example 74 except that a triamine compound of Exemplary Compound No. in Table 6-2 was used instead of the diamine compound of Exemplary Compound No. I-4 in Example 74, and it was evaluated similarly to Example 41. Results are shown similarly in Table 6-2.

Example 94

Electrophotographic Photoconductor 54

Electrophotographic Photoconductor 54 was prepared in the same manner as Example 74 except that a triamine compound of Exemplary Compound No. in Table 6-2 was used instead of the diamine compound of Exemplary Compound No. I-4 in Example 74, and it was evaluated similarly to Example 41. Results are shown similarly in Table 6-2.

Example 95

Electrophotographic Photoconductor 55

Electrophotographic Photoconductor 55 was prepared in the same manner as Example 74 except that a triamine compound of Exemplary Compound No. in Table 6-2 was used instead of the diamine compound of Exemplary Compound No. I-4 in Example 74, and it was evaluated similarly to Example 41. Results are shown similarly in Table 6-2.

Example 96

Electrophotographic Photoconductor 56

Electrophotographic Photoconductor 56 was prepared in the same manner as Example 74 except that a triamine compound of Exemplary Compound No. in Table 6-2 was used instead of the diamine compound of Exemplary Compound No. I-4 in Example 74, and it was evaluated similarly to Example 41. Results are shown similarly in Table 6-2.

Example 97

Electrophotographic Photoconductor 57

Electrophotographic Photoconductor 57 was prepared in the same manner as Example 74 except that a triamine compound of Exemplary Compound No. in Table 6-2 was used instead of the diamine compound of Exemplary Compound No. I-4 in Example 74, and it was evaluated similarly to Example 41. Results are shown similarly in Table 6-2.

Example 98

Electrophotographic Photoconductor 58

Electrophotographic Photoconductor 58 was prepared in the same manner as Example 74 except that a triamine compound of Exemplary Compound No. in Table 6-2 was used instead of the diamine compound of Exemplary Compound No. I-4 in Example 74, and it was evaluated similarly to Example 41. Results are shown similarly in Table 6-2.

Example 99

Electrophotographic Photoconductor 59

Electrophotographic Photoconductor 59 was prepared in the same manner as Example 74 except that a triamine compound of Exemplary Compound No. in Table 6-2 was used instead of the diamine compound of Exemplary Compound No. I-4 in Example 74, and it was evaluated similarly to Example 41. Results are shown similarly in Table 6-2.

Example 100

Electrophotographic Photoconductor 60

Electrophotographic Photoconductor 60 was prepared in the same manner as Example 74 except that a triamine compound of Exemplary Compound No. in Table 6-2 was used instead of the diamine compound of Exemplary Compound No. I-4 in Example 74, and it was evaluated similarly to Example 41. Results are shown similarly in Table 6-2.

Example 101

Electrophotographic Photoconductor 61

Electrophotographic Photoconductor 61 was prepared in the same manner as Example 74 except that a triamine compound of Exemplary Compound No. in Table 6-2 was used instead of the diamine compound of Exemplary Compound No. I-4 in Example 74, and it was evaluated similarly to Example 41. Results are shown similarly in Table 6-2.

Example 102

Electrophotographic Photoconductor 62

Electrophotographic Photoconductor 62 was prepared in the same manner as Example 74 except that a triamine compound of Exemplary Compound No. in Table 6-2 was used instead of the diamine compound of Exemplary Compound No. I-4 in Example 74, and it was evaluated similarly to Example 41. Results are shown similarly in Table 6-2.

Example 103

Electrophotographic Photoconductor 63

Electrophotographic Photoconductor 63 was prepared in the same manner as Example 74 except that a triamine compound of Exemplary Compound No. in Table 6-2 was used instead of the diamine compound of Exemplary Compound No. I-4 in Example 74, and it was evaluated similarly to Example 41. Results are shown similarly in Table 6-2.

Example 104

Electrophotographic Photoconductor 64

Electrophotographic Photoconductor 64 was prepared in the same manner as Example 74 except that a tetramine compound of Exemplary Compound No. in Table 6-3 was used instead of the diamine compound of Exemplary Compound No. I-4 in Example 74, and it was evaluated similarly to Example 41. Results are shown similarly in Table 6-3.

Example 105

Electrophotographic Photoconductor 65

Electrophotographic Photoconductor 65 was prepared in the same manner as Example 74 except that a tetramine compound of Exemplary Compound No. in Table 6-3 was used instead of the diamine compound of Exemplary Compound No. I-4 in Example 74, and it was evaluated similarly to Example 41. Results are shown similarly in Table 6-3.

Example 106

Electrophotographic Photoconductor 66

Electrophotographic Photoconductor 66 was prepared in the same manner as Example 74 except that a tetramine compound of Exemplary Compound No. in Table 6-3 was used instead of the diamine compound of Exemplary Compound No. I-4 in Example 74, and it was evaluated similarly to Example 41. Results are shown similarly in Table 6-3.

TABLE 6-1

| | | | Initial | | After printing 100,000 sheets | |
|---|---|---|---|---|---|---|
| Example No. | Photo-conductor No. | Diamine compound No. | Light potential (-V) | Image quality | Light potential (-V) | Image quality |
| 74 | 34 | I-4 | 45 | 5 | 55 | 5 |
| 75 | 35 | I-1 | 50 | 5 | 60 | 5 |
| 76 | 36 | I-2 | 45 | 5 | 55 | 5 |
| 77 | 37 | I-3 | 45 | 5 | 50 | 5 |
| 78 | 38 | I-5 | 50 | 5 | 60 | 5 |
| 79 | 39 | I-6 | 50 | 5 | 60 | 5 |
| 80 | 40 | I-11 | 50 | 5 | 55 | 5 |
| 81 | 41 | I-16 | 50 | 5 | 60 | 5 |
| 82 | 42 | I-21 | 50 | 5 | 60 | 5 |
| 83 | 43 | I-22 | 55 | 5 | 65 | 5 |
| 84 | 44 | I-25 | 50 | 5 | 60 | 5 |
| 85 | 45 | I-26 | 60 | 5 | 65 | 5 |
| 86 | 46 | I-29 | 50 | 5 | 60 | 5 |
| 87 | 47 | I-36 | 55 | 5 | 65 | 5 |
| 88 | 48 | I-43 | 50 | 5 | 65 | 5 |

TABLE 6-2

| | | | Initial | | After printing 100,000 sheets | |
|---|---|---|---|---|---|---|
| Example No. | Photo-conductor No. | Triamine compound No. | Light potential (-V) | Image quality | Light potential (-V) | Image quality |
| 89 | 49 | II-3 | 45 | 5 | 60 | 5 |
| 90 | 50 | II-1 | 50 | 5 | 65 | 5 |
| 91 | 51 | II-2 | 55 | 5 | 55 | 5 |
| 92 | 52 | II-4 | 45 | 5 | 60 | 5 |
| 93 | 53 | II-5 | 55 | 5 | 60 | 5 |
| 94 | 54 | II-11 | 50 | 5 | 65 | 5 |
| 95 | 55 | II-14 | 55 | 5 | 65 | 5 |
| 96 | 56 | II-16 | 50 | 5 | 60 | 5 |
| 97 | 57 | II-18 | 50 | 5 | 65 | 5 |
| 98 | 58 | II-21 | 55 | 5 | 70 | 5 |
| 99 | 59 | II-23 | 50 | 5 | 60 | 5 |
| 100 | 60 | II-27 | 65 | 5 | 70 | 5 |
| 101 | 61 | II-29 | 50 | 5 | 55 | 5 |
| 102 | 62 | II-31 | 55 | 5 | 65 | 5 |
| 103 | 63 | II-41 | 55 | 5 | 70 | 5 |

TABLE 6-3

| | | | Initial | | After printing 100,000 sheets | |
|---|---|---|---|---|---|---|
| Example No. | Photo-conductor No. | Tetramine compound No. | Light potential (-V) | Image quality | Light potential (-V) | Image quality |
| 103 | 64 | III-2 | 50 | 5 | 65 | 5 |
| 104 | 65 | III-10 | 50 | 5 | 55 | 5 |
| 105 | 66 | III-23 | 55 | 5 | 60 | 5 |

Example 107

Electrophotographic Photoconductor 67

Electrophotographic Photoconductor 67 was prepared in the same manner as Example 74 except that a diamine compound of Exemplary Compound No. in Table 7-1 was used instead of the diamine compound of Exemplary Compound No. I-4 in Example 74 and that the amounts of the included diamine compound and the charge transport material were changed to those described below, and it was evaluated similarly to Example 41. Results are shown similarly in Table 7-1.

| Diamine compound: | 1 part |
|---|---|
| Charge transport material: | 7 parts |

Example 108

Electrophotographic Photoconductor 68

Electrophotographic Photoconductor 68 was prepared in the same manner as Example 74 except that a diamine compound of Exemplary Compound No. in Table 7-1 was used instead of the diamine compound of Exemplary Compound No. I-4 in Example 74 and that the amounts of the included diamine compound and the charge transport material were changed to those described below, and it was evaluated similarly to Example 41. Results are shown similarly in Table 7-1.

| Diamine compound: | 1 part |
|---|---|
| Charge transport material: | 7 parts |

Example 109

Electrophotographic Photoconductor 69

Electrophotographic Photoconductor 69 was prepared in the same manner as Example 74 except that a diamine compound of Exemplary Compound No. in Table 7-1 was used instead of the diamine compound of Exemplary Compound No. I-4 in Example 74 and that the amounts of the included diamine compound and the charge transport material were changed to those described below, and it was evaluated similarly to Example 41. Results are shown similarly in Table 7-1.

| Diamine compound: | 1 part |
|---|---|
| Charge transport material: | 7 parts |

Example 110

Electrophotographic Photoconductor 70

Electrophotographic Photoconductor 70 was prepared in the same manner as Example 74 except that a diamine compound of Exemplary Compound No. in Table 7-1 was used instead of the diamine compound of Exemplary Compound No. I-4 in Example 74 and that the amounts of the included diamine compound and the charge transport material were changed to those described below, and it was evaluated similarly to Example 41. Results are shown similarly in Table 7-1.

| Diamine compound: | 1 part |
|---|---|
| Charge transport material: | 7 parts |

Example 111

Electrophotographic Photoconductor 71

Electrophotographic Photoconductor 71 was prepared in the same manner as Example 107 except that a triamine compound of Exemplary Compound No. in Table 7-2 was used instead of the diamine compound of Exemplary Compound No. I-5 in Example 107, and it was evaluated similarly to Example 41. Results are shown similarly in Table 7-2.

Example 112

Electrophotographic Photoconductor 72

Electrophotographic Photoconductor 72 was prepared in the same manner as Example 107 except that a triamine compound of Exemplary Compound No. in Table 7-2 was used instead of the diamine compound of Exemplary Compound No. I-5 in Example 107, and it was evaluated similarly to Example 41. Results are shown similarly in Table 7-2.

Example 113

Electrophotographic Photoconductor 73

Electrophotographic Photoconductor 73 was prepared in the same manner as Example 107 except that a triamine compound of Exemplary Compound No. in Table 7-2 was used instead of the diamine compound of Exemplary Compound No. I-5 in Example 107, and it was evaluated similarly to Example 41. Results are shown similarly in Table 7-2.

Example 114

Electrophotographic Photoconductor 74

Electrophotographic Photoconductor 74 was prepared in the same manner as Example 107 except that a triamine compound of Exemplary Compound No. in Table 7-2 was used instead of the diamine compound of Exemplary Compound No. I-5 in Example 107, and it was evaluated similarly to Example 41. Results are shown similarly in Table 7-2.

Example 115

Electrophotographic Photoconductor 75

Electrophotographic Photoconductor 75 was prepared in the same manner as Example 107 except that a tetramine compound of Exemplary Compound No. in Table 7-3 was used instead of the diamine compound of Exemplary Compound No. I-5 in Example 107, and it was evaluated similarly to Example 41. Results are shown similarly in Table 7-3.

Example 116

Electrophotographic Photoconductor 76

Electrophotographic Photoconductor 76 was prepared in the same manner as Example 107 except that a tetramine compound of Exemplary Compound No. in Table 7-3 was used instead of the diamine compound of Exemplary Compound No. I-5 in Example 107, and it was evaluated similarly to Example 41. Results are shown similarly in Table 7-3.

Example 117

Electrophotographic Photoconductor 77

Electrophotographic Photoconductor 77 was prepared in the same manner as Example 107 except that a tetramine compound of Exemplary Compound No. in Table 7-3 was used instead of the diamine compound of Exemplary Compound No. I-5 in Example 107, and it was evaluated similarly to Example 41. Results are shown similarly in Table 7-3.

TABLE 7-1

| Example No. | Photo-conductor No. | Diamine compound No. | Initial Light potential (-V) | Initial Image quality | After printing 100,000 sheets Light potential (-V) | After printing 100,000 sheets Image quality |
|---|---|---|---|---|---|---|
| 107 | 67 | I-5 | 50 | 5 | 55 | 5 |
| 108 | 68 | I-16 | 50 | 5 | 55 | 5 |
| 109 | 69 | I-23 | 55 | 5 | 65 | 5 |
| 110 | 70 | I-39 | 55 | 5 | 65 | 5 |

TABLE 7-2

| Example No. | Photo-conductor No. | Triamine compound No. | Initial Light potential (-V) | Initial Image quality | After printing 100,000 sheets Light potential (-V) | After printing 100,000 sheets Image quality |
|---|---|---|---|---|---|---|
| 111 | 71 | II-3 | 45 | 5 | 50 | 5 |
| 112 | 72 | II-16 | 50 | 5 | 50 | 5 |
| 113 | 73 | II-22 | 55 | 5 | 60 | 5 |
| 114 | 74 | II-37 | 55 | 5 | 70 | 5 |

TABLE 7-3

| Example No. | Photo-conductor No. | Tetramine compound No. | Initial Light potential (-V) | Initial Image quality | After printing 100,000 sheets Light potential (-V) | After printing 100,000 sheets Image quality |
|---|---|---|---|---|---|---|
| 115 | 75 | III-2 | 55 | 5 | 75 | 5 |
| 116 | 76 | III-10 | 50 | 5 | 65 | 5 |
| 117 | 77 | III-23 | 55 | 5 | 70 | 5 |

Example 118

Electrophotographic Photoconductor 78

Electrophotographic Photoconductor 78 was prepared in the same manner as Example 74 except that a diamine compound of Exemplary Compound No. in Table 8-1 was used instead of the diamine compound of Exemplary Compound No. I-4 in Example 74 and that the amounts of the included diamine compound and the charge transport material were changed to those described below, and it was evaluated similarly to Example 41. Results are shown similarly in Table 8-1.

| Diamine compound: | 5 parts |
|---|---|
| Charge transport material: | 5 parts |

Example 119

Electrophotographic Photoconductor 79

Electrophotographic Photoconductor 79 was prepared in the same manner as Example 74 except that a diamine compound of Exemplary Compound No. in Table 8-1 was used instead of the diamine compound of Exemplary Compound No. I-4 in Example 74 and that the amounts of the included diamine compound and the charge transport material were changed to those described below, and it was evaluated similarly to Example 41. Results are shown similarly in Table 8-1.

| | |
|---|---|
| Diamine compound: | 5 parts |
| Charge transport material: | 5 parts |

Example 120

Electrophotographic Photoconductor 80

Electrophotographic Photoconductor 80 was prepared in the same manner as Example 74 except that a diamine compound of Exemplary Compound No. in Table 8-1 was used instead of the diamine compound of Exemplary Compound No. I-4 in Example 74 and that the amounts of the included diamine compound and the charge transport material were changed to those described below, and it was evaluated similarly to Example 41. Results are shown similarly in Table 8-1.

| | |
|---|---|
| Diamine compound: | 5 parts |
| Charge transport material: | 5 parts |

Example 121

Electrophotographic Photoconductor 81

Electrophotographic Photoconductor 81 was prepared in the same manner as Example 74 except that a diamine compound of Exemplary Compound No. in Table 8-1 was used instead of the diamine compound of Exemplary Compound No. I-4 in Example 74 and that the amounts of the included diamine compound and the charge transport material were changed to those described below, and it was evaluated similarly to Example 41. Results are shown similarly in Table 8-1.

| | |
|---|---|
| Diamine compound: | 5 parts |
| Charge transport material: | 5 parts |

Example 122

Electrophotographic Photoconductor 82

Electrophotographic Photoconductor 82 was prepared in the same manner as Example 118 except that a triamine compound of Exemplary Compound No. in Table 8-2 was used instead of the diamine compound of Exemplary Compound No. I-5 in Example 118, and it was evaluated similarly to Example 41. Results are shown similarly in Table 8-2.

Example 123

Electrophotographic Photoconductor 83

Electrophotographic Photoconductor 83 was prepared in the same manner as Example 118 except that a triamine compound of Exemplary Compound No. in Table 8-2 was used instead of the diamine compound of Exemplary Compound No. I-5 in Example 118, and it was evaluated similarly to Example 41. Results are shown similarly in Table 8-2.

Example 124

Electrophotographic Photoconductor 84

Electrophotographic Photoconductor 84 was prepared in the same manner as Example 118 except that a triamine compound of Exemplary Compound No. in Table 8-2 was used instead of the diamine compound of Exemplary Compound No. I-5 in Example 118, and it was evaluated similarly to Example 41. Results are shown similarly in Table 8-2.

Example 125

Electrophotographic Photoconductor 85

Electrophotographic Photoconductor 85 was prepared in the same manner as Example 118 except that a triamine compound of Exemplary Compound No. in Table 8-2 was used instead of the diamine compound of Exemplary Compound No. I-5 in Example 118, and it was evaluated similarly to Example 41. Results are shown similarly in Table 8-2.

Example 126

Electrophotographic Photoconductor 86

Electrophotographic Photoconductor 86 was prepared in the same manner as Example 118 except that a tetramine compound of Exemplary Compound No. in Table 8-3 was used instead of the diamine compound of Exemplary Compound No. I-5 in Example 118, and it was evaluated similarly to Example 41. Results are shown similarly in Table 8-3.

Example 127

Electrophotographic Photoconductor 87

Electrophotographic Photoconductor 87 was prepared in the same manner as Example 118 except that a tetramine compound of Exemplary Compound No. in Table 8-3 was used instead of the diamine compound of Exemplary Compound No. I-5 in Example 118, and it was evaluated similarly to Example 41. Results are shown similarly in Table 8-3.

Example 128

Electrophotographic Photoconductor 88

Electrophotographic Photoconductor 88 was prepared in the same manner as Example 118 except that a tetramine compound of Exemplary Compound No. in Table 8-3 was used instead of the diamine compound of Exemplary Compound No. I-5 in Example 118, and it was evaluated similarly to to Example 41. Results are shown similarly in Table 8-3.

TABLE 8-1

| | | | Initial | | After printing 100,000 sheets | |
|---|---|---|---|---|---|---|
| Example No. | Photo-conductor No. | Diamine compound No. | Light potential (-V) | Image quality | Light potential (-V) | Image quality |
| 118 | 78 | I-5 | 50 | 5 | 55 | 5 |
| 119 | 79 | I-16 | 50 | 5 | 60 | 5 |

TABLE 8-1-continued

| | | | Initial | | After printing 100,000 sheets | |
|---|---|---|---|---|---|---|
| Example No. | Photo-conductor No. | Diamine compound No. | Light potential (-V) | Image quality | Light potential (-V) | Image quality |
| 120 | 80 | I-23 | 60 | 5 | 70 | 5 |
| 121 | 81 | I-39 | 70 | 5 | 85 | 5 |

TABLE 8-2

| | | | Initial | | After printing 100,000 sheets | |
|---|---|---|---|---|---|---|
| Example No. | Photo-conductor No. | Triamine compound No. | Light potential (-V) | Image quality | Light potential (-V) | Image quality |
| 122 | 82 | II-3 | 50 | 5 | 55 | 5 |
| 123 | 83 | II-16 | 55 | 5 | 60 | 5 |
| 124 | 84 | II-22 | 60 | 5 | 85 | 5 |
| 125 | 85 | II-37 | 70 | 5 | 70 | 5 |

TABLE 8-3

| | | | Initial | | After printing 100,000 sheets | |
|---|---|---|---|---|---|---|
| Example No. | Photo-conductor No. | Tetramine compound No. | Light potential (-V) | Image quality | Light potential (-V) | Image quality |
| 126 | 86 | III-3 | 60 | 5 | 75 | 5 |
| 127 | 87 | III-10 | 55 | 5 | 75 | 5 |
| 128 | 88 | III-23 | 55 | 5 | 80 | 5 |

Example 129

Electrophotographic Photoconductor 89

Electrophotographic Photoconductor 89 was prepared in the same manner as Example 74 except that a diamine compound of Exemplary Compound No. in Table 9-1 was used instead of the diamine compound of Exemplary Compound No. I-4 in Example 74 and that a charge transport material of Structural Formula (48) was used instead of the charge transport material of Structural Formula (47), and it was evaluated similarly to Example 41. Results are shown similarly in Table 9-1.

Structural Formula (48)

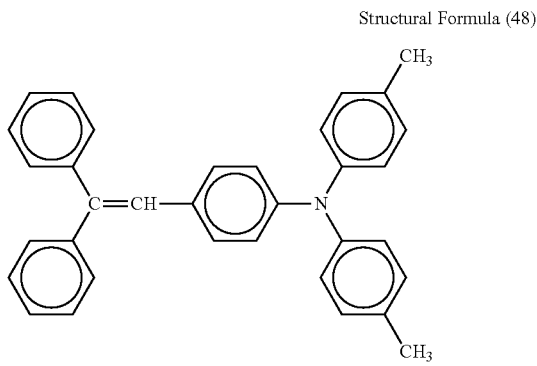

Example 130

Electrophotographic Photoconductor 90

Electrophotographic Photoconductor 90 was prepared in the same manner as Example 74 except that a diamine compound of Exemplary Compound No. in Table 9-1 was used instead of the diamine compound of Exemplary Compound No. I-4 in Example 74 and that a charge transport material of Structural Formula (48) was used instead of the charge transport material of Structural Formula (47), and it was evaluated similarly to Example 41. Results are shown similarly in Table 9-1.

Example 131

Electrophotographic Photoconductor 911

Electrophotographic Photoconductor 91 was prepared in the same manner as Example 74 except that a diamine compound of Exemplary Compound No. in Table 9-1 was used instead of the diamine compound of Exemplary Compound No. I-4 in Example 74 and that a charge transport material of Structural Formula (48) was used instead of the charge transport material of Structural Formula (47), and it was evaluated similarly to Example 41. Results are shown similarly in Table 9-1.

Example 132

Electrophotographic Photoconductor 92

Electrophotographic Photoconductor 92 was prepared in the same manner as Example 74 except that a diamine compound of Exemplary Compound No. in Table 9-1 was used instead of the diamine compound of Exemplary Compound No. I-4 in Example 74 and that a charge transport material of Structural Formula (48) was used instead of the charge transport material of Structural Formula (47), and it was evaluated similarly to Example 41. Results are shown similarly in Table 9-1.

Example 133

Electrophotographic Photoconductor 93

Electrophotographic Photoconductor 93 was prepared in the same manner as Example 129 except that a triamine compound of Exemplary Compound No. in Table 9-2 was used instead of the diamine compound of Exemplary Compound No. I-5 in Example 129, and it was evaluated similarly to Example 41. Results are shown similarly in Table 9-2.

Example 134

Electrophotographic Photoconductor 94

Electrophotographic Photoconductor 94 was prepared in the same manner as Example 129 except that a triamine compound of Exemplary Compound No. in Table 9-2 was used instead of the diamine compound of Exemplary Compound No. I-5 in Example 129, and it was evaluated similarly to Example 41. Results are shown similarly in Table 9-2.

Example 135

Electrophotographic Photoconductor 95

Electrophotographic Photoconductor 95 was prepared in the same manner as Example 129 except that a triamine compound of Exemplary Compound No. in Table 9-2 was used instead of the diamine compound of Exemplary Compound No. I-5 in Example 129, and it was evaluated similarly to Example 41. Results are shown similarly in Table 9-2.

Example 136

Electrophotographic Photoconductor 96

Electrophotographic Photoconductor 96 was prepared in the same manner as Example 129 except that a triamine compound of Exemplary Compound No. in Table 9-2 was used instead of the diamine compound of Exemplary Compound No. I-5 in Example 129, and it was evaluated similarly to Example 41. Results are shown similarly in Table 9-2.

Example 137

Electrophotographic Photoconductor 97

Electrophotographic Photoconductor 97 was prepared in the same manner as Example 129 except that a tetramine compound of Exemplary Compound No. in Table 9-3 was used instead of the diamine compound of Exemplary Compound No. I-5 in Example 129, and it was evaluated similarly to Example 41. Results are shown similarly in Table 9-3.

Example 138

Electrophotographic Photoconductor 98

Electrophotographic Photoconductor 98 was prepared in the same manner as Example 129 except that a tetramine compound of Exemplary Compound No. in Table 9-3 was used instead of the diamine compound of Exemplary Compound No. I-5 in Example 129, and it was evaluated similarly to Example 41. Results are shown similarly in Table 9-3.

Example 139

Electrophotographic Photoconductor 99

Electrophotographic Photoconductor 99 was prepared in the same manner as Example 129 except that a tetramine compound of Exemplary Compound No. in Table 9-3 was used instead of the diamine compound of Exemplary Compound No. I-5 in Example 129, and it was evaluated similarly to Example 41. Results are shown similarly in Table 9-3.

TABLE 9-1

| | | | Initial | | After printing 100,000 sheets | |
| --- | --- | --- | --- | --- | --- | --- |
| Example No. | Photo-conductor No. | Diamine compound No. | Light potential (-V) | Image quality | Light potential (-V) | Image quality |
| 129 | 89 | I-5 | 50 | 5 | 60 | 5 |
| 130 | 90 | I-16 | 55 | 5 | 65 | 5 |
| 131 | 91 | I-23 | 55 | 5 | 65 | 5 |
| 132 | 92 | I-39 | 60 | 5 | 80 | 5 |

TABLE 9-2

| | | | Initial | | After printing 100,000 sheets | |
| --- | --- | --- | --- | --- | --- | --- |
| Example No. | Photo-conductor No. | Triamine compound No. | Light potential (-V) | Image quality | Light potential (-V) | Image quality |
| 133 | 93 | II-6 | 50 | 5 | 55 | 5 |
| 134 | 94 | II-17 | 50 | 5 | 55 | 5 |
| 135 | 95 | II-26 | 55 | 5 | 75 | 5 |
| 136 | 96 | II-39 | 60 | 5 | 65 | 5 |

TABLE 9-3

| | | | Initial | | After printing 100,000 sheets | |
| --- | --- | --- | --- | --- | --- | --- |
| Example No. | Photo-conductor No. | Tetramine compound No. | Light potential (-V) | Image quality | Light potential (-V) | Image quality |
| 137 | 97 | III-2 | 55 | 5 | 70 | 5 |
| 138 | 98 | III-10 | 50 | 5 | 70 | 5 |
| 139 | 99 | III-23 | 55 | 5 | 75 | 5 |

Example 140

Electrophotographic Photoconductor 100

Electrophotographic Photoconductor 100 was prepared in the same manner as Example 74 except that a diamine compound of Exemplary Compound No. in Table 10-1 was used instead of the diamine compound of Exemplary Compound No. I-4 in Example 74 and that a charge transport material of Structural Formula (49) was used instead of the charge transport material of Structural Formula (47), and it was evaluated similarly to Example 41. Results are shown similarly in Table 10-1.

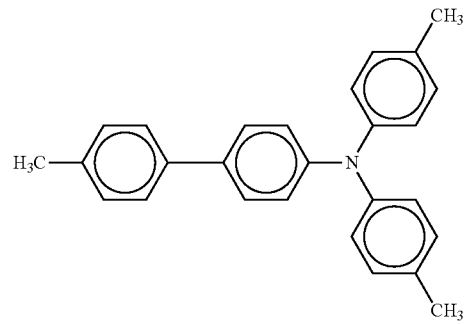

Structural Formula (49)

Example 141

Electrophotographic Photoconductor 101

Electrophotographic Photoconductor 101 was prepared in the same manner as Example 74 except that a diamine compound of Exemplary Compound No. in Table 10-1 was used instead of the diamine compound of Exemplary Compound No. I-4 in Example 74 and that a charge transport material of Structural Formula (49) was used instead of the charge transport material of Structural Formula (47), and it was evaluated similarly to Example 41. Results are shown similarly in Table 10-1.

Example 142

Electrophotographic Photoconductor 102

Electrophotographic Photoconductor 102 was prepared in the same manner as Example 74 except that a diamine compound of Exemplary Compound No. in Table 10-1 was used instead of the diamine compound of Exemplary Compound No. I-4 in Example 74 and that a charge transport material of Structural Formula (49) was used instead of the charge transport material of Structural Formula (47), and it was evaluated similarly to Example 41. Results are shown similarly in Table 10-1.

Example 143

Electrophotographic Photoconductor 103

Electrophotographic Photoconductor 103 was prepared in the same manner as Example 74 except that a diamine compound of Exemplary Compound No. in Table 10-1 was used instead of the diamine compound of Exemplary Compound No. I-4 in Example 74 and that a charge transport material of Structural Formula (49) was used instead of the charge transport material of Structural Formula (47), and it was evaluated similarly to Example 41. Results are shown similarly in Table 10-1.

Example 144

Electrophotographic Photoconductor 104

Electrophotographic Photoconductor 104 was prepared in the same manner as Example 140 except that a triamine compound of Exemplary Compound No. in Table 10-2 was used instead of the diamine compound of Exemplary Compound No. I-5 in Example 140, and it was evaluated similarly to Example 41. Results are shown similarly in Table 10-2.

Example 145

Electrophotographic Photoconductor 105

Electrophotographic Photoconductor 105 was prepared in the same manner as Example 140 except that a triamine compound of Exemplary Compound No. in Table 10-2 was used instead of the diamine compound of Exemplary Compound No. I-5 in Example 140, and it was evaluated similarly to Example 41. Results are shown similarly in Table 10-2.

Example 146

Electrophotographic Photoconductor 106

Electrophotographic Photoconductor 106 was prepared in the same manner as Example 140 except that a triamine compound of Exemplary Compound No. in Table 10-2 was used instead of the diamine compound of Exemplary Compound No. I-5 in Example 140, and it was evaluated similarly to Example 41. Results are shown similarly in Table 10-2.

Example 147

Electrophotographic Photoconductor 107

Electrophotographic Photoconductor 107 was prepared in the same manner as Example 140 except that a triamine compound of Exemplary Compound No. in Table 10-2 was used instead of the diamine compound of Exemplary Compound No. I-5 in Example 140, and it was evaluated similarly to Example 41. Results are shown similarly in Table 10-2.

Example 148

Electrophotographic Photoconductor 108

Electrophotographic Photoconductor 108 was prepared in the same manner as Example 140 except that a tetramine compound of Exemplary Compound No. in Table 10-3 was used instead of the diamine compound of Exemplary Compound No. I-5 in Example 140, and it was evaluated similarly to Example 41. Results are shown similarly in Table 10-3.

Example 149

Electrophotographic Photoconductor 109

Electrophotographic Photoconductor 109 was prepared in the same manner as Example 140 except that a tetramine compound of Exemplary Compound No. in Table 10-3 was used instead of the diamine compound of Exemplary Compound No. I-5 in Example 140, and it was evaluated similarly to Example 41. Results are shown similarly in Table 10-3.

Example 150

Electrophotographic Photoconductor 110

Electrophotographic Photoconductor 110 was prepared in the same manner as Example 140 except that a tetramine compound of Exemplary Compound No. in Table 10-3 was used instead of the diamine compound of Exemplary Compound No. I-5 in Example 140, and it was evaluated similarly to Example 41. Results are shown similarly in Table 10-3.

TABLE 10-1

| Example No. | Photo-conductor No. | Diamine compound No. | Initial Light potential (-V) | Initial Image quality | After printing 100,000 sheets Light potential (-V) | After printing 100,000 sheets Image quality |
|---|---|---|---|---|---|---|
| 140 | 100 | I-5 | 50 | 5 | 65 | 5 |
| 141 | 101 | I-16 | 50 | 5 | 65 | 5 |
| 142 | 102 | I-23 | 60 | 5 | 80 | 5 |
| 143 | 103 | I-39 | 55 | 5 | 85 | 5 |

TABLE 10-2

| Example No. | Photo-conductor No. | Triamine compound No. | Light potential (-V) Initial | Image quality | Light potential (-V) After printing 100,000 sheets | Image quality |
|---|---|---|---|---|---|---|
| 144 | 104 | II-6 | 50 | 5 | 60 | 5 |
| 145 | 105 | II-17 | 55 | 5 | 65 | 5 |
| 146 | 106 | II-26 | 65 | 5 | 75 | 5 |
| 147 | 107 | II-39 | 55 | 5 | 70 | 5 |

TABLE 10-3

| Example No. | Photo-conductor No. | Tetramine compound No. | Light potential (-V) Initial | Image quality | Light potential (-V) After printing 100,000 sheets | Image quality |
|---|---|---|---|---|---|---|
| 148 | 108 | III-2 | 55 | 5 | 70 | 5 |
| 149 | 109 | III-10 | 50 | 5 | 70 | 5 |
| 150 | 110 | III-23 | 55 | 5 | 75 | 5 |

Example 151

Electrophotographic Photoconductor 111

Electrophotographic Photoconductor 111 was prepared in the same manner as Example 74 except that a diamine compound of Exemplary Compound No. in Table 11-1 was used instead of the diamine compound of Exemplary Compound No. I-4 in Example 74 and that a material of Structural Formula (50) was used instead of the charge transport material and the binder resin included in the charge transport layer, and it was evaluated similarly to Example 41. Results are shown similarly in Table 11-1.

Example 152

Electrophotographic Photoconductor 112

Electrophotographic Photoconductor 112 was prepared in the same manner as Example 74 except that a diamine compound of Exemplary Compound No. in Table 11-1 was used instead of the diamine compound of Exemplary Compound No. I-4 in Example 74 and that a material of Structural Formula (50) above was used instead of the charge transport material and the binder resin included in the charge transport layer, and it was evaluated similarly to Example 41. Results are shown similarly in Table 11-1.

Example 153

Electrophotographic Photoconductor 113

Electrophotographic Photoconductor 113 was prepared in the same manner as Example 74 except that a diamine compound of Exemplary Compound No. in Table 11-1 was used instead of the diamine compound of Exemplary Compound No. I-4 in Example 74 and that a material of Structural Formula (50) above was used instead of the charge transport material and the binder resin included in the charge transport layer, and it was evaluated similarly to Example 41. Results are shown similarly in Table 11-1.

Example 154

Electrophotographic Photoconductor 114

Electrophotographic Photoconductor 114 was prepared in the same manner as Example 151 except that a triamine compound of Exemplary Compound No. in Table 11-2 was used instead of the diamine compound of Exemplary Compound No. I-1 in Example 151, and it was evaluated similarly to Example 41. Results are shown similarly in Table 11-2.

| | |
|---|---|
| Charge transport polymer of Structural Formula (50) below: | 19 parts |

Structural Formula (50)

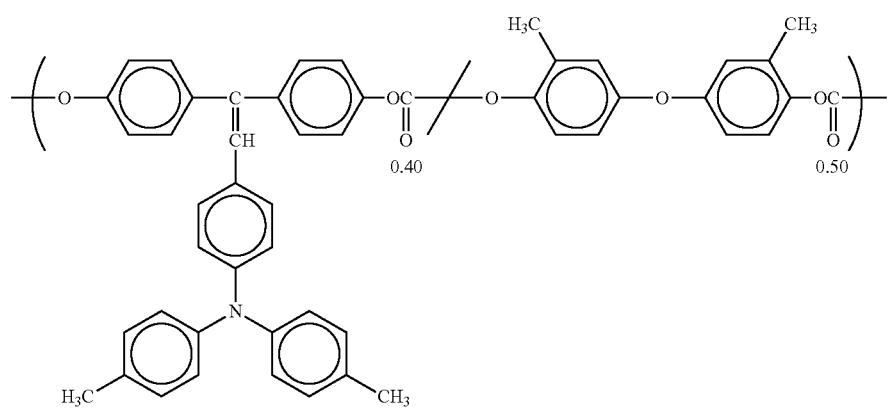

Example 155

Electrophotographic Photoconductor 115

Electrophotographic Photoconductor 115 was prepared in the same manner as Example 151 except that a triamine compound of Exemplary Compound No. in Table 11-2 was used instead of the diamine compound of Exemplary Compound No. I-1 in Example 151, and it was evaluated similarly to Example 41. Results are shown similarly in Table 11-2.

Example 156

Electrophotographic Photoconductor 116

Electrophotographic Photoconductor 116 was prepared in the same manner as Example 151 except that a triamine compound of Exemplary Compound No. in Table 11-2 was used instead of the diamine compound of Exemplary Compound No. I-1 in Example 151, and it was evaluated similarly to Example 41. Results are shown similarly in Table 11-2.

Example 157

Electrophotographic Photoconductor 117

Electrophotographic Photoconductor 117 was prepared in the same manner as Example 151 except that a tetramine compound of Exemplary Compound No. in Table 11-3 was used instead of the diamine compound of Exemplary Compound No. I-1 in Example 151, and it was evaluated similarly to Example 41. Results are shown similarly in Table 11-3.

Example 158

Electrophotographic Photoconductor 118

Electrophotographic Photoconductor 118 was prepared in the same manner as Example 151 except that a tetramine compound of Exemplary Compound No. in Table 11-3 was used instead of the diamine compound of Exemplary Compound No. I-1 in Example 151, and it was evaluated similarly to Example 41. Results are shown similarly in Table 11-3.

Example 159

Electrophotographic Photoconductor 119

Electrophotographic Photoconductor 119 was prepared in the same manner as Example 151 except that a tetramine compound of Exemplary Compound No. in Table 11-3 was used instead of the diamine compound of Exemplary Compound No. I-1 in Example 151, and it was evaluated similarly to Example 41. Results are shown similarly in Table 11-3.

TABLE 11-1

| Example No. | Photo-conductor No. | Diamine compound No. | Initial Light potential (-V) | Initial Image quality | After printing 100,000 sheets Light potential (-V) | After printing 100,000 sheets Image quality |
|---|---|---|---|---|---|---|
| 151 | 111 | I-1 | 50 | 5 | 75 | 5 |
| 152 | 112 | I-5 | 45 | 5 | 70 | 5 |
| 153 | 113 | I-20 | 55 | 5 | 80 | 5 |

TABLE 11-2

| Example No. | Photo-conductor No. | Triamine compound No. | Initial Light potential (-V) | Initial Image quality | After printing 100,000 sheets Light potential (-V) | After printing 100,000 sheets Image quality |
|---|---|---|---|---|---|---|
| 154 | 114 | II-6 | 45 | 5 | 65 | 5 |
| 155 | 115 | II-17 | 50 | 5 | 70 | 5 |
| 156 | 116 | II-26 | 50 | 5 | 60 | 5 |

TABLE 11-3

| Example No. | Photo-conductor No. | Tetramine compound No. | Initial Light potential (-V) | Initial Image quality | After printing 100,000 sheets Light potential (-V) | After printing 100,000 sheets Image quality |
|---|---|---|---|---|---|---|
| 157 | 117 | III-2 | 50 | 5 | 70 | 5 |
| 158 | 118 | III-10 | 55 | 5 | 65 | 5 |
| 159 | 119 | III-23 | 20 | 5 | 80 | 5 |

Example 160

Electrophotographic Photoconductor 120

Electrophotographic Photoconductor 120 was prepared in the same manner as Example 74 except that the diamine compound of Exemplary Compound No. I-4 in Example 74 was changed to a diamine compound of Exemplary Compound No. in Table 12-1 and that the charge transport material and the binder resin included in the charge transport layer were changed to the material of Structural Formula (51) below, and it was evaluated similarly to Example 41. Results are shown similarly in Table 12-1.

Charge transport polymers of Structural Formula (51) below: 19 parts

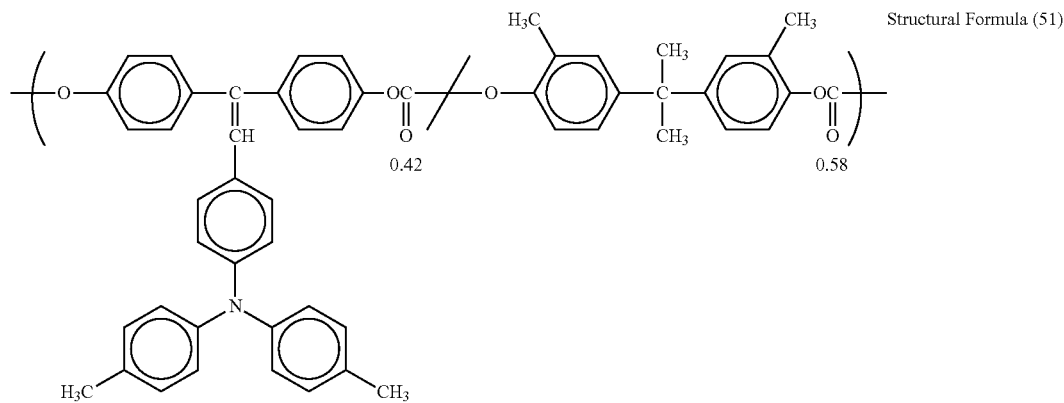

Structural Formula (51)

Example 161

Electrophotographic Photoconductor 121

Electrophotographic Photoconductor 121 was prepared in the same manner as Example 74 except that the diamine compound of Exemplary Compound No. I-4 in Example 74 was changed to a diamine compound of Exemplary Compound No. in Table 12-1 and that the charge transport material and the binder resin included in the charge transport layer was changed to the material of Structural Formula (51) above, and it was evaluated similarly to Example 41. Results are shown similarly in Table 12-1.

Example 162

Electrophotographic Photoconductor 1221

Electrophotographic Photoconductor 122 was prepared in the same manner as Example 160 except that the diamine compound of Exemplary Compound No. I-2 in Example 160 was changed to a triamine compound of Exemplary Compound No. in Table 12-2, and it was evaluated similarly to Example 41. Results are shown similarly in Table 12-2.

Example 163

Electrophotographic Photoconductor 123

Electrophotographic Photoconductor 123 was prepared in the same manner as Example 160 except that a triamine compound of Exemplary Compound No. in Table 12-2 was used instead of the diamine compound of Exemplary Compound No. I-2 in Example 160, and it was evaluated similarly to Example 41. Results are shown similarly in Table 12-2.

Example 164

Electrophotographic Photoconductor 124

Electrophotographic Photoconductor 124 was prepared in the same manner as Example 160 except that a tetramine compound of Exemplary Compound No. in Table 12-3 was used instead of the diamine compound of Exemplary Compound No. I-2 in Example 160, and it was evaluated similarly to Example 41. Results are shown similarly in Table 12-3.

Example 165

Electrophotographic Photoconductor 125

Electrophotographic Photoconductor 125 was prepared in the same manner as Example 160 except that a tetramine compound of Exemplary Compound No. in Table 12-3 was used instead of the diamine compound of Exemplary Compound No. I-2 in Example 160, and it was evaluated similarly to Example 41. Results are shown similarly in Table 12-3.

TABLE 12-1

| Example No. | Photo-conductor No. | Diamine compound No. | Initial Light potential (-V) | Initial Image quality | After printing 100,000 sheets Light potential (-V) | After printing 100,000 sheets Image quality |
|---|---|---|---|---|---|---|
| 160 | 120 | I-2 | 50 | 5 | 75 | 5 |
| 161 | 121 | I-5 | 45 | 5 | 65 | 5 |

TABLE 12-2

| Example No. | Photo-conductor No. | Triamine compound No. | Initial Light potential (-V) | Initial Image quality | After printing 100,000 sheets Light potential (-V) | After printing 100,000 sheets Image quality |
|---|---|---|---|---|---|---|
| 162 | 122 | II-6 | 55 | 5 | 70 | 5 |
| 163 | 123 | II-17 | 50 | 5 | 75 | 5 |

TABLE 12-3

| Example No. | Photo-conductor No. | Tetramine compound No. | Initial Light potential (-V) | Initial Image quality | After printing 100,000 sheets Light potential (-V) | After printing 100,000 sheets Image quality |
|---|---|---|---|---|---|---|
| 164 | 124 | III-2 | 55 | 5 | 85 | 5 |
| 165 | 125 | III-10 | 60 | 5 | 90 | 5 |

Example 166

Electrophotographic Photoconductor 126

Electrophotographic Photoconductor 126 was prepared in the same manner as Example 74 except that the diamine compound of Exemplary Compound No. I-4 in Example 74 was changed to a diamine compound of Exemplary Compound No. in Table 13-1 and that the charge transport material and the binder resin included in the charge transport layer was changed to a charge transport material of Structural Formula (52) below, and it was evaluated similarly to Example 41. Results are shown similarly in Table 13-1.

Example 170

Electrophotographic Photoconductor 130

Electrophotographic Photoconductor 130 was prepared in the same manner as Example 166 except that a tetramine compound of Exemplary Compound No. in Table 13-3 was used instead of the diamine compound of Exemplary Compound No. I-5 in Example 166, and it was evaluated similarly to Example 41. Results are shown similarly in Table 13-3.

Charge transport polymers of Structural Formula (52) below: 19 parts

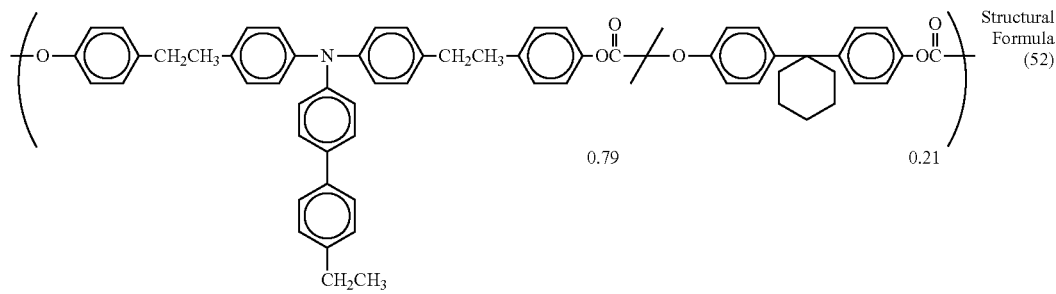

Structural Formula (52)

Example 167

Electrophotographic Photoconductor 127

Electrophotographic Photoconductor 127 was prepared in the same manner as Example 74 except that the diamine compound of Exemplary Compound No. I-4 in Example 74 was changed to a diamine compound of Exemplary Compound No. in Table 13-1 and that the charge transport material and the binder resin included in the charge transport layer was changed to a charge transport material of Structural Formula (52) above, and it was evaluated similarly to Example 41. Results are shown similarly in Table 13-1.

Example 168

Electrophotographic Photoconductor 128

Electrophotographic Photoconductor 128 was prepared in the same manner as Example 166 except that a triamine compound of Exemplary Compound No. in Table 13-2 was used instead of the diamine compound of Exemplary Compound No. I-5 in Example 166, and it was evaluated similarly to Example 41. Results are shown similarly in Table 13-2.

Example 169

Electrophotographic Photoconductor 129

Electrophotographic Photoconductor 129 was prepared in the same manner as Example 166 except that a triamine compound of Exemplary Compound No. in Table 13-2 was used instead of the diamine compound of Exemplary Compound No. I-5 in Example 166, and it was evaluated similarly to Example 41. Results are shown similarly in Table 13-2.

Example 171

Electrophotographic Photoconductor 131

Electrophotographic Photoconductor 131 was prepared in the same manner as Example 166 except that a tetramine compound of Exemplary Compound No. in Table 13-3 was used instead of the diamine compound of Exemplary Compound No. I-5 in Example 166, and it was evaluated similarly to Example 41. Results are shown similarly in Table 13-3.

TABLE 13-1

| Example No. | Photo-conductor No. | Diamine compound No. | Initial Light potential (-V) | Initial Image quality | After printing 100,000 sheets Light potential (-V) | After printing 100,000 sheets Image quality |
|---|---|---|---|---|---|---|
| 166 | 126 | I-5 | 50 | 5 | 80 | 5 |
| 167 | 127 | I-33 | 55 | 5 | 85 | 5 |

TABLE 13-2

| Example No. | Photo-conductor No. | Triamine compound No. | Initial Light potential (-V) | Initial Image quality | After printing 100,000 sheets Light potential (-V) | After printing 100,000 sheets Image quality |
|---|---|---|---|---|---|---|
| 168 | 128 | II-17 | 55 | 5 | 80 | 5 |
| 169 | 129 | II-36 | 50 | 5 | 75 | 5 |

TABLE 13-3

| Example No. | Photo-conductor No. | Tetramine compound No. | Initial Light potential (-V) | Initial Image quality | After printing 100,000 sheets Light potential (-V) | After printing 100,000 sheets Image quality |
|---|---|---|---|---|---|---|
| 170 | 130 | III-2 | 60 | 5 | 80 | 5 |
| 171 | 131 | III-10 | 65 | 5 | 85 | 5 |

Example 172

Electrophotographic Photoconductor 132

Electrophotographic Photoconductor 132 was prepared in the same manner as Example 74 except that the diamine compound of Exemplary Compound No. I-4 in Example 74 was changed to a diamine compound of Exemplary Compound No. in Table 14-1 and that the binder resin was changed to the following material, and it was evaluated similarly to Example 41. Results are shown similarly in Table 14-1.

| | |
|---|---|
| Polyarylate resin (U POLYMER, manufactured by Unitika Ltd.): | 10 parts |

Example 173

Electrophotographic Photoconductor 133

Electrophotographic Photoconductor 133 was prepared in the same manner as Example 74 except that the diamine compound of Exemplary Compound No. I-4 in Example 74 was changed to a diamine compound of Exemplary Compound No. in Table 14-1 and that the binder resin was changed to the polyarylate resin material, and it was evaluated similarly to Example 41.

Results are shown similarly in Table 14-1.

Example 174

Electrophotographic Photoconductor 134

Electrophotographic Photoconductor 134 was prepared in the same manner as Example 74 except that the diamine compound of Exemplary Compound No. I-4 in Example 74 was changed to a diamine compound of Exemplary Compound No. in Table 14-1 and that the binder resin was changed to the polyarylate resin material, and it was evaluated similarly to Example 41. Results are shown similarly in Table 14-1.

Example 175

Electrophotographic Photoconductor 135

Electrophotographic Photoconductor 135 was prepared in the same manner as Example 74 except that the diamine compound of Exemplary Compound No. I-4 in Example 74 was changed to a diamine compound of Exemplary Compound No. in Table 14-1 and that the binder resin was changed to the polyarylate resin material, and it was evaluated similarly to Example 41. Results are shown similarly in Table 14-1.

Example 176

Electrophotographic Photoconductor 136

Electrophotographic Photoconductor 136 was prepared in the same manner as Example 172 except that a triamine compound of Exemplary Compound No. in Table 14-2 was used instead of the diamine compound of Exemplary Compound No. I-3 in Example 172, and it was evaluated similarly to Example 41. Results are shown similarly in Table 14-2.

Example 177

Electrophotographic Photoconductor 137

Electrophotographic Photoconductor 137 was prepared in the same manner as Example 172 except that a triamine compound of Exemplary Compound No. in Table 14-2 was used instead of the diamine compound of Exemplary Compound No. I-3 in Example 172, and it was evaluated similarly to Example 41. Results are shown similarly in Table 14-2.

Example 178

Electrophotographic Photoconductor 138

Electrophotographic Photoconductor 138 was prepared in the same manner as Example 172 except that a triamine compound of Exemplary Compound No. in Table 14-2 was used instead of the diamine compound of Exemplary Compound No. I-3 in Example 172, and it was evaluated similarly to Example 41. Results are shown similarly in Table 14-2.

Example 179

Electrophotographic Photoconductor 139

Electrophotographic Photoconductor 139 was prepared in the same manner as Example 172 except that a triamine compound of Exemplary Compound No. in Table 14-2 was used instead of the diamine compound of Exemplary Compound No. I-3 in Example 172, and it was evaluated similarly to Example 41. Results are shown similarly in Table 14-2.

Example 180

Electrophotographic Photoconductor 140

Electrophotographic Photoconductor 140 was prepared in the same manner as Example 172 except that a tetramine compound of Exemplary Compound No. in Table 14-3 was used instead of the diamine compound of Exemplary Compound No. I-3 in Example 172, and it was evaluated similarly to Example 41. Results are shown similarly in Table 14-3.

Example 181

Electrophotographic Photoconductor 141

Electrophotographic Photoconductor 141 was prepared in the same manner as Example 172 except that a tetramine compound of Exemplary Compound No. in Table 14-3 was used instead of the diamine compound of Exemplary Compound No. I-3 in Example 172, and it was evaluated similarly to Example 41. Results are shown similarly in Table 14-3.

Example 182

Electrophotographic Photoconductor 142

Electrophotographic Photoconductor 142 was prepared in the same manner as Example 172 except that a tetramine compound of Exemplary Compound No. in Table 14-3 was used instead of the diamine compound of Exemplary Compound No. I-3 in Example 172, and it was evaluated similarly to Example 41. Results are shown similarly in Table 14-3.

TABLE 14-1

| Example No. | Photo-conductor No. | Diamine compound No. | Initial Light potential (-V) | Initial Image quality | After printing 100,000 sheets Light potential (-V) | After printing 100,000 sheets Image quality |
|---|---|---|---|---|---|---|
| 172 | 132 | I-3 | 55 | 5 | 65 | 5 |
| 173 | 133 | I-5 | 45 | 5 | 55 | 5 |
| 174 | 134 | I-27 | 50 | 5 | 70 | 5 |
| 175 | 135 | I-30 | 55 | 5 | 75 | 5 |

TABLE 14-2

| Example No. | Photo-conductor No. | Triamine compound No. | Initial Light potential (-V) | Initial Image quality | After printing 100,000 sheets Light potential (-V) | After printing 100,000 sheets Image quality |
|---|---|---|---|---|---|---|
| 176 | 136 | II-8 | 55 | 5 | 70 | 5 |
| 177 | 137 | II-17 | 50 | 5 | 60 | 5 |
| 178 | 138 | II-24 | 55 | 5 | 60 | 5 |
| 179 | 139 | II-30 | 50 | 5 | 70 | 5 |

TABLE 14-3

| Example No. | Photo-conductor No. | Tetramine compound No. | Initial Light potential (-V) | Initial Image quality | After printing 100,000 sheets Light potential (-V) | After printing 100,000 sheets Image quality |
|---|---|---|---|---|---|---|
| 180 | 140 | III-2 | 50 | 5 | 65 | 5 |
| 181 | 141 | III-10 | 55 | 5 | 65 | 5 |
| 182 | 142 | III-23 | 55 | 5 | 75 | 5 |

Example 183

Electrophotographic Photoconductor 143

Electrophotographic Photoconductor 143 was prepared by operating in the same manner as Example 41 except that the charge generation layer coating solution and the charge transport layer coating solution in Example 41 were changed to those below and that the diamine compound was changed to a diamine compound of Exemplary Compound No. in Table 15-1, and it was evaluated similarly to Example 41. Results are shown similarly in Table 15-1.

(Charge Generation Layer Coating Solution)

Figure 18:
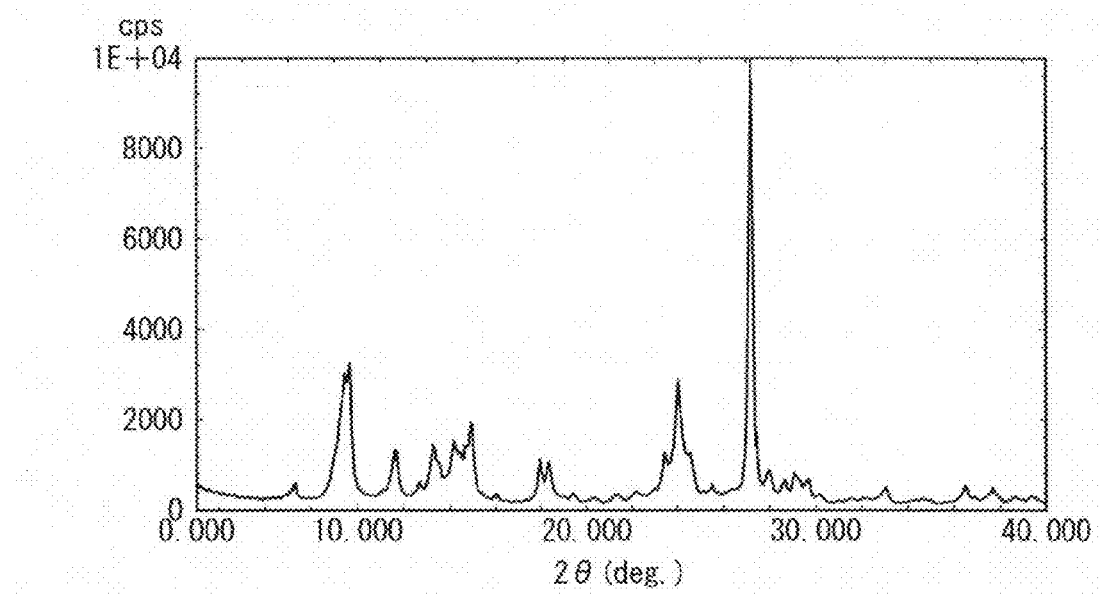
FIG. 18 is a powder XD spectrum of oxotitanium phthalocyanine used in Example 183.

| | |
|---|---|
| Oxotitanium phthalocyanine having a powder XD spectrum of FIG. 18: | 8 parts |
| Polyvinyl butyral (BX-1, manufactured by Sekisui Chemical Co., Ltd.): | 5 parts |
| 2-Butanone: | 400 parts |
| (Charge Transport Layer Coating Solution) | |
| Polycarbonate resin (Z POLYCA, manufactured by Teijin Chemicals Ltd.): | 10 parts |
| Diamine compound: | 1 part |
| Charge transport material of Structural Formula (47) below: | 7 parts |
| Toluene: | 70 parts |

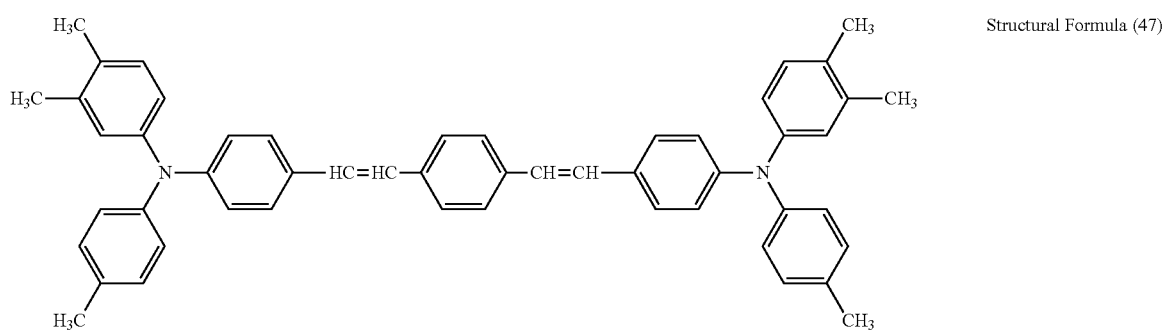

Structural Formula (47)

Example 184

Electrophotographic Photoconductor 144

Electrophotographic Photoconductor 144 was prepared by operating in the same manner as Example 41 except that the charge generation layer coating solution and the charge transport layer coating solution in Example 41 were changed to those in Example 183 (Electrophotographic Photoconductor 143) and that the diamine compound was changed to a diamine compound of Exemplary Compound No. in Table 15-1, and it was evaluated similarly to Example 41. Results are shown similarly in Table 15-1.

Example 185

Electrophotographic Photoconductor 145

Electrophotographic Photoconductor 145 was prepared in the same manner as Example 183 except that a triamine compound of Exemplary Compound No. in Table 15-2 was used instead of the diamine compound of Exemplary Compound No. I-6 in Example 183, and it was evaluated similarly to Example 41. Results are shown similarly in Table 15-2.

Example 186

Electrophotographic Photoconductor 146

Electrophotographic Photoconductor 146 was prepared in the same manner as Example 183 except that a triamine compound of Exemplary Compound No. in Table 15-2 was used instead of the diamine compound of Exemplary Compound No. I-6 in Example 183, and it was evaluated similarly to Example 41. Results are shown similarly in Table 15-2.

Example 187

Electrophotographic Photoconductor 147

Electrophotographic Photoconductor 147 was prepared in the same manner as Example 183 except that a tetramine compound of Exemplary Compound No. in Table 15-3 was used instead of the diamine compound of Exemplary Compound No. I-6 in Example 183, and it was evaluated similarly to Example 41. Results are shown similarly in Table 15-3.

Example 188

Electrophotographic Photoconductor 148

Electrophotographic Photoconductor 148 was prepared in the same manner as Example 183 except that a tetramine compound of Exemplary Compound No. in Table 15-3 was used instead of the diamine compound of Exemplary Compound No. I-6 in Example 183, and it was evaluated similarly to Example 41. Results are shown similarly in Table 15-3.

TABLE 15-1

| Example No. | Photo-conductor No. | Diamine compound No. | Initial Light potential (-V) | Initial Image quality | After printing 100,000 sheets Light potential (-V) | After printing 100,000 sheets Image quality |
|---|---|---|---|---|---|---|
| 183 | 143 | I-6 | 50 | 5 | 55 | 5 |
| 184 | 144 | I-26 | 50 | 5 | 55 | 5 |

TABLE 15-2

| Example No. | Photo-conductor No. | Triamine compound No. | Initial Light potential (-V) | Initial Image quality | After printing 100,000 sheets Light potential (-V) | After printing 100,000 sheets Image quality |
|---|---|---|---|---|---|---|
| 185 | 145 | II-3 | 40 | 5 | 50 | 5 |
| 186 | 146 | II-23 | 45 | 5 | 55 | 5 |

TABLE 15-3

| Example No. | Photo-conductor No. | Tetramine compound No. | Initial Light potential (-V) | Initial Image quality | After printing 100,000 sheets Light potential (-V) | After printing 100,000 sheets Image quality |
|---|---|---|---|---|---|---|
| 187 | 147 | III-2 | 50 | 5 | 75 | 4 |
| 188 | 148 | III-10 | 45 | 5 | 65 | 5 |

Example 189

Electrophotographic Photoconductor 149

Electrophotographic Photoconductor 149 was prepared by operating in the same manner as Example 183 except that the charge transport material in Example 183 was changed to a compound of Structural Formula (48) below and that, as the diamine compound, a diamine compound of Exemplary Compound No. in Table 16-1 was used, and it was evaluated similarly to Example 41. Results are shown similarly in Table 16-1.

Structural Formula (48)

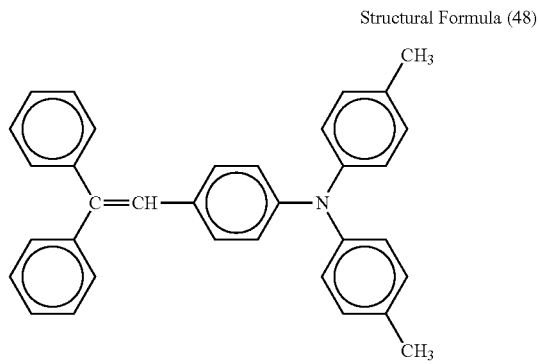

Example 190

Electrophotographic Photoconductor 150

Electrophotographic Photoconductor 150 was prepared by operating in the same manner as Example 183 except that the charge transport material in Example 183 was changed to the compound of Structural Formula (48) and that, as the diamine compound, a diamine compound of Exemplary Compound No. in Table 16-1 was used, and it was evaluated similarly to Example 41. Results to are shown similarly in Table 16-1.

Example 191

Electrophotographic Photoconductor 151

Electrophotographic Photoconductor 151 was prepared in the same manner as Example 189 except that a triamine compound of Exemplary Compound No. in Table 16-2 was used instead of the diamine compound of Exemplary Compound No. I-6 in Example 189, and it was evaluated similarly to Example 41. Results are shown similarly in Table 16-2.

Example 192

Electrophotographic Photoconductor 152

Electrophotographic Photoconductor 152 was prepared in the same manner as Example 189 except that a triamine compound of Exemplary Compound No. in Table 16-2 was used instead of the diamine compound of Exemplary Compound No. I-6 in Example 189, and it was evaluated similarly to Example 41. Results are shown similarly in Table 16-2.

Example 193

Electrophotographic Photoconductor 153

Electrophotographic Photoconductor 153 was prepared in the same manner as Example 189 except that a tetramine compound of Exemplary Compound No. in Table 16-3 was used instead of the diamine compound of Exemplary Compound No. I-6 in Example 189, and it was evaluated similarly to Example 41. Results are shown similarly in Table 16-3.

Example 194

Electrophotographic Photoconductor 154

Electrophotographic Photoconductor 154 was prepared in the same manner as Example 189 except that a tetramine compound of Exemplary Compound No. in Table 16-3 was used instead of the diamine compound of Exemplary Compound No. I-6 in Example 189, and it was evaluated similarly to Example 41. Results are shown similarly in Table 16-3.

TABLE 16-1

| | | | Initial | | After printing 100,000 sheets | |
|---|---|---|---|---|---|---|
| Example No. | Photo-conductor No. | Diamine compound No. | Light potential (-V) | Image quality | Light potential (-V) | Image quality |
| 189 | 149 | I-6 | 60 | 5 | 75 | 5 |
| 190 | 150 | I-26 | 60 | 5 | 75 | 5 |

TABLE 16-2

| | | | Initial | | After printing 100,000 sheets | |
|---|---|---|---|---|---|---|
| Example No. | Photo-conductor No. | Triamine compound No. | Light potential (-V) | Image quality | Light potential (-V) | Image quality |
| 191 | 151 | II-3 | 60 | 5 | 70 | 5 |
| 192 | 152 | II-23 | 60 | 5 | 75 | 5 |

TABLE 16-3

| | | | Initial | | After printing 100,000 sheets | |
|---|---|---|---|---|---|---|
| Example No. | Photo-conductor No. | Tetramine compound No. | Light potential (-V) | Image quality | Light potential (-V) | Image quality |
| 193 | 153 | III-2 | 45 | 5 | 65 | 5 |
| 194 | 154 | III-10 | 45 | 5 | 70 | 5 |

Comparative Example 1

Comparative Electrophotographic Photoconductor 1

Comparative Electrophotographic Photoconductor 1 was prepared in the same manner as Example 74 except that the diamine compound in Example 74 was changed to a stilbene compound of Structural Formula (53) below (described in JP-A No. 60-196768), and it was evaluated similarly to Example 41. Results are shown in Table 17.

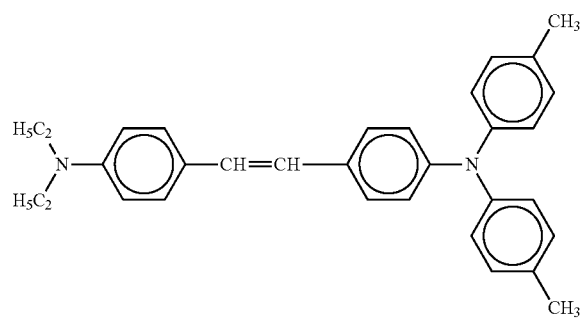

Structural Formula (53)

Comparative Example 2

Comparative Electrophotographic Photoconductor 2

Comparative Electrophotographic Photoconductor 2 was prepared in the same manner as Example 74 except that the diamine compound in Example 74 was not added to the charge transport layer coating solution and that the mass of the charge transport material was changed to 10 parts, and it was evaluated similarly to Example 41. Results are shown in Table 17.

Comparative Example 3

Comparative Electrophotographic Photoconductor 3

Comparative Electrophotographic Photoconductor 3 was prepared in the same manner as Example 74 except that the diamine compound in Example 74 was changed to a tetraphenyl methane compound of Structural Formula (54) below (described in JP-B No. 4226749), and it was evaluated similarly to Example 41. Results are shown in Table 17.

Structural Formula (54)

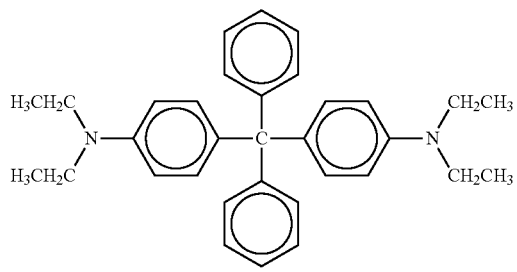

Comparative Example 4

Comparative Electrophotographic Photoconductor 4

Comparative Electrophotographic Photoconductor 4 was prepared in the same manner as Example 74 except that the diamine compound in Example 74 was changed to a hindered amine-based antioxidant of Structural Formula (55) below, and it was evaluated similarly to Example 41. Results are shown in Table 17.

Structural Formula (55)

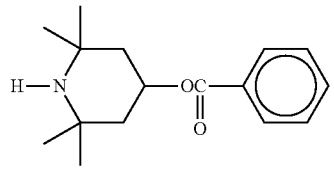

Comparative Example 5

Comparative Electrophotographic Photoconductor 5

Comparative Electrophotographic Photoconductor 5 was prepared in the same manner as Example 74 except that the diamine compound in Example 74 was changed to a diamine compound of Structural Formula (56) (described in JP-B No. 4101676), and it was evaluated similarly to Example 41. Results are shown in Table 17.

Structural Formula (56)

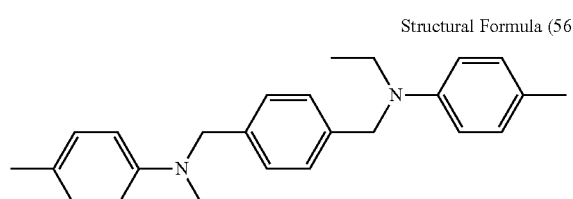

Comparative Example 6

Comparative Electrophotographic Photoconductor 6

Comparative Electrophotographic Photoconductor 6 was prepared in the same manner as Example 74 except that the diamine compound of Example 74 was changed to a diamine compound of Structural Formula (57) below (described in JP-A No. 05-158258), and it was evaluated similarly to Example 41. Results are shown in Table 17.

Structural Formula (57)

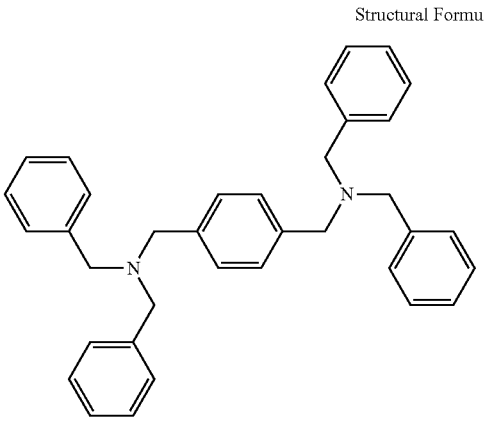

Comparative Example 7

Comparative Electrophotographic Photoconductor 7

Comparative Electrophotographic Photoconductor 7 was prepared in the same manner as Example 74 except that the diamine compound in Example 74 was changed to a diamine compound of Structural Formula (58) below (described in JP-B No. 3949550), and it was evaluated similarly to Example 41. Results are shown in Table 17.

Structural Formula (58)

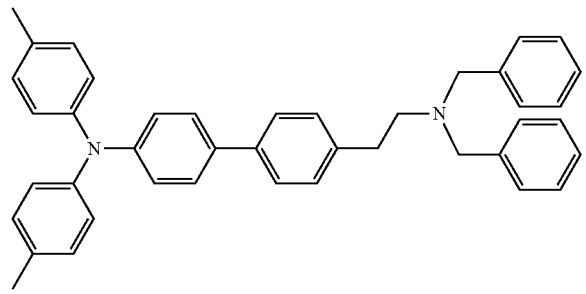

Comparative Example 8

Comparative Electrophotographic Photoconductor 8

Comparative Electrophotographic Photoconductor 8 was prepared in the same manner as Example 74 except that the diamine compound in Example 74 was changed to a diamine compound of Structural Formula (59) below (described in JP-B No. 3996490, having a melting point of 110.0° C. to 111.0° C.), and it was evaluated similarly to Example 41. Results are shown in Table 17.

Structural Formula (59)

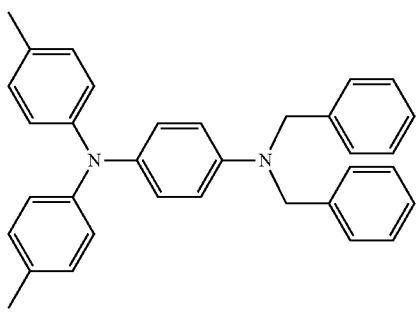

TABLE 17

| Example No. | Photo-conductor No. | Initial | | After printing 100,000 sheets | |
|---|---|---|---|---|---|
| | | Light potential (-V) | Image quality | Light potential (-V) | Image quality |
| Comparative Example 1 | Comparative Photoconductor 1 | 270 | 4 | 500 | 1 |
| Comparative Example 2 | Comparative Photoconductor 2 | 50 | 5 | 85 | 2 |
| Comparative Example 3 | Comparative Photoconductor 3 | 150 | 4 | 260 | 3 |
| Comparative Example 4 | Comparative Photoconductor 4 | 170 | 3 | 420 | 1 |
| Comparative Example 5 | Comparative Photoconductor 5 | 60 | 5 | 95 | 3 |
| Comparative Example 6 | Comparative Photoconductor 6 | 130 | 5 | 320 | 2 |
| Comparative Example 7 | Comparative Photoconductor 7 | 65 | 5 | 115 | 2 |
| Comparative Example 8 | Comparative Photoconductor 8 | 165 | 4 | 445 | 1 |

From the evaluation results above, it was confirmed that increase in the light potential was small even after printing 100,000 sheets and that a high-quality image was stably obtained with the photoconductors including the diamine compound of the present invention. On the other hand, the light potential was Comparative Photoconductors 1, 3, 4, 6 and 8 was extremely high from the beginning, which caused decrease in image density or decrease in resolution. In particular, the images obtained with Comparative Photoconductors 1 and 4 could not be determined due to significant decrease in gradation after printing 100,000 sheets. Also, Comparative Photoconductors 2, and 7 had a relatively small increase in light potential, but compared to the photoconductors of the present invention, they had a large decrease in resolution due to repeated use.

Example 195 to Example 205

Comparative Example 9

Also, the electrophotographic photoconductors of the present invention and Comparative Photoconductor 2 were allowed to stand for 4 days in a desiccator which was adjusted to have a gas concentration of nitrogen oxides (NOx) of 50 ppm, and image evaluations were carried out before and after the standing. Results are shown in Table 18.

TABLE 18

| Example No. | Photoconductor No. | Initial Image quality | Image quality after standing |
|---|---|---|---|
| 195 | 1 | 5 | 5 |
| 196 | 16 | 5 | 5 |
| 197 | 31 | 5 | 5 |
| 198 | 35 | 5 | 5 |
| 199 | 50 | 5 | 5 |
| 200 | 65 | 5 | 5 |
| 201 | 89 | 5 | 5 |
| 202 | 102 | 5 | 5 |
| 203 | 113 | 5 | 5 |
| 204 | 149 | 5 | 5 |
| 205 | 151 | 5 | 5 |
| Comparative Example 9 | Comparative Photoconductor 2 | 5 | 1 |

From the evaluation results of Table 18, it was found that, by incorporating the diamine compound of the present invention the photoconductor, durability to an oxidizing gas, i.e., suppression of resolution decrease, significantly improves. On the other hand, it was found that, in Comparative Photoconductor 2, the initial image quality is favorable but that significant decrease in resolution occurred due to the oxidizing gas.

Example 206

On an aluminum cylinder, an undercoat layer coating solution, a charge generation layer coating solution, and a charge transport layer coating solution having the following compositions were sequentially applied by a dip-coating method followed by drying, and an undercoat layer having a thickness of 3.5 μm a charge generation layer having a thickness of 0.2 μm, and a charge transport layer having a thickness of 23 μm were formed.

—Undercoat Layer Coating Solution—

| Titanium dioxide powder: | 400 parts |
|---|---|
| Melamine resin: | 65 parts |
| Alkyd resin: | 120 parts |
| 2-Butanone: | 400 parts |

—Charge Generation Layer Coating Solution—

| | |
|---|---|
| Bisazo pigment of Structural Formula (46) below: | 12 parts |

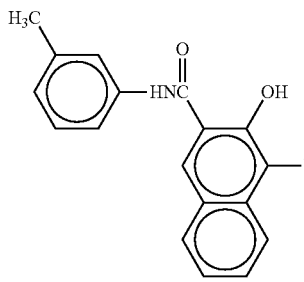

(46)

| | |
|---|---|
| Polyvinyl butyral: | 5 parts |
| 2-Butanone: | 200 parts |
| Cyclohexanone: | 400 parts |

—Charge Transport Layer Coating Solution—

| | |
|---|---|
| Polycarbonate (Z POLYCA, manufactured by Teijin Chemicals Ltd.): | 10 parts |
| Charge transport material of the structural formula below: | 10 parts |

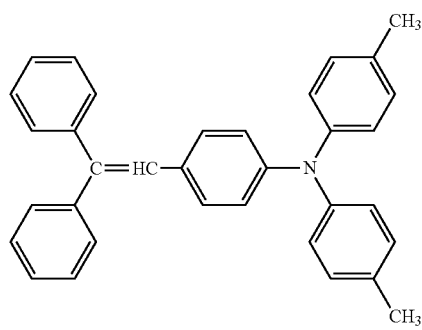

| | |
|---|---|
| Tetrahydrofuran: | 100 parts |

Next, on the charge transport layer, a protective layer having a thickness of 4 μm was further formed by spray-coating of a protective layer coating solution having the following composition. Thereby, Electrophotographic Photoconductor 155 was prepared, and it was evaluated similarly to Example 41.

—Protective Layer Coating Solution—

| | |
|---|---|
| Alumina (average primary diameter: 0.3 μm, SUMICORUNDUM AA-03, manufactured by Sumitomo Chemical Co., Ltd.): | 2 parts |
| Compound represented by Exemplary Compound I-4: | 0.5 parts |
| Polycarbonate (Z POLYCA, manufactured by Teijin Chemicals Ltd.): | 6 parts |
| Tetrahydrofuran: | 220 parts |
| Cyclohexanone: | 80 parts |

Example 207

Electrophotographic Photoconductor 156 was prepared in the same manner as Example 206 except that Exemplary Compound I-4 in the protective layer coating solution of Example 206 was changed to Exemplary Compound II-3, and it was evaluated similarly to Example 41.

Example 208

Electrophotographic Photoconductor 157 was prepared in the same manner as Example 206 except that Exemplary Compound I-4 in the protective layer coating solution of Example 206 was changed to Exemplary Compound III-10, and it was evaluated similarly to Example 41.

Example 209

On an aluminum cylinder, an undercoat layer coating solution, a charge generation layer coating solution, and a charge transport layer coating solution having the following compositions were sequentially applied by a dip-coating method followed by drying, and an undercoat layer having a thickness of 3.5 μm, a charge generation layer having a thickness of 0.2 μm, and a charge transport layer having a thickness of 23 μm were formed.

—Undercoat Layer Coating Solution—

| | |
|---|---|
| Titanium dioxide powder: | 400 parts |
| Melamine resin: | 65 parts |
| Alkyd resin: | 120 parts |
| 2-Butanone: | 400 parts |

—Charge Generation Layer Coating Solution—

| | |
|---|---|
| Bisazo pigment of Structural Formula (46) below: | 12 parts |

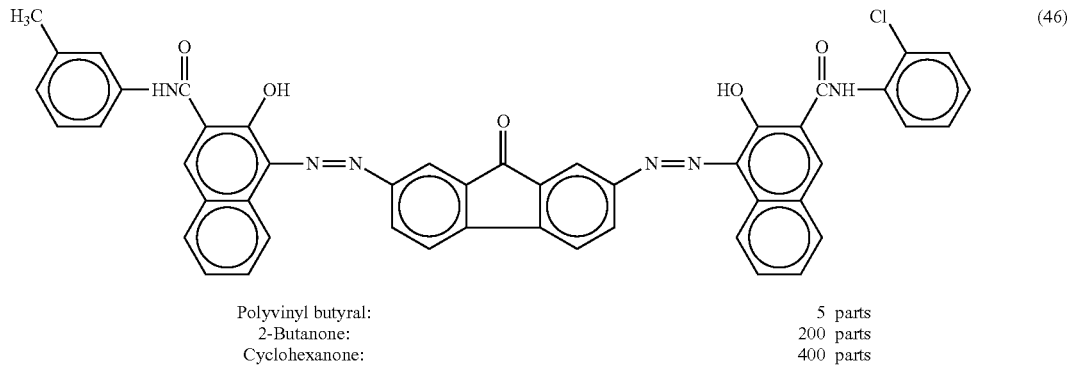

| | |
|---|---|
| Polyvinyl butyral: | 5 parts |
| 2-Butanone: | 200 parts |
| Cyclohexanone: | 400 parts |

—Charge Transport Layer Coating Solution—

| | |
|---|---|
| Polycarbonate (Z POLYCA, Manufactured by Teijin Chemicals Ltd.): | 10 parts |
| Charge transport material of the following structural formula: | 10 parts |

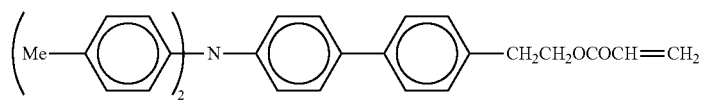

| | |
|---|---|
| Tetrahydrofuran: | 100 parts |

On the charge transport layer, a protective layer coating solution having the following composition was further spray-coated, and a protective layer formed thereby was cured by UV irradiation. Thereafter, it was dried at 130° C. for 20 minutes, and the protective layer having a thickness of 4 μm was formed. Electrophotographic Photoconductor 158 was prepared thereby, and it was evaluated similarly to Example 41.

—Protective Layer Coating Solution—

| | |
|---|---|
| Exemplary Compound I-4: | 5 parts |
| Monomer of a structural formula below: | 2.5 parts |

$$\left(Me-\bigcirc-\right)_2 N-\bigcirc-\bigcirc-\bigcirc-CH_2CH_2OCOCH=CH_2$$

| | |
|---|---|
| Trimethylolpropane triacrylate: | 2.5 parts |
| Polymerization initiator, 1-hydroxy-cyclohexyl-phenyl-ketone (IRGACURE 184, manufactured by Ciba Specialty Chemicals) | 0.5 parts |
| Tetrahydrofuran: | 50 parts |

Example 210

Electrophotographic Photoconductor 159 was prepared in the same manner as Example 209 except that Exemplary Compound I-4 in the protective layer coating solution of Example 209 was changed to Exemplary Compound II-3, and it was evaluated similarly to Example 41.

Example 211

Electrophotographic Photoconductor 160 was prepared in the same manner as Example 209 except that Exemplary Compound I-4 in the protective layer coating solution of Example 209 was changed to Exemplary Compound III-10, and it was evaluated similarly to Example 41.

Example 212

On an aluminum cylinder, an undercoat layer coating solution, a charge generation layer coating solution, and a charge transport layer coating solution having the following compositions were sequentially applied by a dip-coating method followed by drying, and an undercoat layer having a thickness of 3.5 μm, a charge generation layer having a thickness of 0.2 μm, and a charge transport layer having a thickness of 23 μm were formed.

—Undercoat Layer Coating Solution—

| Titanium dioxide powder: | 400 parts |
| Melamine resin: | 65 parts |
| Alkyd resin: | 120 parts |
| 2-Butanone: | 400 parts |

—Charge Generation Layer Coating Solution—

| Bisazo pigment of Structural Formula (46) below: | 12 parts |

(46)

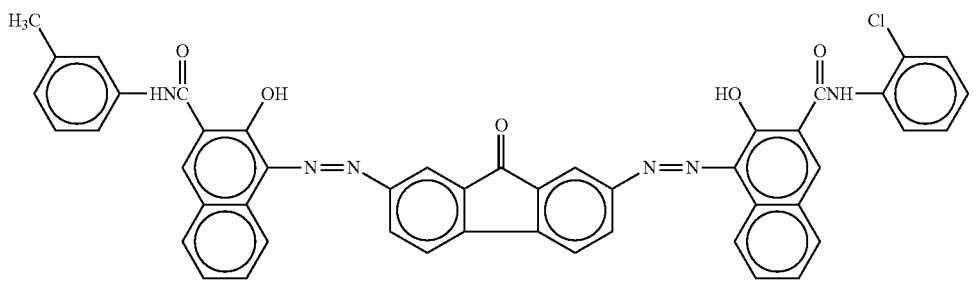

| Polyvinyl butyral: | 5 parts |
| 2-Butanone: | 200 parts |
| Cyclohexanone: | 400 parts |

—Charge Transport Layer Coating Solution—

| Polycarbonate (Z POLYCA, manufactured by Teijin Chemicals Ltd.): | 10 parts |
| Charge transport material having the following structural formula: | 10 parts |

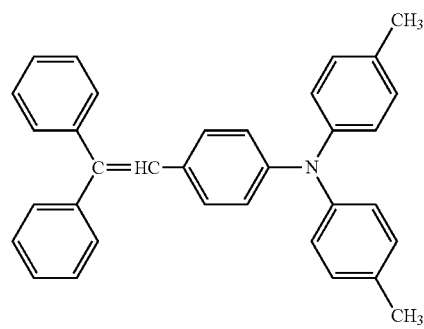 [SMILES: Cc1ccc(N(c2ccc(C)cc2)c2ccc(C=C(c3ccccc3)c3ccccc3)cc2)cc1]

| Tetrahydrofuran: | 100 parts |

Next, on the charge transport layer, a protective layer having a thickness of 4 μm was further formed by spray-coating a protective layer coating solution having the following composition followed by heating at 150° C. for 20 minutes. Electrophotographic Photoconductor 161 was prepared thereby, and it was evaluated similarly to Example 41.

—Protective Layer Coating Solution—

| Exemplary Compound I-4: | 5 parts |
| Polyol having the following structural formula: | 2.5 parts |

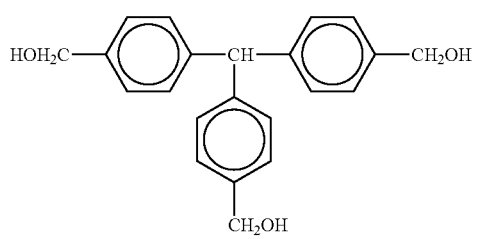

| Isocyanate (TAKENATE D140N <IPDI adduct>, manufactured by Mitsui Takeda Chemicals, Inc.): | 2.5 parts |

Results of Examples 206 to 212 are shown in Table 19.

TABLE 19

| | | | Initial | | After printing 100,000 sheets | |
| Example No. | Photo-conductor No. | Amine compound No. | Light potential (-V) | Image quality | Light potential (-V) | Image quality |
| 206 | 155 | I-4 | 50 | 5 | 75 | 5 |
| 207 | 156 | II-3 | 45 | 5 | 75 | 5 |
| 208 | 157 | III-10 | 50 | 5 | 80 | 5 |

TABLE 19-continued

| Example No. | Photo-conductor No. | Amine compound No. | Initial Light potential (-V) | Image quality | After printing 100,000 sheets Light potential (-V) | Image quality |
|---|---|---|---|---|---|---|
| 209 | 158 | I-4 | 55 | 5 | 85 | 5 |
| 210 | 159 | II-3 | 55 | 5 | 75 | 5 |
| 211 | 160 | III-10 | 60 | 5 | 80 | 5 |
| 212 | 161 | I-4 | 60 | 5 | 80 | 5 |

Aspects of the present invention are as follows.

<1> An amine compound, represented by General Formula (I) below:

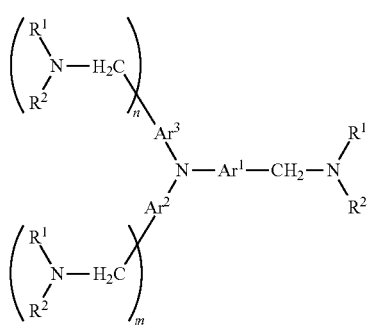

General Formula (I)

[in General Formula (I), $R^1$ and $R^2$ represent a substituted or unsubstituted alkyl group, a substituted or unsubstituted aralkyl group, or a substituted or unsubstituted aromatic hydrocarbon group, which may be identical or different; m and n are an integer of 1 or 0; $Ar^1$ represents a substituted or unsubstituted aromatic hydrocarbon group; $Ar^2$ and $Ar^3$ represent a substituted or unsubstituted alkyl group, a substituted or unsubstituted aralkyl group, or a substituted or unsubstituted aromatic hydrocarbon group; and $Ar^1$ and $Ar^2$ or $Ar^2$ and $Ar^3$ may bind to each other to form a substituted or unsubstituted heterocyclic group including a nitrogen atom.]

<2> The amine compound according to <1>, wherein the amine compound is an amine compound represented by any one of General Formulae (1) to (3) below:

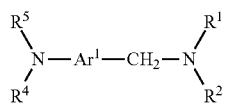

General Formula (1)

[in General Formula (1), $R^1$ and $R^2$ represent a substituted or unsubstituted alkyl group, a substituted or unsubstituted aralkyl group, or a substituted or unsubstituted aromatic hydrocarbon group, which may be identical or different; $Ar^1$ represents a substituted or unsubstituted aromatic hydrocarbon group; $R^4$ and $R^5$ represent a substituted or unsubstituted alkyl group, a substituted or unsubstituted aralkyl group, or a substituted or unsubstituted aromatic hydrocarbon group; and $Ar^1$ and $R^4$ or $R^4$ and $R^5$ may bind to each other to form a substituted or unsubstituted heterocyclic group including a nitrogen atom,]

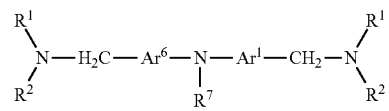

General Formula (2)

[in General Formula (2), $R^1$, $R^2$ and $R^7$ represent a substituted or unsubstituted alkyl group, a substituted or unsubstituted aralkyl group, or a substituted or unsubstituted aromatic hydrocarbon group, which may be identical or different; $R^1$ and $R^2$ may bind to each other to form a substituted or unsubstituted heterocyclic group including a nitrogen atom; $Ar^1$ and $Ar^6$ represent a substituted or unsubstituted aromatic hydrocarbon group,]

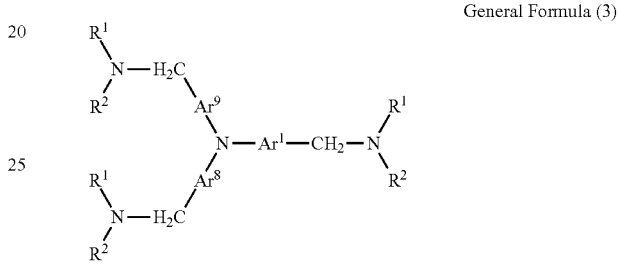

General Formula (3)

[in General Formula (3), $R^1$ and $R^2$ represent a substituted or unsubstituted alkyl group, a substituted or unsubstituted aralkyl group, or a substituted or unsubstituted aromatic hydrocarbon group, which may be identical or different; $R^1$ and $R^2$ may bind to each other to form a substituted or unsubstituted heterocyclic group including a nitrogen atom; $Ar^1$, $Ar^8$ and $Ar^9$ represent a substituted or unsubstituted aromatic hydrocarbon group.]

<3> An electrophotographic photoconductor, including:
an electrically conductive substrate; and
a photoconductive layer on the electrically conductive substrate,
wherein the photoconductive layer includes an amine compound represented by General Formula (I) below:

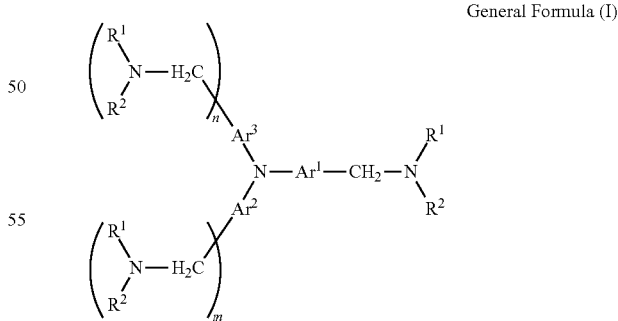

General Formula (I)

[in General Formula (I), $R^1$ and $R^2$ represent a substituted or unsubstituted alkyl group, a substituted or unsubstituted aralkyl group, or a substituted or unsubstituted aromatic hydrocarbon group, which may be identical or different; m and n are an integer of 1 or 0; $Ar^1$ represents a substituted or unsubstituted aromatic hydrocarbon group; $Ar^2$ and $Ar^3$ represent a substituted or unsubstituted alkyl group, a substituted or unsubstituted aralkyl group, or a substituted or unsubstituted aromatic hydrocarbon group; and $Ar^1$ and $Ar^2$ or $Ar^2$ and $Ar^3$ may bind to each other to form a substituted or unsubstituted heterocyclic group including a nitrogen atom.]

<4> The electrophotographic photoconductor according to <3>, wherein the photoconductive layer includes a charge transport material.

<5> The electrophotographic photoconductor according to <4>, wherein the charge transport material is a stilbene compound represented by General Formula (4) below,

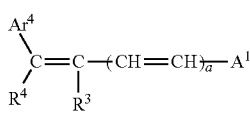

General Formula (4)

[in General Formula (4), a represents an integer of 0 or 1; $R^3$ represents a hydrogen atom, an alkyl group or a substituted or unsubstituted phenyl group; $Ar^4$ represents a substituted or unsubstituted aromatic hydrocarbon group; $R^4$ represents an alkyl group having 1 to 4 carbon atoms or a substituted or unsubstituted aromatic hydrocarbon group; $Ar^4$ and $R^4$ may jointly form a ring; $A^1$ represents a 9-anthryl group, a substituted or unsubstituted carbazolyl group, General Formula (5) below or General Formula (6) below; when a is 0, $A^1$ and $R^3$ may jointly form a ring,

General Formula (5)

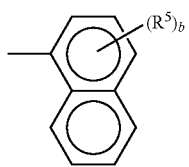

General Formula (6)

(in General Formula (5) or (6), $R^5$ represents a hydrogen atom, an alkyl group, an alkoxy group, a halogen atom or General Formula (7) below; b represents an integer of 1 to 3, and when b is 2 or greater, $R^5$ may be identical or different,)

General Formula (7)

(in General Formula (7), $R^6$ and $R^7$ represent a substituted or unsubstituted aromatic hydrocarbon group, and $R^6$ and $R^7$ are identical or different and may form a ring.)]

<6> The electrophotographic photoconductor according to <4>, wherein the charge transport material is an aminobiphenyl compound represented by General Formula (8) below,

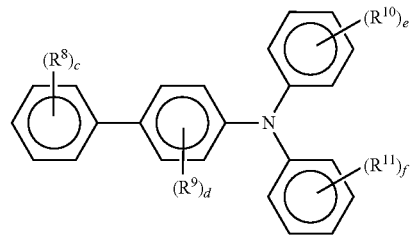

General Formula (8)

[in General Formula (8), $R^8$, $R^{10}$ and $R^{11}$ represent a hydrogen atom, an amino group, an alkoxy group, a thioalkoxy group, an aryloxy group, a methylenedioxy group, a substituted or unsubstituted alkyl group, a halogen atom, or a substituted or unsubstituted aryl group; $R^9$ represents a hydrogen atom, an alkoxy group, a substituted or unsubstituted alkyl group or a halogen atom; c, d, e and f represent an integer of 1, 2, 3 or 4, and when each thereof is an integer of 2, 3 or 4, $R^8$, $R^9$, $R^{10}$ or $R^{11}$ above are identical or different.]

<7> The electrophotographic photoconductor according to <4>, wherein the charge transport material is a diolefin aromatic compound represented by General Formula (9),

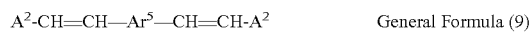

$$A^2\text{-CH}=\text{CH}-Ar^5-\text{CH}=\text{CH-}A^2$$ General Formula (9)

[in General Formula (9), $Ar^5$ represents a substituted or unsubstituted aromatic hydrocarbon group; $A^2$ represents General Formula (10) below,

General Formula (10)

(in General Formula (10), $Ar^6$ represents a substituted or unsubstituted aromatic hydrocarbon group; $R^{12}$ and $R^{13}$ represent a substituted or unsubstituted alkyl group or a substituted or unsubstituted aryl group.)]

<8> The electrophotographic photoconductor according to <4>, wherein the charge transport material is a polymeric charge transport material.

<9> The electrophotographic photoconductor according to <8>, wherein the polymeric charge transport material is a compound represented by General Formula (11) below,

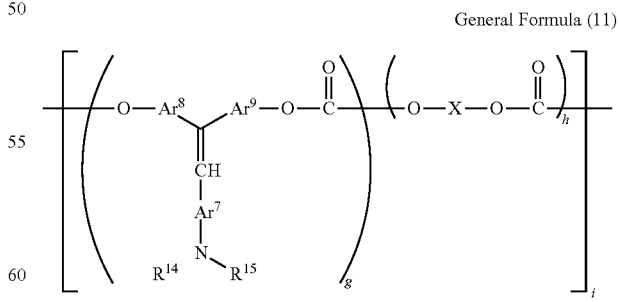

General Formula (11)

[in General Formula (11), $R^{14}$ and $R^{15}$ represent a substituted or unsubstituted aromatic hydrocarbon group; $Ar^7$, $Ar^s$ and $Ar^9$ represent identical or different aromatic hydrocarbon group; g and h represent compositions: $0.1 \leq g \leq 1$; $0 \leq h \leq 0.9$; i represents a number of repeating units and is an integer of 5 to 5,000; X represents an aliphatic divalent group, a cyclic aliphatic divalent group, or a divalent group represented by General Formula (12) below,

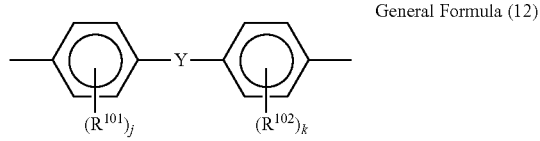

General Formula (12)

(in General Formula (12), each of $R^{101}$ and $R^{102}$ independently represents a substituted or unsubstituted alkyl group, an aromatic hydrocarbon group, or a halogen atom; j and k represent an integer of 0 to 4; Y represents a single bond, a linear, branched or cyclic alkylene group having 1 to 12 carbon atoms; —O—, —S—, —SO—, —SO$_2$—, —CO—, —CO—O—Z—O—CO— (where Z represents an divalent aliphatic group), or General Formula (13) below, where $R^{101}$ and $R^{102}$ are identical or different, respectively,)

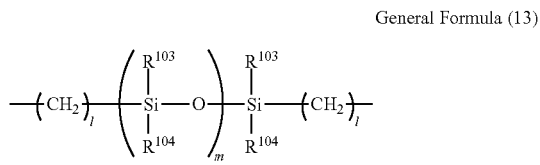

General Formula (13)

(in General Formula (13), l represents an integer of 1 to 20; m represents an integer of 1 to 2,000; $R^{103}$ and $R^{104}$ represent a substituted or unsubstituted alkyl group or aryl group, where $R^{103}$ and $R^{104}$ are identical or different, respectively.)]

<10> The electrophotographic photoconductor according to <8>, wherein the polymeric charge transport material is a compound represented by General Formula (14) below,

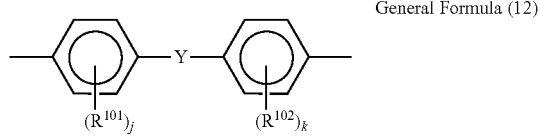

General Formula (14)

[in General Formula (14), $Ar^{10}$, $Ar^{11}$, $Ar^{12}$, $Ar^{13}$ and $Ar^{14}$ represent a substituted or unsubstituted aromatic hydrocarbon group; Z represents an aromatic hydrocarbon group or $Ar^{15}$-Za-$Ar^{15}$—, where $Ar^{15}$ represents a substituted or unsubstituted aromatic hydrocarbon group, Za represents O, S or an alkylene group; $R^{105}$ and $R^{106}$ represent a linear or branched alkylene group; n represents 0 or 1; g and h represent compositions: 0.1≤g≤1; 0≤h≤0.9; i represents a number of repeating units and is an integer of 5 to 5,000; X represents an aliphatic divalent group, a cyclic aliphatic divalent group, or a divalent group represented by General Formula (12) below,

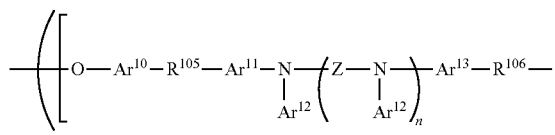

General Formula (12)

(in General Formula (12), each of $R^{101}$ and $R^{102}$ independently represents a substituted or unsubstituted alkyl group, an aromatic hydrocarbon group, or a halogen atom; j and k represent an integer of 0 to 4; Y represents a single bond, a linear, branched or cyclic alkylene group having 1 to 12 carbon atoms; —O—, —S—, —SO—, —SO$_2$—, —CO—, —CO—O—Z—O—CO— (where Z represents an divalent aliphatic group), or General Formula (13) below, where $R^{101}$ and $R^{102}$ are identical or different, respectively,)

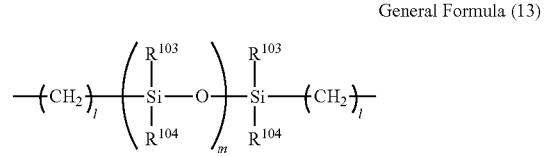

General Formula (13)

(in General Formula (13), l represents an integer of 1 to 20; m represents an integer of 1 to 2,000; $R^{103}$ and $R^{104}$ represent a substituted or unsubstituted alkyl group or aryl group, where $R^{103}$ and $R^{104}$ are identical or different, respectively.)]

<11> The electrophotographic photoconductor according to any one of <3> to <10>, wherein the electrophotographic photoconductor includes a protective layer on an outermost surface, and the protective layer includes the amine compound represented by General Formula (I).

<12> The electrophotographic photoconductor according to <11>, wherein the protective layer includes a filler.

<13> The electrophotographic photoconductor according to any one of <11> to <12>, wherein the protective layer includes a resin formed by curing a polymerizable monomer.

<14> An image forming method, including:
charging a surface of an electrophotographic photoconductor;
exposing the charged surface of the electrophotographic photoconductor to form an electrostatic latent image;
developing the electrostatic latent image using a toner to form a visible image; and
transferring the visible image to a recording medium,
wherein the electrophotographic photoconductor is the electrophotographic photoconductor according to any one of <3> to <13>.

<15> The image forming method according to <14>, wherein, in the exposing, the electrostatic latent image is digitally written on the electrophotographic photoconductor using any one of a laser diode and a light-emitting diode.

<16> An image forming apparatus, including:
an electrophotographic photoconductor;
a charging unit which charges a surface of the electrophotographic photoconductor;
an exposure unit which exposes the charged surface of the electrophotographic photoconductor to form an electrostatic latent image;
a developing unit which develops the electrostatic latent image using a toner to form a visible image; and a transfer unit which transfers the visible image to a recording medium, wherein the electrophotographic photoconductor is the electrophotographic photoconductor according to any one of <3> to <13>.

<17> The image forming apparatus according to <16>, wherein the exposure unit is any one of a laser diode and a light-emitting diode, and the electrostatic latent image is digitally written on the electrophotographic photoconductor using the exposure unit.

<18> A process cartridge, including:

an electrophotographic photoconductor; and a developing unit which develops an electrostatic latent image on the electrophotographic photoconductor using a toner to form a visible image, wherein the electrophotographic photoconductor is the electrophotographic photoconductor according to any one of <3> to <13>.

This application claims priority to Japanese applications No. 2012-021569, filed on Feb. 3, 2012, and No. 2012-042916, filed on Feb. 29, 2012, and incorporated herein by reference.

What is claimed is:

1. An electrophotographic photoconductor, comprising:

an electrically conductive substrate; and a photoconductive layer on the electrically conductive substrate, wherein the photoconductive layer includes an amine compound represented by Formula (I) below:

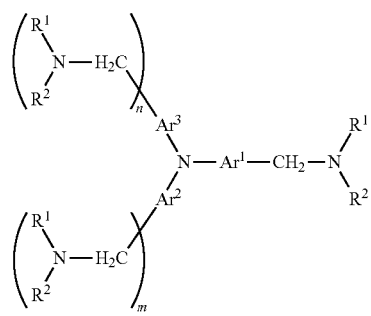

Formula (I)

wherein in Formula (I), $R^1$ and $R^2$ represent a substituted or unsubstituted alkyl group, a substituted or unsubstituted aralkyl group, or a substituted or unsubstituted aromatic hydrocarbon group, which may be identical or different; m and n are an integer of 1 or 0; $Ar^1$ represents a substituted or unsubstituted aromatic hydrocarbon group; $Ar^2$ and $Ar^3$ represent a substituted or unsubstituted alkyl group, a substituted or unsubstituted aralkyl group, or a substituted or unsubstituted aromatic hydrocarbon group; and $Ar^1$ and $Ar^2$ or $Ar^2$ and $Ar^3$ may bind to each other to form a substituted or unsubstituted heterocyclic group including a nitrogen atom.

2. The electrophotographic photoconductor according to claim 1, wherein the photoconductive layer includes a charge transport material.

3. The electrophotographic photoconductor according to claim 2, wherein the charge transport material is a stilbene compound represented by Formula (4) below,

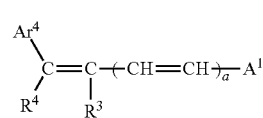

Formula (4)

wherein in Formula (4), a represents an integer of 0 or 1; $R^3$ represents a hydrogen atom, an alkyl group or a substituted or unsubstituted phenyl group; $Ar^4$ represents a substituted or unsubstituted aromatic hydrocarbon group; $R^4$ represents an alkyl group having 1 to 4 carbon atoms or a substituted or unsubstituted aromatic hydrocarbon group; $A^1$ represents a 9-anthryl group, a substituted or unsubstituted carbazolyl group, Formula (5) below or Formula (6) below;

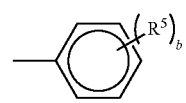

Formula (5)

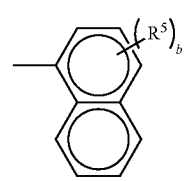

Formula (6)

wherein in Formula (5) or (6), $R^5$ represents a hydrogen atom, an alkyl group, an alkoxy group, a halogen atom or Formula (7) below; b represents an integer of 1 to 3, and when b is 2 or greater, $R^5$ may be identical or different,

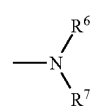

Formula (7)

wherein in Formula (7), $R^6$ and $R^7$ represent a substituted or unsubstituted aromatic hydrocarbon group, and $R^6$ and $R^7$ are identical or different.

4. The electrophotographic photoconductor according to claim 2, wherein the charge transport material is an aminobiphenyl compound represented by Formula (8) below,

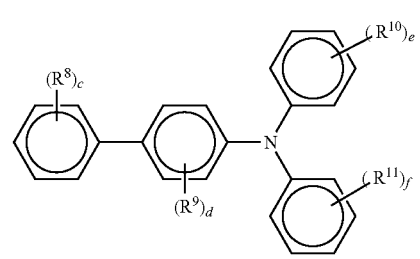

Formula (8)

wherein in Formula (8), $R^8$, $R^{10}$ and $R^{11}$ represent a hydrogen atom, an amino group, an alkoxy group, a thioalkoxy group, an aryloxy group, a methylenedioxy group, a substituted or unsubstituted alkyl group, a halogen atom, or a substituted or unsubstituted aryl group; $R^9$ represents a hydrogen atom, an alkoxy group, a substituted or unsubstituted alkyl group or a halogen atom; c, d, e and f represent an integer of 1, 2, 3 or 4, and when each thereof is an integer of 2, 3 or 4, $R^8$, $R^9$, $R^{10}$ or $R^{11}$ above are identical or different.

5. The electrophotographic photoconductor according to claim 2, wherein the charge transport material is a diolefin aromatic compound represented by Formula (9),

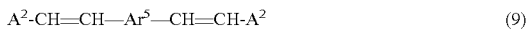
(9)

wherein in Formula (9), $Ar^5$ represents a substituted or unsubstituted aromatic hydrocarbon group; $A^2$ represents Formula (10) below,

Formula (10)

wherein in Formula (10), $Ar^6$ represents a substituted or unsubstituted aromatic hydrocarbon group; $R^{12}$ and $R^{13}$ represent a substituted or unsubstituted alkyl group or a substituted or unsubstituted aryl group.

6. The electrophotographic photoconductor according to claim 2, wherein the charge transport material is a polymeric charge transport material.

7. The electrophotographic photoconductor according to claim 6, wherein the polymeric charge transport material is a compound represented by Formula (11) below,

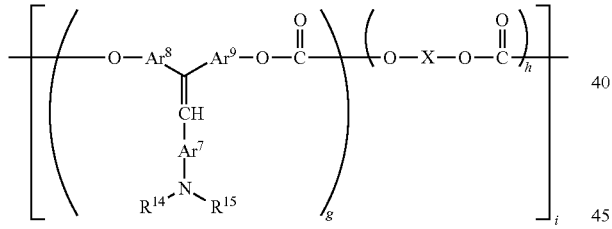
Formula (11)

wherein in Formula (11), $R^{14}$ and $R^{15}$ represent a substituted or unsubstituted aromatic hydrocarbon group; $Ar^7$, $Ar^8$ and $Ar^9$ represent identical or different aromatic hydrocarbon group; g and h represent compositions: $0.1 \leq g \leq 1$; $0 \leq h \leq 0.9$; i represents a number of repeating units and is an integer of 5 to 5,000; X represents an aliphatic divalent group, a cyclic aliphatic divalent group, or a divalent group represented by Formula (12) below,

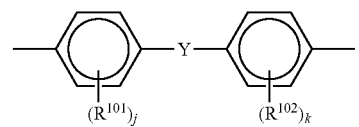
Formula (12)

wherein in Formula (12), each of $R^{101}$ and $R^{102}$ independently represents a substituted or unsubstituted alkyl group, an aromatic hydrocarbon group, or a halogen atom; j and k represent an integer of 0 to 4; Y represents a single bond, a linear, branched or cyclic alkylene group having 1 to 12 carbon atoms; —O—, —S—, —SO—, —SO$_2$—, —CO—, —CO—O—Z—O—CO— where Z represents an divalent aliphatic group, or Formula (13) below, where $R^{101}$ and $R^{102}$ are identical or different, respectively,

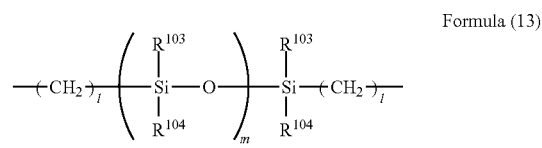
Formula (13)

wherein in Formula (13), l represents an integer of 1 to 20; m represents an integer of 1 to 2,000; $R^{103}$ and $R^{104}$ represent a substituted or unsubstituted alkyl group or aryl group, where $R^{103}$ and $R^{104}$ are identical or different, respectively.

8. The electrophotographic photoconductor according to claim 6, wherein the polymeric charge transport material is a compound represented by Formula (14) below,

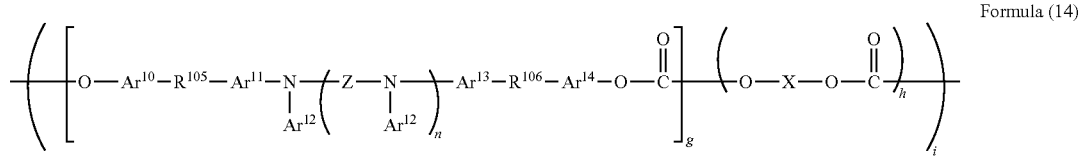
Formula (14)

wherein in Formula (14), $Ar^{10}$, $Ar^{11}$, $Ar^{12}$, $Ar^{13}$ and $Ar^{14}$ represent a substituted or unsubstituted aromatic hydrocarbon group; Z represents an aromatic hydrocarbon group or $Ar^{15}$-Za-$Ar^{15}$—, where $Ar^{15}$ represents a substituted or unsubstituted aromatic hydrocarbon group, Za represents O, S or an alkylene group; $R^{105}$ and $R^{106}$ represent a linear or branched alkylene group; n represents 0 or 1; g and h represent compositions: $0.1 \leq g \leq 1$; $0 \leq h \leq 0.9$; i represents a number of repeating units and is an integer of 5 to 5,000; X represents an aliphatic divalent group, a cyclic aliphatic divalent group, or a divalent group represented by Formula (12) below,

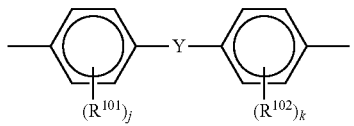

Formula (12)

wherein in Formula (12), each of $R^{101}$ and $R^{102}$ independently represents a substituted or unsubstituted alkyl group, an aromatic hydrocarbon group, or a halogen atom; j and k represent an integer of 0 to 4; Y represents a single bond, a linear, branched or cyclic alkylene group having 1 to 12 carbon atoms; —O—, —S—, —SO—, —SO$_2$—, —CO—, —CO—O—Z—O—CO— where Z represents an divalent aliphatic group, or Formula (13) below, where $R^{101}$ and $R^{102}$ are identical or different, respectively,

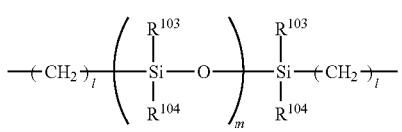

Formula (13)

wherein in Formula (13), l represents an integer of 1 to 20; m represents an integer of 1 to 2,000; $R^{103}$ and $R^{104}$ represent a substituted or unsubstituted alkyl group or aryl group, where $R^{103}$ and $R^{104}$ are identical or different, respectively.

9. The electrophotographic photoconductor according to claim 1, wherein the electrophotographic photoconductor includes a protective layer on an outermost surface, and the protective layer includes the amine compound represented by Formula (I).

10. The electrophotographic photoconductor according to claim 9, wherein the protective layer includes a filler.

11. The electrophotographic photoconductor according to claim 9, wherein the protective layer includes a resin formed by curing a polymerizable monomer.

12. The electrophotographic photoconductor according to claim 1, wherein the amine compound is an amine compound represented by Formula (1) below:

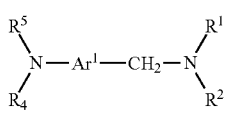

Formula (1)

wherein in Formula (1), $R^1$ and $R^2$ represent a substituted or unsubstituted alkyl group, a substituted or unsubstituted aralkyl group, or a substituted or unsubstituted aromatic hydrocarbon group, which may be identical or different; $Ar^1$ represents a substituted or unsubstituted aromatic hydrocarbon group; $R^4$ and $R^5$ represent a substituted or unsubstituted alkyl group, a substituted or unsubstituted aralkyl group, or a substituted or unsubstituted aromatic hydrocarbon group; and $Ar^1$ and $R^4$ or $R^4$ and $R^5$ may bind to each other to form a substituted or unsubstituted heterocyclic group including a nitrogen atom.

13. The electrophotographic photoconductor according to claim 1, wherein the amine compound is an amine compound represented by Formula (2) below:

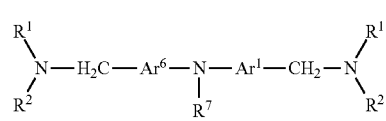

Formula (2)

wherein in Formula (2), $R^1$, $R^2$ and $R^7$ represent a substituted or unsubstituted alkyl group, a substituted or unsubstituted aralkyl group, or a substituted or unsubstituted aromatic hydrocarbon group, which may be identical or different; $R^1$ and $R^2$ may bind to each other to form a substituted or unsubstituted heterocyclic group including a nitrogen atom; $Ar^1$ and $Ar^6$ represent a substituted or unsubstituted aromatic hydrocarbon group.

14. The electrophotographic photoconductor according to claim 1, wherein the amine compound is an amine compound represented by Formula (3) below:

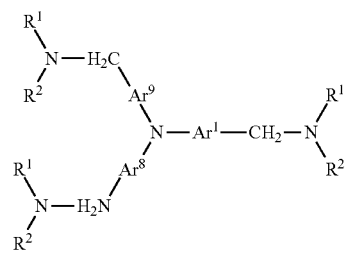

Formula (3)

wherein in Formula (3), $R^1$ and $R^2$ represent a substituted or unsubstituted alkyl group, a substituted or unsubstituted aralkyl group, or a substituted or unsubstituted aromatic hydrocarbon group, which may be identical or different; $R^1$ and $R^2$ may bind to each other to form a substituted or unsubstituted heterocyclic group including a nitrogen atom; $Ar^1$, $Ar^8$ and $Ar^9$ represent a substituted or unsubstituted aromatic hydrocarbon group.

15. An image forming apparatus, comprising:

an electrophotographic photoconductor;

a charging unit which charges a surface of the electrophotographic photoconductor;

an exposure unit which exposes the charged surface of the electrophotographic photoconductor to form an electrostatic latent image;

a developing unit which develops the electrostatic latent image using a toner to form a visible image; and a transfer unit which transfers the visible image to a recording medium, wherein the electrophotographic photoconductor is an electrophotographic photoconductor which comprises:

an electrically conductive substrate; and a photoconductive layer on the electrically conductive substrate, wherein the photoconductive layer comprises an amine compound represented by Formula (I) below:

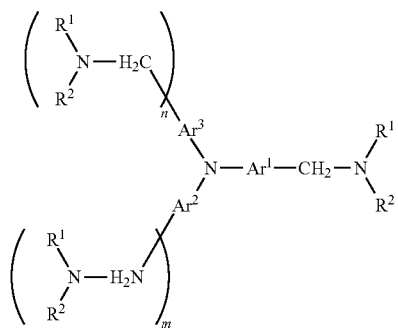

Formula (I)

wherein in Formula (I), $R^1$ and $R^2$ represent a substituted or unsubstituted alkyl group, a substituted or unsubstituted aralkyl group, or a substituted or unsubstituted aromatic hydrocarbon group, which may be identical or different; m and n are an integer of 1 or 0; $Ar^1$ represents a substituted or unsubstituted aromatic hydrocarbon group; $Ar^2$ and $Ar^3$ represent a substituted or unsubstituted alkyl group, a substituted or unsubstituted aralkyl group, or a substituted or unsubstituted aromatic hydrocarbon group; and $Ar^1$ and $Ar^2$ or $Ar^2$ and $Ar^3$ may bind to each other to form a substituted or unsubstituted heterocyclic group including a nitrogen atom.

16. The image forming apparatus according to claim 15, wherein the exposure unit is any one of a laser diode and a light-emitting diode, and the electrostatic latent image is digitally written on the electrophotographic photoconductor using the exposure unit.

* * * * *